United States Patent
Demopulos et al.

(10) Patent No.: US 7,067,144 B2
(45) Date of Patent: Jun. 27, 2006

(54) COMPOSITIONS AND METHODS FOR SYSTEMIC INHIBITION OF CARTILAGE DEGRADATION

(75) Inventors: Gregory A. Demopulos, Mercer Island, WA (US); Pamela Pierce Palmer, San Francisco, CA (US); Jeffrey M. Herz, Mill Creek, WA (US)

(73) Assignee: Omeros Corporation, Seattle, WA (US)

( * ) Notice: Subject to any disclaimer, the term of this patent is extended or adjusted under 35 U.S.C. 154(b) by 347 days.

(21) Appl. No.: 10/356,649

(22) Filed: Jan. 31, 2003

(65) Prior Publication Data
US 2003/0235589 A1     Dec. 25, 2003

Related U.S. Application Data

(63) Continuation-in-part of application No. 10/031,546, filed as application No. PCT/US00/19864 on Jul. 21, 2000, now abandoned, and a continuation-in-part of application No. 09/839,633, filed on Apr. 20, 2001, now abandoned, which is a continuation-in-part of application No. PCT/US99/26330, filed on Nov. 5, 1999, now abandoned.

(60) Provisional application No. 60/353,552, filed on Feb. 1, 2002, provisional application No. 60/144,904, filed on Jul. 21, 1999, provisional application No. 60/107,256, filed on Nov. 5, 1998.

(51) Int. Cl.
*A61F 2/02*   (2006.01)
*A61L 9/04*   (2006.01)

(52) U.S. Cl. .......................................... 424/423; 424/45

(58) Field of Classification Search ................ 424/423, 424/45
See application file for complete search history.

(56) References Cited

U.S. PATENT DOCUMENTS

| 4,642,120 A | 2/1987  | Nevo et al. |
| 4,808,402 A | 2/1989  | Leibovich et al. |
| 4,872,865 A | 10/1989 | Bloebaum et al. |
| 4,971,955 A | 11/1990 | Soll et al. |
| 5,008,240 A | 4/1991  | Bentz et al. |
| 5,051,443 A | 9/1991  | Neufeld et al. |
| 5,145,841 A | 9/1992  | Cullis-Hill et al. |
| 5,180,812 A | 1/1993  | Dower et al. |

(Continued)

FOREIGN PATENT DOCUMENTS

EP     0 269 408 A2     1/1988

(Continued)

OTHER PUBLICATIONS

Blanco Garcia, F.J., "Catabolic events in osteoarthritic cartilage," *Osteoarthritis and Cartilage* 7:308-309 (1999).

(Continued)

*Primary Examiner*—Carlos A. Azpuru
(74) *Attorney, Agent, or Firm*—Omeros Corporation; Marcia S. Kelbon

(57) ABSTRACT

Methods and compositions for inhibiting articular cartilage degradation. The compositions preferably include multiple chondroprotective agents, including at least one agent that promotes cartilage anabolic activity and at least one agent that inhibits cartilage catabolism. The compositions may also include one or more pain and inflammation inhibitory agents. The compositions may be administered systemically, such as to treat patients at risk of cartilage degradation at multiple joints, and suitably may be formulated in a carrier or delivery vehicle that is targeted to the joints. Alternatively the compositions may be injected or infused directly into the joint.

41 Claims, 9 Drawing Sheets

U.S. PATENT DOCUMENTS

| | | | |
|---|---|---|---|
| 5,206,023 A * | 4/1993 | Hunziker | 424/423 |
| 5,270,300 A | 12/1993 | Hunziker | |
| 5,271,961 A | 12/1993 | Mathiowitz et al. | |
| 5,272,139 A | 12/1993 | Cary, Jr. | |
| 5,288,704 A | 2/1994 | Ungheri et al. | |
| 5,324,775 A | 6/1994 | Rhee et al. | |
| 5,368,858 A | 11/1994 | Hunziker | |
| 5,393,739 A | 2/1995 | Bentz et al. | |
| 5,403,952 A | 4/1995 | Hagmann et al. | |
| 5,411,743 A | 5/1995 | Moore et al. | |
| 5,446,070 A | 8/1995 | Mantelle | |
| 5,449,515 A | 9/1995 | Hamilton et al. | |
| 5,455,268 A | 10/1995 | Watanabe et al. | |
| 5,459,135 A | 10/1995 | Golub et al. | |
| 5,480,901 A | 1/1996 | Baker et al. | |
| 5,502,080 A | 3/1996 | Hitzig | |
| 5,534,254 A | 7/1996 | Huston et al. | |
| 5,541,295 A | 7/1996 | Barrach et al. | |
| 5,591,740 A | 1/1997 | Chipman et al. | |
| 5,605,690 A | 2/1997 | Jacobs et al. | |
| 5,618,563 A | 4/1997 | Berde et al. | |
| 5,667,764 A | 9/1997 | Kopia et al. | |
| 5,667,810 A | 9/1997 | Levin | |
| 5,672,583 A | 9/1997 | Chapman et al. | |
| 5,674,844 A | 10/1997 | Kuberasampath et al. | |
| 5,679,338 A | 10/1997 | Yeh et al. | |
| 5,696,091 A | 12/1997 | York et al. | |
| 5,700,774 A | 12/1997 | Hattersley et al. | |
| 5,747,532 A | 5/1998 | Lai | |
| 5,753,218 A | 5/1998 | Smith et al. | |
| 5,766,585 A | 6/1998 | Evans et al. | |
| 5,767,065 A | 6/1998 | Mosley et al. | |
| 5,800,385 A | 9/1998 | Demopulos et al. | |
| 5,811,535 A | 9/1998 | Adamou et al. | |
| 5,817,305 A | 10/1998 | Hamilton et al. | |
| 5,837,258 A | 11/1998 | Grotendorst | |
| 5,837,846 A | 11/1998 | Huston et al. | |
| 5,843,899 A | 12/1998 | Halloran | |
| 5,858,355 A | 1/1999 | Glorioso et al. | |
| 5,860,950 A | 1/1999 | Demopulos et al. | |
| 5,879,713 A | 3/1999 | Roth et al. | |
| 5,886,026 A | 3/1999 | Hunter et al. | |
| 5,919,634 A | 7/1999 | Eyre | |
| 5,932,207 A | 8/1999 | Schmidt | |
| 5,932,551 A | 8/1999 | Caldwell et al. | |
| 5,948,428 A | 9/1999 | Lee et al. | |
| 5,948,692 A | 9/1999 | Miyauti et al. | |
| 5,972,880 A | 10/1999 | Pelletier et al. | |
| 6,034,062 A | 3/2000 | Thies et al. | |
| 6,075,181 A | 6/2000 | Kucherlapati et al. | |
| 6,083,534 A | 7/2000 | Wallach et al. | |
| 6,083,906 A | 7/2000 | Troutt | |
| 6,090,382 A | 7/2000 | Salfeld et al. | |
| 6,093,743 A | 7/2000 | Lai et al. | |
| 6,096,728 A | 8/2000 | Collins et al. | |
| 6,110,209 A | 8/2000 | Stone | |
| 6,117,425 A | 9/2000 | MacPhee et al. | |
| 6,156,304 A | 12/2000 | Glorioso et al. | |
| 6,159,460 A | 12/2000 | Thompson et al. | |
| 6,159,464 A | 12/2000 | Glorioso et al. | |
| 6,171,787 B1 | 1/2001 | Wiley | |
| 6,180,606 B1 | 1/2001 | Chen et al. | |
| 6,197,325 B1 | 3/2001 | MacPhee et al. | |
| 6,214,049 B1 | 4/2001 | Gayer et al. | |
| 6,235,883 B1 | 5/2001 | Jakobovits et al. | |
| 6,258,562 B1 | 7/2001 | Salfeld et al. | |
| 6,261,279 B1 | 7/2001 | Demopulos et al. | |
| 6,281,195 B1 | 8/2001 | Rueger et al. | |
| 6,306,820 B1 | 10/2001 | Bendele et al. | |
| 6,315,992 B1 | 11/2001 | Noh et al. | |
| 6,344,323 B1 | 2/2002 | Seifert | |
| 6,428,804 B1 | 8/2002 | Suzuki et al. | |
| 6,492,160 B1 | 12/2002 | Griffiths et al. | |
| 6,689,803 B1 | 2/2004 | Hunter | |
| 2001/0055581 A1 | 12/2001 | Tamarkin et al. | |
| 2002/0019369 A1 | 2/2002 | Li et al. | |
| 2002/0102265 A1 | 8/2002 | Hong et al. | |

FOREIGN PATENT DOCUMENTS

| | | |
|---|---|---|
| EP | 0 428 573 B1 | 1/1994 |
| EP | 0 823 478 A3 | 1/1999 |
| EP | 0 500 556 B1 | 1/2001 |
| EP | 1 167 537 A1 | 2/2002 |
| RU | 2112495 | 9/2005 |
| WO | WO 93/04700 | 3/1993 |
| WO | WO/93/04700 * | 3/1993 |
| WO | WO 93/17677 | 9/1993 |
| WO | WO 94/06476 A1 | 3/1994 |
| WO | WO 96/11671 A1 | 4/1996 |
| WO | WO 96/26738 A1 | 9/1996 |
| WO | WO 96/34955 A1 | 11/1996 |
| WO | WO 9824477 A1 | 6/1998 |
| WO | WO 99/08728 | 8/1998 |
| WO | WO 99/26657 | 6/1999 |
| WO | WO 99/62459 A2 | 12/1999 |
| WO | WO 99/65470 A1 | 12/1999 |
| WO | WO 00/48550 | 2/2000 |
| WO | WO 00/04917 | 3/2000 |
| WO | WO 00/23072 | 4/2000 |
| WO | WO 00/23072 A1 | 4/2000 |
| WO | WO 00/25745 A2 | 5/2000 |
| WO | WO 00/56298 A2 | 9/2000 |
| WO | WO 00/62790 A2 | 10/2000 |
| WO | WO 00/73468 A1 | 12/2000 |
| WO | WO 02/00244 | 6/2001 |
| WO | WO 01/47510 A2 | 7/2001 |
| WO | WO 01/87323 A2 | 11/2001 |

OTHER PUBLICATIONS

Henrotin, Y. et al., "Anabolic events in osteoarthritis," *Osteoarthritis and Cartilage* 7:310-312 (1999).

Reuben, S.S., et al. "Postoperative Analgesia for Outpatient Arthroscopic Knee Surgery with Intraarticular Bupivacaine and Keterolac," *Anesth. Analg.* 80:1154-1157 (1995).

Sosnowski, M., et al., "Spinal Administration of Receptor-Selective Drugs as Analgesics: New Horizons," *J. Pain & Symptom Manag.* 5:204-213 (1990).

Pierce, P.A., et al. "Dual Effect of the Serotonin Agonist, Sumatriptan, on Peripheral Neurogenic Inflammation," *Reg. Anesth.* 21:219-225 (1996).

Allen, G.C., et al. "Postarthroscopy Analgesia with Intraarticular Bupivacaine/Morphine: A Randomized Clinical Trial," *Anesthesiology* 79: 475-480 (1993).

Uysalel, A., et al., "Comparison of Intraarticular Bupivacaine with the Addition of Morphine or Fentanyl for Analgesia After Arthroscopic Surgery," *Arthroscopy* 11: 660-663 (1995).

Ruwe, P.A., et al. "The Effect of Intraarticular Injection of Morphine and Bupivacaine on Postarthroscopic Pain Control," *Am. J. Sports Med.* 23:59-64 (1995).

Reuben, S.S., et al. "Postarthroscopic Meniscus Repair Analgesia with Intraarticular Ketorolac or Morphine," *Regional Anes. & Pain Man.* 82:1036-9 (1996).

Tsai, L., et al."Arthroscopic surgery of the knee in local anaesthesia: An analysis of age-related pathology," *Arch. Orthop. Trauma Surg.* 112: 136-138 (1993).

Wredmark, T., et al., "Arthroscopy Under Local Anaesthesia Using Controlled Pressure-Irrigation With Prilocaine," *J. Bone Joint Surg.* 64:583-585 (1982).

Verschure, P.J., et al. "Responsiveness of articular cartilage from normal and inflamed mouse knee joints to various growth factors," *Ann. Rheum. Dis.* 53: 455-460 (1994).

Band, C.J., et al. "Phosphatidylinositol 3'-Kinase and p70$^{s6k}$ Are Required for Insulin but Not Bisperoxovanadium 1,10-Phenanthroline (bpV(phen)) Inhibition of Insulin-like Growth Factor Binding Protein Gene Expression: Evidence for MEK-Independent Activation of Mitogen-Activated Protein Kinase by bpV(phen)," *J. Biol. Chem.* 272:138-145 (1997).

Hardingham,T.E. "Regulation of cartilage matrix synthesis by chondrocytes," *Rev.Rhum.Ed. Fr.* 61:93S-98S (1994).

Huch, K., et al. "Effects Of Recombinant Human Osteogenic Protein 1 On The Production Of Proteoglycan, Prostaglandin $E_2$ And Interleukin-1 Receptor Antagonist By Human Articular Chondrocytes Cultured In The Presence Of Interleukin-1β," *Arthritis & Rheum.* 40:2157-2161 (1997).

Goldring, M.B., "Osteoarthritis and Cartilage: The Role of Cytokines," *Curr. Rheumatol. Rep.* 2:459-465 (2000).

Jorgensen, C., et al. "Interleukin-4 And Interleukin-10 Are Chondroprotective And Decrease Mononuclear Cell Recruitment In Human Rheumatoid Synovium In Vivo," *Immun.* 93:518-523 (1998).

Sugiyama et al. "Interleukin 10 Cooperates With Interleukin 4 To Suppress Inflammatory Cytokine Production By Freshly Prepared Adherent Rheumatoid Synovial Cells," *Journ. of Rheum.* 22:2020-6 (1995).

Van Roon, J.A.G., et al. "Prevention and Reversal of Cartilage Degradation in Rheumatoid Arthritis by Interleukin-10 and Interleukin-4," *Arthritis Rheum.* 39:829-835 (1996).

Hollander, A.P., et al. "Human cartilage is degraded by rheumatoid arthritis synovial fluid but not by recombinant cytokines *in vitro*," *Clin. Exp. Immunol.* 83:52-57 (1991).

Klareskog, L., et al. "Immunopathogenesis and immunotherapy in rheumatoid arthritis: an area in transition," *J. Intern. Med.* 238: 191-206 (1995).

McCarty, M.F., et al. "Niacinamide therapy for osteoarthritis—does it inhibit nitric oxide synthase induction by interleukin 1 in chondrocytes?," *Med. Hypotheses* 53:350-360 (1999) (Abstract Only).

Brittberg, M., et al. "Autologous chondrocyte transplantation," *Clin. Orthop.* 367: S147-S155 (1999) (Abstract Only).

Pelletier, J.P., "The influence of tissue cross-talking on OA progression: role of nonsteroidal antiinflammatory drugs," *Osteoarthritis Cartilage.* 7: 374-376 (1999) (Abstract Only).

Ghosh, Peter. "The Pathobiology of Osteoarthritis and the Rationale for the Use of Pentosan Polysulfate for Its Treatment," *Seminars in Arthritis and Rheumatism* 28:211-267 (1999).

Chambers, M.G., et al. "Chondrocyte cytokine and growth factor expression in murine osteoarthritis," *Osteoarthritis Cartilage* 5: 301-308 (1997) (Abstract Only).

Verschure, P.J., et al. "Articular cartilage destruction in experimental inflammatory arthritis: insulin-like growth factor-1 regulation of proteoglycan metabolism in chondrocytes," *Histochem. J.* 28: 835-857 (1996).

Aigner, T., et al. "Inflammatory cytokine mediated anti-anabolic effects: a potential mechanism in rheumatoid cartilage degeneration," *Verh. Dtsch. Ges. Pathol.* 80: 282-287 (1996) (Abstract Only).

Trippel, S.B., "Growth factor actions on articular cartilage," *J. Rheumatol. Suppl.* 43: 129-132 (1995) (Abstract Only).

Lotz, M., et al. "Cytokine regulation of chondrocyte functions," *J. Rheumatol. Suppl.* 43: 104-108 (1995) (Abstract Only).

Homandberg, G.A., et al. "High concentrations of fibronectin fragments cause short-term catabolic effects in cartilage tissue while lower concentrations cause continuous anabolic effects," *Arch. Biochem. Biophys.* 311: 213-218 (1994) (Abstract Only).

Sah, R.L., et al. "Differential effects of bFGF and IGF-I on matrix metabolism in calf and adult bovine cartilage explants," *Arch. Biochem. Biophys.* 308: 137-147 (1994) (Abstract Only).

Mohamed-Ali, H. "Proteolytic enzymes and the destruction of articular cartilage in arthritis and chronic polyarthritis," *Wien. Med. Wochenschr.* 141: 77-85 (1991) (Abstract Only).

Venn, G., et al., "Effects of catabolic and anabolic cytokines on proteoglycan biosynthesis in young, old and osteoarthritic canine cartilage," *Biochemical Society Transactions*, vol. 18, pp. 973-974, 1990.

Lanzer, W.L., et al. "Changes in articular cartilage after meniscectomy," *Clin. Orthop.* 252: 41-48 (1990) (Abstract Only).

Herman, J.H., et al. "Immunologic modulation of cartilage metabolism," *J. Rheumatol.* 14: 83-85 (1987) (Abstract Only).

Hess, E.V., et al. "Cartilage metabolism and anti-inflammatory drugs in osteoarthritis," *Am. J. Med.* 81: 36-43 (1986) (Abstract Only).

Vidal y Plana, R.R., et al. "Glucosamine: its importance for the metabolism of articular cartilage. 2. Studies on articular cartilage," *Fortschr. Med.* 98: 801-806 (1980) (Abstract Only).

Shalom-Barak, T., et al. "Interleukin-17-induced Gene Expression in Articular Chondrocytes is Associated with Activation of Mitogen-activated Protein Kinases and NF-κB," *J. Biol. Chem.* 273: 27467-27473 (1998).

Tardif, G., et al. "Collagenase 3 production by human osteoarthritic chondrocytes in response to growth factors and cytokines is a function of the physiologic state of the cells," *Arthritis Rheum.* 42: 1147-1158 (1999) (Abstract Only).

Dingle, J.T. "Cartilage Maintenance in Osteoarthritis: Interaction of Cytokines, NSAID and Prostaglandins In Articular Cartilage Damage and Repair," *J. Rheumatol. Suppl.* 28: 30-37 (1991).

Attur, M.G., et al. "Tetracycline Up-Regulates COX-2 Expression and Prostaglandin $E_2$ Production Independent of its Effect on Nitric Oxide," *J. Immunol.* 162:3160-3167 (1999).

Blanco, F.J., et al. "Chondrocyte apoptosis induced by nitric oxide," *Am. J. Pathol.* 146: 75-85 (1995) (Abstract only).

Attur, M.G., et al. "Autocrine Production of IL-1 β by Human Osteoarthritis-Affected Cartilage and Differential Regulation of Endogenous Nitric Oxide, IL-6, Prostaglandin $E_2$, and IL-8," *Proc. Assoc. Am. Physicians* 110: 65-72 (1998).

Lubberts, E. et al. "Reduction of Interleukin-17-Induced Inhibition of Chrondrocyte Proteoglycan Synthesis in Intact Murine Articular Cartilage by Interleukin-4," *Arthritis Rheum.* 43: 1300-1306 (2000).

Martel-Pelletier, J., et al. "Mitogen-activated protein kinase and nuclear factor κB together regulate interleukin-17-induced nitric oxide production in human osteoarthritic chondrocytes: possible role of transactivating factor mitogen-activated protein kinase-activated proten [sic] kinase (MAPKAPK)," *Arthritis Rheum.* 42: 2399-2409 (1999) (Abstract only).

Agro, A., et al. "Prostaglandin E2 enhances interleukin 8 (IL-8) and IL-6 but inhibits GMCSF production by IL-1 stimulated human synovial fibroblasts in vitro," *J. Rheumatol.* 23: 862-868 (1996) (Abstract only).

Kawamura, M., et al. "Growth factors, mitogens, cytokines, and bone morphogenetic protein in induced chondrogenesis in tissue culture," *Dev. Biol.* 130: 435-442 (1988) (Abstract only).

Chandrasekhar, S., et al. "Degradative and repair responses of cartilage to cytokines and growth factors occur via distinct pathways," *Agents Actions Suppl.* 39: 121-125 (1993) (Abstract only).

Harvey, A., et al. "Differential modulation of degradative and repair responses of interleukin-1-treated chondrocytes by platelet-derived growth factor," *Biochem. J.* 292: 129-136 (1993) (Abstract only).

Stevens, P., et al. "Synergism of basic fibroblast growth factor and interleukin-1 beta to induce articular cartilage-degradation in the rabbit," *Agents Actions* 34: 217-219 (1991) (Abstract only).

Chandrasekhar, S., et al. "Differential regulation of metalloprotease steady-state mRNA levels by IL-1 and FGF in rabbit articular chondrocytes," *FEBS Lett.* 296: 195-200 (1992) (Abstract only).

Van Der Kraan, P., et al. "Role of nitric oxide in the inhibition of BMP-2-mediated stimulation of proteoglycan synthesis in articular cartilage," *Osteoarthritis Cartilage* 8: 82-86 (2000).

Glasser, R.S., et al., "The Perioperative Use Of Corticosteroids And Bupivacaine In The Management Of Lumbar Disc Disease," *J. Neurosurg.* 78: 383-387 (1993).

Van den Berg, W.B., et al. "Tissue Engineering, Cells, Scaffolds, and Growth Factors: Growth factors and cartilage repair," *Clin. Orthop.* 391S:S244-50 (2001).

Rogachefsky, R.A., et al. "Treatment Of Canine Osteoarthritis With Insulin-Like Growth Factor-1 (IGF-1) And Sodium Pentosan Polysulfate," *Osteoarthritis & Cartilage* 1:105-14 (1993).

Goldring, M.B., et al., "Etodolac Preserves Cartilage-Specific Phenotype in Human Chondrocytes: Effects On Type II Collagen Synthesis and Associated mRNA Levels," *Euro. J. Rheum. & Inflamm.* 10:10-21 (1990).

Itayem, R., et al. "Ultrastructural Studies On The Effect Of Transforming Growth Factor-β1 On Rat Articular Cartilage," *APMIS* 105:221-8 (1997).

Bhargava, M.M. et al. "The Effect Of Cytokines On The Proliferation And Migration Of Bovine Meniscal Cells," *Am. Jour. Sports Med.* 27:636-43 (1999).

Goldring, M.B. "Anticytokine therapy for osteoarthritis," *Expert. Opin. Biol. Ther.* 1:817-829 (2001).

Goldring, M.B. "The Role of the Chondrocyte in Osteoarthritis," *Arthritis and Rheumatology* 43:1916-1926 (2000).

Goldring, M.B., "The role Ctokines as Inflammatory Mediators in Osteoarthritis: Lessons from Animal Models," *Connective Tissue Research*, 40:1-11 (1999).

Nasatzky, E., et al. "Parathyroid Hormone And Transforming Growth Factor-β1 Coregulate Chondrocyte Differentation *In Vitro*," *Endocrine* 13:305-13 (2000) (Abstract Only).

Heiner, John P. "Bone Formation Within Acetabular Defects In Total Hip Arthroplasty," *Citations from Federal Research in Progress (FRP)* FRP 02-01 128953, NDN-049-0233-4208-2, date unknown.

Cook, T.M., et al. "Postarthroscopic Meniscus Repair Analgesia with Intraarticular Ketorolac or Morphine," *Anesth. Analg.* 84:466-467 (1997).

Frisbie, D.D., et al. "Metabolic And Mitogenic Activities Of Insulin-Like Growth Factor-1 In Interleukin-1-Conditioned Equine Cartilage," *Am. J. Vet. Res.* 61:436-441 (2000).

Frisbie, D.D., et al. "Treatment Of Experimental Equine Osteoarthritis By *In Vivo* Delivery Of The Equine Interleukin-1 Receptor Antagonist Gene," *Gene Ther.* 9:12-20 (2002).

Gatt, C.J., et al. "Preemptive Analgesia: Its Role and Efficacy in Anterior Cruciate Ligament Reconstruction," *Am. J. Sports Med.* 26: 524-529 (1998).

Dingle, J.T. "The Effects of NSAID on the Matrix of Human Articular Cartilages," *Z. Rheumatol.* 58:125-129 (1999).

Horisawa, E., et al., "Prolonged Anti-Inflammatory Action of DL-Lactide/Glycolide Copolymer Nanospheres Containing Betamethasone Sodium Phosphate for an Intra-Articlular Delivery System in Antigen-Induced Arthritic Rabbit," *Pharmaceutical Research*, 19(4):403-410 (2002).

Kolettas, E., et al., "Chondrocyte phenotype and cell survival are regulated by culture conditions and by specific cytokines through the expression of Sox-9 transcription factor," *Rheumatology*, 40:1146-1156 (2001).

Ghosh, P., et al. "Interactions of Pentosan Polysulfate with Cartilage Matrix Proteins and Synovial Fibroblasts Derived from Patients with Osteoarthritis," *Osteoarthritis and Cartilage* 4:43-53 (1996).

Kalbhen, D.A. "Pharmacological Studies on the Anti-Inflammatory Effect of a Semi-Synthetic Polysaccharide," *Pharmacology* 9:74-79 (1973).

Read, R.A., et al. "Systemic Use of Pentosan Polysulphate in the Treatment of Osteoarthritis," *Journal of Small Animal Practice* 37:108-114 (1996).

Verbruggen, G., et al. "Intra-Articular Injection of Pentosanpolysulphate Results in Increased Hyaluronan Molecular Weight in Joint Fluid," *Clinical and Experimental Rheumatology* 10:249-254 (1992).

Munteanu, S., et al. "Calcium Pentosan Polysulfate Inhibits the Catabolism of Aggrecan in Articular Cartilage Explant Cultures," *Arthritis & Rheumatism* 43:2211-2218 (2000).

Riass, R., et al. "Chondrocytes and Antirheumatic Drugs," *The Journal of Rheumatology* 22: 152-154 (1995).

Ghosh, P., et al. "Osteoarthritis Genetic and Molecular Mechanisms," *Biogerontology* 3:85-88 (2002).

Smith, M., et al. "The Effects of Orally Administered Calcium Pentosan Polysulfate on Inflammation and Cartilage Degradation Produced in Rabbit Joints by Intraarticular Injection of a Hyaluronate-Polylysine Complex," *Arthritis & Rheumatism* 37: 125-136 (1994).

Ghosh, P., et al. "Chondroprotection, Myth or Reality: An Experimental Approach," *Seminars in Arthritis and Rheumatism* 19:3-9 (1990).

Ghosh, P., et al. "Animal Models of Early Osteoarthritis: Their Use for the Evaluation of Potential Chondroprotective Agents," in *Joint Destruction in Arthritis and Osteoarthritis* 195-206 (1993).

Kongtawelert, P., et al. "Pentosan Polysulfate (Cartrophen®) Prevents the Hydrocortisone Induced Loss of Hyalurconic Acid and Proteoglycans from Cartilage of Rabbit Joints as Well as Normalizes the Keratan Sulfate Levels in Their Serum," *The Journal of Rheumatology* 16:1454-1459 (1989).

Costeseque, R., et al. "Polysulphated Polysaccharides: an In Vitro Study of their Effects on Proteoglycan Biosynthesis by Articular Chondrocytes," *Arch. Int. Pharmacodyn.* 282:196-208 (1986).

Kalbhen D.A. "Pharmakologische Beurteilung von Möglichkeiten einer Knorpelschutztherapie bei degenerativen Gelenkerkrankungen (Arthrosen)," *Z. Rheumatol.* 42:187-194 (1983).

Grumbles, R., et al. "Cartilage Metalloproteases in Disuse Atrophy," *The Journal of Rheumatology* 22:146-148 (1995).

Burton-Wurster, N., et al. "Accumulation of Fibrinectin in Articular Cartilage Explants Cultured with TGFβ1 and Fucoidan," *Archives of Biochemistry and Biophysics* 316:452-460 (1995).

Sadhukhan, P., et al. "Sodium Pentosan Polysulfate Reduces Urothelial Responses to Inflammatory Stimuli via an Indirect Mechanism," *The Journal of Urology* 168:289-292 (2002).

Collier, S., et al. "Evaluation of the effect of antiarthritic drugs on the secretion of proteoglycans by lapine chondrocytes using a novel assay procedure," *Ann. Rheum. Dis.* 48:372-381 (1989).

Firestein, G.S., et al., "Anticytokine Therapy in Rheumatoid Arthritis," *N. Engl. J. Med.* 337:195-197 (1997).

Talu, G.K., et al., "Comparison of efficacy of intraarticular application of tenoxicam, bupivacaine and tenoxicam: bupivacaine combination in arthroscopic knee surgery," *Knee Surg. Sports Traumatol. Arthrosc.*, 6:355-60 (2002).

Muller-Ladner, U., "Gene Transfer of Cytokine Inhibitors Into Human Synovial Fibroblasts in the SCID Mouse Model," *Arthritis & Rheumatism*, 42(3):490-497 (1999).

Osborn, K.E., et al., "Growth Factor Stimulation of Adult Articular Cartilage," *Journal of Orthopaedic Research*, 7:35-42 (1989).

McQuillan, D.J., et al., "Stimulation of proteoglycan biosynthesis by serum and insulin-like growth factor-I in cultured bovine articular cartilage," *Biochem. J.*, 240:423-430 (1986).

Garnero, P., et al., "Molecular Basis and Clinical Use of Biochemical Markers of Bone, Cartilage, and Synovium in Joint Diseases", *Arthritis & Rheumatism*, 43(5):953-968 (2000).

Abbaszade, I., et al., "Cloning and Characterization of *ADAMTS11*, an Aggrecanase from the ADAMTS Family*," *The Journal of Biological Chemistry*, 274 (33):23443-23450 (1999). *advertisement.

Billinghurst, R.C., et al., "Enhanced Cleavage of Type II Collagen by Collagenases in Osteoarthritic Articular Cartilage," *J. Clin. Invest.*, 99(7):1534-1545 (1997).

Huebner, J.L., et al., "Collegenase 1 and Collegenase 3 Expression in a Guinea Pig Model of Osteoarthritis," *Arthritis & Rheumatism*, 41(5):877-890 (1998).

Barrera, P., et al., "Effects of treatment with a fully human anti-tumour necrosis factor α monoclonal antibody on the local and systemic homeostasis of interleukin 1 and TNFα in patients with rheumatoid arthritis," *Ann. Rheum. Dis.*, 60:660-669 (2000).

Taylor, P.C., "Anti-tumor necrosis factor therapies," *Current Opinion in Rheumatology*, 13:164-169 (2001).

Fautrel, B. et al., "Interet des molecules anti-TNF-α dans le maladies inflammatoires et infectieuses," *Rev. Med. Interne*, 21:872-88 (2000).

Moghimi, S.M., et al., "Long-Circulating and Target-Specific Nanoparticles: Theory to Practice," *Pharmacological Reviews*, 53(2):283-318 (2001).

DeAngelis, A.P., "Accumulation of fibrinogen-coated microparticles at fibrin(ogen)-rich inflammatory site," *Biotechnol. Appl. Biochem.*, 29:251-261 (1999).

ImmunoGen Website, http://www.immunogen.com/tech_ovr.html, (2002).

Eniola, A.O., et al., "Characterization of biodegradable drug delivery vehicles with the adhesive properties of leukocytes," *Biomaterials*, 23(10):2167-77 (2002). (Abstract only).

Corvo, M.L., et al., "Subcutaneous Administration of Superoxide Dismutese Entrapped in Long Circulating Liposomes: In Vivo Fate and Therapeutic Activity in an Inflammation Model," *Pharmaceutical Research*, 17(5):600-606 (2000).

Breslau, Karen, "Tiny Weapons with Giant Potential," *Newsweek*, Jun. 24, 2002.

Mathur, P., "Preparation Parameters and Release Characterization of Microspheres and Nanospheres Containing Coumarin-6, Insulin and Insulin-Like Growth Factor-I," Master's Thesis, Hamdard University, India, Dec., 2002.

Kafienah, W., et al, "Human cathepsin K cleaves native type I and II collagens at the N-terminal end of the triple helix," *Biochem. J.*, 331:727-732 (1998).

Tang, B.L., and Hong, W., "ADAMTS: A novel family of proteases with an ADAM protease domain and thrombospondin 1 repeats," *Federation of European Biochemical Societies*, 445:223-225(1999).

Tortorella, M.D., et al., "Sites of Aggrecan Cleavage by Recombinant Human Aggrecanase-1 (ADAMTS-4)*,", *The Journal of Biological Chemistry*, 275(24):18566-18573 (2000). *advertisement.

Tortorella, M.D., et al., "The Thrombospondin Motif of Aggrecanase-1 (ADAMTS-4) Is Critical for Aggrecan Substrate Recognition and Cleavage*," *The Journal of Biological Chemistry*, 275(33):25791-25797 (2000). *advertisement.

Schrappe, M., et al., "Correlation of Chondroitin Sulfate Proteoglycan Expression on Proliferating Brain Capillary Endothelial Cells with the Malignant Phenotype of Astroglial Cells," *Cancer Research*, 51:4986-4993, (1991).

Schrappe, M., et al., "Long-Term Growth Suppression of Human Glioma Xenografts by Chemoimmunoconjugates of 4-Desacetylvinblastine-3-carboxyhydrazide and Monoclonal Antibody 9.2.27," *Cancer Research*, 52:3838-3844 (1992).

Wilkins, B.S., et al., "Immunohistochemical characterization of intact stromal layers in long-term cultures of human bone marrow," *British Journal of Haematology*, 90:757-766 (1995).

Glant, T.T., et al., "Appearance and persistence of fibronectin in cartilage: Specific interaction of fibronectin with collagen type II," *Histochemistry*, 82:149-158 (1985).

Miller, E.J., "Structural Studies on Cartilage Collagen Employing Limited Cleavage and Solubilization with Pepsin," *Biochemistry* 11:4903-4909 (1972).

Linsenmayer, T.F., et al., "Monoclonal Antibodies to Connective Tissue Macromolecules: Type II Collagen ," *Biochemical and Biophysical Research Communications*, 92(2):440-446 (1980).

Kafienah, W., et al., "Three-Dimensional Tissue Engineering of Hyaline Cartilage: Comparison of Adult Nasal and Articular Chondrocytes," *Tissue Engineering*, 8(5):817-826 (2002).

Freed, L.E., et al., "Chondrogenesis in Cell-Polymer-Bioreactor System," *Experimental Cell Research*, 240:58-65 (1998).

Hollander, A.P., et al., "Increased Damage to Type II Collagen in Osteoarthritic Articular Cartilage Detected by a New Immunoassay," *J. Clin. Invest.*, 93:1722-1732 (1994).

Morgan, Jr., A.C., et al., "Production and Characterization of Monoclonal Antibody to a Melanoma Specific Glycoprotein," *Hybridoma*, 1(1):27-36 (1981).

Blanco, F. J., et al., "IL-1-Induced Nitric Oxide Inhibits Chondrocyte Proliferation via PGE2," *Experimental Cell Research* 218:319-325 (1995).

\* cited by examiner

Fig. 1  CHONDROCYTE CELL MOLECULAR TARGETS & SIGNALING INFORMATION

Fig. 2   SYNOVIOCYTE CELL MOLECULAR TARGETS & SIGNALING INFORMATION

Fig. 3  COMMON SIGNALING PATHWAYS IN CHONDROCYTE/SYNOVIOCYTE CELLS

Fig. 4    MOLECULAR SITES OF ACTION IN CHONDROPROTECTIVE SOLUTION

Fig. 5  ANABOLIC CHONDROPROTECTIVE MOLECULAR TARGETS ON SYNOVIOCYTES AND/OR CHONDROCYTES

Fig. 6  CATABOLIC CHONDROPROTECTIVE MOLECULAR TARGETS ON SYNOVIOCYTES AND/OR CHONDROCYTES

COMPOSITIONS AND METHODS FOR SYSTEMIC INHIBITION OF CARTILAGE DEGRADATION

CROSS-REFERENCE TO RELATED APPLICATIONS

The present application claims priority from U.S. Provisional Application No. 60/353,552 filed Feb. 1, 2002 and is a continuation-in-part of U.S. application Ser. No. 10/031,546 filed Jan. 18, 2002, which is a U.S. National phase of International Application No. PCT/US00/19864 filed Jul. 21, 2000 designating the United States, now abandoned, which claims priority from U.S. Provisional Application No. 60/144,904 filed Jul. 21, 1999, and also is a continuation-in-part of U.S. application Ser. No. 09/839,633 filed Apr. 20, 2001, which is a continuation-in-part of International Application No. PCT/US99/26330 filed Nov. 5, 1999 designating the United States, now abandoned, which claims priority from U.S. Provisional Application No. 60/107,256 filed Nov. 5, 1998, and of International Application No. PCT/US99/24625 filed Oct. 20, 1999 designating the United States, now abandoned, which claims priority from U.S. Provisional Application No. 60/105,026 filed Oct. 20, 1998, the benefits of the priority of which are hereby claimed under 35 USC Sections 119(e) and 120.

FIELD OF THE INVENTION

The present invention relates to therapeutic compositions and methods for the protection of articular cartilage.

BACKGROUND OF THE INVENTION

Diseases and conditions that cause the destruction of cartilage within the joints poses a significant public health concern, particularly in view of the demographics of an aging population. The articular cartilage of the joint represents a complex system of many different molecules. Multiple mechanisms are involved in the degradation of articular cartilage in arthritides such as rheumatoid arthritis (RA) and osteoarthritis (OA). OA, a non-inflammatory arthritis, is the most common form of joint disease, and is second only to cardiovascular disease as a cause of early retirement and disability. Some individuals exhibit OA in a single or limited number of joints, such as may result from traumatic injury due to accident or surgery. Many other individuals suffer from OA in multiple joints due to wear and tear associated with aging or with athletic or occupational activity over an extended period of time. RA is the most common form of inflammatory arthritis, affecting 3% of women and 1% of men. The majority of RA patients have symptoms in multiple joints, especially the small joints of the hand, the elbows, the wrists and the shoulders.

The destruction of hyaline articular cartilage is the hallmark of OA and disabling RA. Although various therapeutic approaches may provide relief of symptoms, no therapeutic regimen has been proven to retard progression of articular cartilage degradation. The progressive deterioration and loss of articular cartilage leads to an irreversible impairment of joint motion. These changes in cartilage are the final pathogenic events that are common to osteoarthritis (OA) and rheumatoid arthritis (RA).

Cartilage destructive processes may also be associated with or initiated by surgical procedures of the joint. Arthroscopy is a surgical procedure in which a camera, attached to a remote light source and video monitor, is inserted into an anatomic joint (e.g., knee, shoulder, etc.) through a small portal incision in the overlying skin and joint capsule. Through similar portal incisions, surgical instruments may be placed in the joint, their use guided by arthroscopic visualization. As arthroscopists' skills have improved, an increasing number of operative procedures, once performed by "open" surgical technique, now can be accomplished arthroscopically. Such procedures include, for example, partial meniscectomies and ligament reconstructions in the knee, shoulder acromioplasties and rotator cuff debridements and elbow synovectomies. As a result of widening surgical indications and the development of small diameter arthroscopes, wrist and ankle arthroscopies also have become routine.

Throughout each arthroscopy, physiologic irrigation fluid (e.g., normal saline or lactated Ringer's) is flushed continuously through the joint, distending the joint capsule and removing operative debris, thereby providing clearer intra-articular visualization. U.S. Pat. No. 4,504,493 to Marshall discloses an isomolar solution of glycerol in water for a non-conductive and optically clear irrigation solution for arthroscopy. Conventional physiologic irrigation fluids do not provide analgesic, anti-inflammatory or anti-cartilage degradation effects.

SUMMARY OF THE INVENTION

The present invention provides methods and compositions for reducing or preventing destruction of articular cartilage in a joint, by administering a combination of two or more metabolically active chondroprotective agents. Metabolically active agents include, but are not limited to, compounds that act directly or indirectly to modulate or alter the biological, biochemical or biophysical state of a cell, including agents that alter the electrical potential of the plasma membrane, the ligand binding or enzymatic activity of cellular receptors, intracellular or extracellularly located enzymes, protein-protein interactions, RNA-protein interactions, or DNA-protein interactions. In one aspect of the present invention pharmaceutical compositions of metabolically active chondroprotective agents are provided that are based upon a combination of at least two agents that act simultaneously on distinct molecular targets.

Representative chondroprotective agents include, for example: (1) antagonists of receptors for the interleukin-1 family of proteins, including, for example, IL-1β, IL-17 and IL-18; (2) antagonists of the tumor necrosis factor (TNF) receptor family, including, for example, TNF-R1; (3) agonists for interleukin 4, 10 and 13 receptors; (4) agonists for the TGF-β receptor superfamily, including, for example, BMP-2, BMP-4 and BMP-7; (5) inhibitors of COX-2; (6) inhibitors of the MAP kinase family, including, for example, p38 MAP kinase; (7) inhibitors of the matrix metalloproteinases (MMP) family of proteins, including, for example, MMP-3 and MMP-9; (8) inhibitors of the NF-κB family of proteins, including, for example, the p50/p65 dimer complex with IκB; (9) inhibitors of the nitric oxide synthase (NOS) family, including, for example, iNOS; (10) agonists and antagonists of integrin receptors, including, for example, agonists of $\alpha_V\beta_3$ integrin; (11) inhibitors of the protein kinase C (PKC) family; (12) inhibitors of the protein tyrosine kinase family, including, for example, the src subfamily; (13) modulators of protein tyrosine phosphatases; and (14) inhibitors of protein src homology 2 (SH2) domains. Additional chondroprotective agents include other growth factors, such as by way of example insulin-like growth factors (e.g., IGF-1) and fibroblast growth factors (e.g., bFGF).

In a preferred embodiment, at least one agent is a cytokine or growth factor receptor agonist that directly provides anti-inflammatory activity and/or promotes cartilage anabolic processes, also referenced herein as an "anabolic agent," and at least a second agent is a receptor antagonist or enzyme inhibitor that acts to inhibit cartilage catabolic processes and that may also inhibit pro-inflammatory processes, also referenced herein as an "inhibitor of cartilage catabolism" or "catabolic inhibitory agent". As used herein, the term "chondroprotective agents" is intended to include both anabolic agents and inhibitors of cartilage catabolism.

In this embodiment of the invention, at least a first chondroprotective agent is an anti-inflammatory/anabolic cytokine, which act functionally to suppress the role of pro-inflammatory cytokines in the joint, promote cartilage matrix synthesis and inhibit matrix degradation. These receptor agonists include, for example, specific anti-inflammatory and anabolic cytokines, such as the interleukin (IL) agonists (e.g., IL-4, IL-10 and IL-13) and specific members of the transforming growth factor-β superfamily (e.g., TGFβ and BMP-7), insulin-like growth factors (e.g., IGF-1) and fibroblast growth factors (e.g., bFGF). At least a second chondroprotective agent is drawn from a class of cartilage catabolic inhibitors that include receptor antagonists or enzyme inhibitors that acts to inhibit and reduce the activity or the expression of a pro-inflammatory molecular target (e.g., the IL-1 receptor antagonists, TNF-α receptor antagonists, cyclooxygenase-2 inhibitors, MAP kinase inhibitors, nitric oxide synthase (NOS) inhibitors, and nuclear factor kappaB (NFκB) inhibitors). The second chondroprotective agent may also be selected from inhibitors of matrix metalloproteinases that inhibit cartilage catabolism, cell adhesion molecules, including integrin agonists and integrin antagonists, that inhibit cartilage catabolism, intracellular signaling inhibitors, including protein kinase C inhibitors and protein tyrosine kinase inhibitors, that inhibit cartilage catabolism, and inhibitors of SH2 domains that inhibit cartilage catabolism.

Articular cartilage is a specialized extracellular matrix that is produced and maintained by metabolically active articular chondrocytes. The maintenance of a normal, healthy extracellular matrix reflects a dynamic balance between the rate of biosynthesis and incorporation of matrix components, and the rate of their degradation and subsequent loss from the cartilage into the synovial fluid. While the regulatory mechanisms that underlie the matrix homeostasis are not well understood, they are clearly altered in inflammatory joint diseases and in response to joint trauma such that the rate of matrix breakdown exceeds the rate of new synthesis of matrix components. Matrix homeostasis is generally regarded to represent a dynamic balance between the effects of catabolic cytokines and anabolic cytokines (including growth factors). The optimal combination of therapeutic agents useful for cartilage protection shifts the dynamic matrix equilibrium through accelerating the synthetic rate and simultaneously inhibiting the rate of breakdown, thus maximizing anabolic processes and promoting repair.

Catabolic cytokines, such as IL-1β and TNF-α act at specific receptors on chondrocytes to induce production of MMPs that induce matrix degradation while the degradation is inhibited by anabolic cytokines such as TGF-β, BMP-2 and IGF-1. Hence, a therapeutic approach that is based only upon inhibiting catabolic processes (such as a combination of an MMP inhibitor and an IL-1 antagonist) is not optimal for cartilage repair since anabolic agents are needed to induce or accelerate biosynthesis and assembly of components for matrix production. Secondly, the multiplicity of catabolic cytokines (IL-1, TNF, IL-17, IL-18, LIF) that contribute to cartilage matrix destruction indicate it will not be practical to block all the catabolic cytokine activity. Conversely, an approach that relies only upon use of anabolic agents, such as IGF-1, BMP-2 or BMP-7, is not optimal since it does not address the counter-regulatory role of the catabolic cytokines. TGF-β, BMP-2 and IGF-1 also act at specific receptors to induce chondrocytes to produce matrix components, which is inhibited by IL-1β, TNF-α, IL-17 and LIF. Therefore, the optimal therapeutic combination for chondroprotection is believed to be composed of at least one anabolic agent and one inhibitor of cartilage catabolism.

In one aspect of the present invention, a plurality of chondroprotective agents are administered via a systemic route to a patient at risk of articular cartilage degradation. The plurality of agents that are administered systemically include at least one agent that promotes cartilage anabolic activity and at least one agent that inhibits cartilage catabolism. Each agent is included in a sufficient amount to provide a combination that is therapeutically effective when the solution is delivered to the joint of a patient to both inhibit cartilage catabolic processes and to promote cartilage anabolic processes. Additionally, one or more agents that act to inhibit pain and/or inflammation may be administered with the chondroprotective agents. Systemic administration of the plurality of chondroprotective agents may be preferred when a patient is at risk of cartilage degradation, or suffers from degenerative disease, at multiple joints simultaneously.

In order to minimize adverse or unwanted systemic effects, in one aspect of a systemically delivered embodiment of the invention, a therapeutic strategy is to deliver the combination of agents in a carrier or delivery vehicle that is targeted to the joint. In a preferred targeted embodiment, the at least one anabolic chondroprotective agent and/or the at least one catabolic inhibitory chondroprotective agent, and preferably both the anabolic and catabolic inhibitory chondroprotective agents, may be encapsulated within a delivery vehicle, such as a nanosphere. A targeting antibody or antibody fragment is coupled to the nanosphere. The antibody or antibody fragment is specific to a targeted antigenic determinant that is localized within the joint. A therapeutic method of the present invention includes systemically administering this targeted, encapsulated composition of one or more chondroprotective agents to a patient at risk of cartilage degradation, preferably by intravascular, intramuscular, subcutaneous or inhalational administration.

In a further aspect of the present invention, compositions for systemic administration are provided that include a plurality of chondroprotective agents, including at least one agent that promotes cartilage anabolic activity and at least one agent that inhibits cartilage catabolism. Additionally, one or more agents that act to inhibit pain and/or inflammation may be included in the compositions. All agents are included at a dosage sufficient to provide a cartilage protective therapeutic effect at a joint or joints when administered systemically. Methods of manufacturing a medicament including such a composition for use in treating a patient at risk of cartilage degradation are also provided.

In order to target such systemically administered compositions to the joint, the at least one anabolic chondroprotective agent and/or the at least one catabolic inhibitory chondroprotective agent, and preferably both the anabolic and catabolic inhibitory chondroprotective agents, are encapsulated within a delivery vehicle, such as a nanosphere, to which is coupled an antibody or antibody fragment that is specific to an antigenic determinant that is localized within the joint. A method is also provided for manufacturing such a medicament including an encapsulated chondroprotective agent(s) coupled to an antibody or antibody fragment, such antibody or antibody fragment being targeted to an antigenic determinant that is localized within the joint, for use in treating a patient at risk of cartilage degradation.

In a different aspect of the invention, a composition which includes one or preferably multiple metabolically active chondroprotective agents together with one or more agents for the inhibition of pain, inflammation, or the like, or more preferably a multiple agent combination of anabolic agents and inhibitors of catabolism, in a pharmaceutically effective carrier may be prepared for intra-articular delivery directly to the joint of a patient. While systemic delivery of the chondroprotective compositions of the present invention may be preferred for diseases or conditions affecting multiple joints, local delivery of the compositions of the present invention may be preferred in other instances. Such instances may include the treatment of patients with a cartilage degenerative condition or diseases affecting only a single or limited number of joints, periprocedural administration associated with an operative or interventional procedure at a joint, or in instances where undesirable side effects may be associated with systemic administration. In this local delivery aspect of the invention, such compositions are delivered locally by intra-articular injection (including for the treatment of cartilage degenerative diseases such as osteoarthritis or rheumatoid arthritis) or via infusion, including administration periprocedurally (i.e., preoperatively and/or intraoperatively and/or postoperatively) during surgical arthroscopic procedures.

This local delivery aspect of the present invention provides a solution constituting a mixture of multiple agents in low concentrations directed at inhibiting locally the mediators of pain, inflammation, and cartilage degradation in a physiologic electrolyte carrier fluid. The invention also provides a method for perioperative delivery of the irrigation solution containing these agents directly to a surgical site, where it works locally at the receptor and enzyme levels to preemptively limit pain, inflammation, and cartilage degradation at the site. Due to the local perioperative delivery method of the present invention, a desired therapeutic effect can be achieved with lower doses of agents than are necessary when employing other methods of delivery (i.e., intravenous, intramuscular, subcutaneous and oral).

The anti-pain and/or anti-inflammation agents and/or anti-cartilage degradation agents in the solution include agents selected from multiple classes of receptor antagonists and agonists and enzyme activators and inhibitors, each class acting through a differing molecular mechanism of action for pain- and/or inflammation inhibition and/or cartilage degradation.

In addition to the anti-cartilage degradation agent(s), the compositions of the inventions may include anti-pain and/or anti-inflammation agents. Representative agents for the inhibition of pain and/or inflammation include, for example: (1) serotonin receptor antagonists; (2) serotonin receptor agonists; (3) histamine receptor antagonists; (4) bradykinin receptor antagonists; (5) kallikrein inhibitors; (6) tachykinin receptor antagonists, including neurokinin$_1$ and neurokinin$_2$ receptor subtype antagonists; (7) calcitonin gene-related peptide (CGRP) receptor antagonists; (8) interleukin receptor antagonists; (9) inhibitors of enzymes active in the synthetic pathway for arachidonic acid metabolites, including (a) phospholipase inhibitors, including PLA$_2$ isoform inhibitors and PLC isoform inhibitors, (b) cyclooxygenase inhibitors, and (c) lipooxygenase inhibitors; (10) prostanoid receptor antagonists including eicosanoid EP-1 and EP-4 receptor subtype antagonists and thromboxane receptor subtype antagonists; (11) leukotriene receptor antagonists including leukotriene B$_4$ receptor subtype antagonists and leukotriene D$_4$ receptor subtype antagonists; (12) opioid receptor agonists, including μ-opioid, δ-opioid, and κ-opioid receptor subtype agonists; (13) purinoceptor antagonists including P$_{2X}$ receptor antagonists and P$_{2Y}$ receptor antagonists; and (14) calcium channel antagonists. Each of the above agents functions either as an anti-inflammatory agent and/or as an anti-nociceptive (i.e., anti-pain or analgesic) agent. The selection of agents from these classes of compounds is tailored for the particular application.

The present invention also provides a method for manufacturing a medicament compounded in one aspect of the invention as a dilute irrigation solution for use in continuously irrigating an operative site, typically at the site of a joint of a patient, during an arthroscopic operative procedure. In this local delivery embodiment of the invention, the method entails dissolving in a physiologic electrolyte carrier fluid at least one anti-cartilage degradation agent and preferably one or more anti-pain/anti-inflammatory agents, and for some applications anti-cartilage degradation agents, each agent included at a concentration of preferably no more than about 100,000 nanomolar, more preferably no more than about 25,000 nanomolar, and most preferably no more than about 10,000 nanomolar.

A method of the local delivery aspect of the present invention provides for the delivery of a dilute combination of multiple receptor antagonists and agonists and enzyme inhibitors and activators directly to a wound or operative site, during therapeutic or diagnostic procedures for the inhibition of cartilage degradation, pain, and/or inflammation. Since the active ingredients in the solution are being locally applied directly to the operative tissues in a continuous fashion, the drugs may be used efficaciously at extremely low doses relative to those doses required for therapeutic effect when the same drugs are delivered orally, intramuscularly, subcutaneously or intravenously. As used herein, the term "local" encompasses application of a drug in and around a wound or other operative site, and excludes oral, subcutaneous, intravenous and intramuscular administration. The term "continuous" as used herein encompasses uninterrupted application, repeated application at frequent intervals, and applications which are uninterrupted except for brief cessations such as to permit the introduction of other drugs or agents or procedural equipment, such that a substantially constant predetermined concentration is maintained locally at the wound or operative site.

The advantages of low dose applications of agents in accordance with this aspect of the invention are three-fold. The most important is the absence of systemic side effects that often limit the usefulness of these agents. Additionally, the agents selected for particular applications in the solutions of the present invention are highly specific with regard to the mediators and mediation targets on which they work. This specificity is maintained by the low dosages utilized. Finally, the cost of these active agents per procedure is low.

The advantages of local administration of the agents via irrigation or other fluid application in accordance with this aspect of the invention are the following: (1) local administration guarantees a known concentration at the target site, regardless of interpatient variability in metabolism, blood flow, etc.; (2) because of the direct mode of delivery, a therapeutic concentration is obtained instantaneously and, thus, improved dosage control is provided; and (3) local administration of the active agents directly to a wound or operative site also substantially reduces degradation of the agents through systemic processes (e.g., first- and second-pass metabolism) that would otherwise occur if the agents were given orally, intravenously, subcutaneously or intramuscularly. This is particularly true for those active agents that are proteins and peptides, which are metabolized rapidly. Thus, local administration permits the use of compounds or agents which otherwise could not be employed therapeutically. For example, some agents in the following classes are peptidic: bradykinin receptor antagonists; tachykinin receptor antagonists; opioid receptor agonists; CGRP receptor antagonists; and interleukin receptor antagonists, TNF-receptor antagonists; TGF-β receptor agonists; BMP-2 and BMP-7 receptor agonists; IL4, IL10 and IL-13 receptor agonists; and integrin receptor agonists and antagonists. Local, continuous delivery to the wound or operative site minimizes drug degradation or metabolism while also providing for the continuous replacement of that portion of the agent that may be degraded, to ensure that a local therapeutic concentration, sufficient to maintain receptor occupancy or enzymatic saturation, is maintained throughout the duration of the operative procedure.

Local administration of the solution perioperatively throughout a surgical procedure in accordance with this aspect of the present invention produces a preemptive analgesic, anti-inflammatory and cartilage protective effect. As used herein, the term "perioperative" encompasses application intraprocedurally, pre- and intraprocedurally, intra- and postprocedurally, and pre-, intra- and postprocedurally. To maximize the preemptive anti-inflammatory, analgesic (for certain applications) and cartilage protective (for certain applications) effects, the solutions of the present invention are most preferably applied pre-, intra- and postoperatively. By occupying the target receptors or inactivating or activating targeted enzymes prior to the initiation of significant operative trauma locally, the agents of the present solution modulate specific pathways to preemptively inhibit the targeted pathologic process. If inflammatory mediators and processes are preemptively inhibited in accordance with the present invention before they can exert tissue damage, the benefit is more substantial than if given after the damage has been initiated.

Inhibiting more than one pain, inflammatory or cartilage degradation mediator by application of the multiple agent solutions of the present invention has been shown to dramatically reduce the degree of inflammation and pain, and theoretically should provide a cartilage protective effect. The irrigation solutions of the present invention include combinations of drugs, each solution acting on multiple receptors or enzymes. The drug agents are thus simultaneously effective against a combination of pathologic processes, including pain and inflammation, and loss of cartilage homeostasis. The action of these agents is considered to be synergistic, in that the multiple receptor antagonists and inhibitory agonists of the present invention provide a disproportionately increased efficacy in combination relative to the efficacy of the individual agents. The synergistic action of several of the agents of the present invention are discussed below, by way of example.

Used perioperatively, the solution should result in a clinically significant decrease in operative site pain and inflammation, and of cartilage degradation, relative to currently-used irrigation fluids, thereby decreasing the patient's postoperative analgesic (i.e., opiate) requirement and, where appropriate, allowing earlier patient mobilization of the operative site. No extra effort on the part of the surgeon and operating room personnel is required to use the present solution relative to conventional irrigation fluids. For optimum chondroprotection in accordance with this aspect of the invention, the solutions of the invention are administered directly to a joint prior to, during and/or after a surgical procedure.

In a further aspect of the invention, compositions for the protection of cartilage including anabolic-promoting agents and catabolic inhibitory agents are provided. Such combinations such result in a state that is characterized by: cartilage anabolic activity equaling or exceeding cartilage catabolic activity; the maintenance of cartilage tissue so as to either maintain existing, or to increase, cartilage volume; or an increase in the synthesis of cartilage matrix by articular chondrocytes and in the concomitant reduction in degradation of the cartilage matrix.

BRIEF DESCRIPTION OF THE DRAWINGS

The present invention will now be described in greater detail, by way of example, with reference to the accompanying drawings in which.

DETAILED DESCRIPTION OF THE PREFERRED EMBODIMENT

Figure 1:
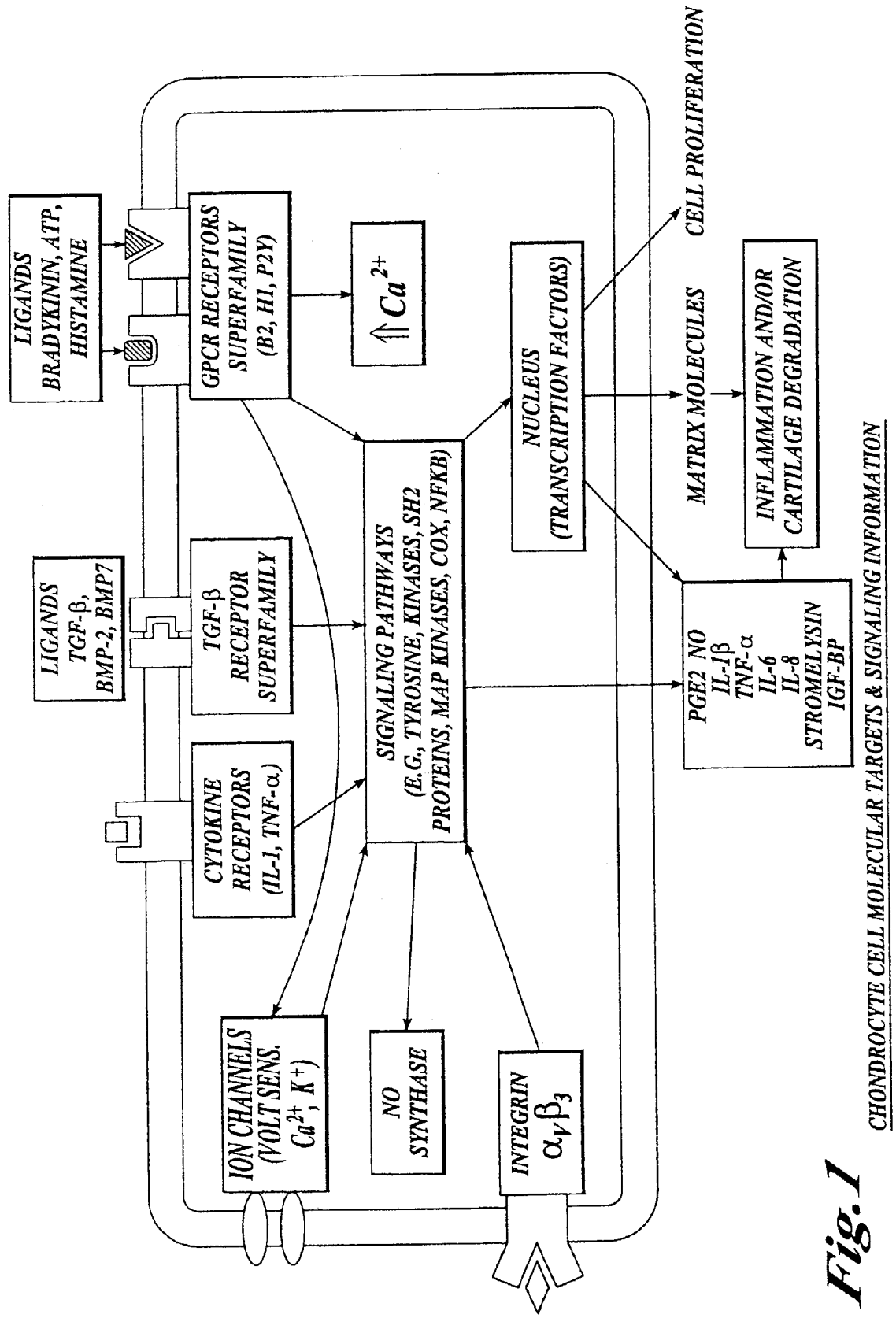
FIG. 1 is a schematic overview of a chondrocyte cell showing molecular targets and flow of signaling information leading to the production of mediators of inflammation and shifts in cartilage metabolism. The integration of extrinsic signals through several families of cell surface receptors, including cytokine receptor such as the interleukin-1 (IL-1) receptor family and the tumor necrosis factor (TNF) receptor family, the TGF-β receptor superfamily and integrins is shown to converge on common intracellular signaling pathways that include major groups of protein molecules that are therapeutic targets of drugs included in the solutions of the present invention (MAP kinases, PKC, tyrosine kinases, SH2 proteins, COX, PLA2 and NF-6B. Activation of these signaling pathways controls chondrocyte expression of a number of inducible gene products, including IL-1, TNF-α, IL-6, IL-8 and Stromelysin (MMP-3), and other mediators (nitric oxide (NO) and PGE2) which may lead to inflammation and/or cartilage degradation, or synthesis of matrix molecules and chondrocyte proliferation.

The present invention provides methods and compositions for the protection of cartilage. In a first embodiment, a method is provided for locally administering to a joint a composition including at least a first agent that acts to promote cartilage anabolic activity and at least a second agent that acts to inhibit cartilage catabolism. In a first aspect of this embodiment of the invention, such compositions are locally delivered by injection of the composition, which may include a sustained release delivery vehicle, into a joint. In a second aspect of this embodiment of the invention, the composition includes a liquid irrigation carrier and is locally and perioperatively delivered to the joint during an operative or interventional procedure.

In a second embodiment of the invention, a method is provided for systemically administering to a patient a composition including at least a first agent that acts to promote cartilage anabolic activity and at least a second agent that acts to inhibit cartilage catabolism.

In a third embodiment of the invention, a method is provided for systemically administering to a patient a composition including at least a first agent that acts to promote cartilage anabolic activity and/or at least a second agent that acts to inhibit cartilage catabolism, in which at least one of the agents is targeted to the joint. Before each of these embodiments is described in greater detail, and without wishing to be limited by theory, a rationale for chondroprotection in accordance with the present invention is set forth.

I. Chondroprotection Rationale

Recent advances in the understanding of the biochemistry and molecular biology of inflammation and cartilage destruction have implicated a role for numerous endogenous cytokines. Multiple pro-inflammatory mediators that have been implicated in producing loss of cartilage in the inflamed joint are the cytokines, TNF-α, IL-1, IL-6 and IL-8. Elevated levels of a number of these pro-inflammatory cytokines appear rapidly in the synovial fluid of acutely injured knee joints and remain elevated in patients for at least 4 weeks (Cameron, M. L. et al., "Synovial fluid cytokine concentrations as possible prognostic indicators in the ACL-deficient knee," *Knee Surg. Sports Traumatol. Arthroscopy* 2:38–44 (1994)). These cytokines are produced locally in the joint from several activated cell types, including synovial fibroblasts, synovial macrophages, and chondrocytes. The locally produced cytokines mediate pathophysiological events in acute and chronic inflammatory conditions and are important autocrine and paracrine mediators of cartilage catabolism. The actions of these cytokines are characterized by their ability to cause multiple effects on distinct cellular targets and by their ability to interact in either a positive or negative synergistic manner with other cytokines. IL-1 and TNF-α are particularly important because they also initiate chondrodestructive effects by disrupting the balance between the normal turnover and destruction of cartilage matrix components by modulating the activity of endogenous proteins (e.g., matrix metalloproteinases (MMPs)) and tissue inhibitor of metalloproteinase (TIMP). Cytokine control of cartilage homeostasis represents a highly regulated balance between active mediators acting on chondrocytes, which determines whether matrix degradation or repair occurs.

Injury to the joint frequently produces an inflammatory response within the joint space that involves the synovial tissue and may lead to degradation of articular cartilage. Dramatic shifts in synovial and cartilage metabolism of the human knee have been described following joint injury and arthroscopic surgery (Cameron, M. L. et al., supra (1994) Cameron, M. L. et al., "The natural history of the anterior cruciate ligament-deficient knee: Changes in synovial fluid cytokine and keratan sulfate concentrations," *Am. J. Sports Med.* 25:751–754 (1997)). Specific pro-inflammatory cytokine levels increase dramatically (up to 2–4 orders of magnitude) in knee joint synovial fluids during the acute inflammatory phase seen after anterior cruciate ligament (ACL) rupture. Significant changes also occur in concentrations of cartilage matrix molecules due to overproduction of matrix metalloproteinases (MMPs), such as collagenase and stromelysin-1, which are elevated in the synovial fluid of patients after acute trauma (Lohmander, L. S. et al., "Temporal patterns of stromelysin-1 tissue inhibitor, and proteoglycan fragments in human knee joint fluid after injury to the cruciate ligament or meniscus," *J. Orthopaedic Res.* 12:21–28 (1994)). Temporally, the changes in cytokines and cartilage matrix markers (e.g., proteoglycans) in synovial fluid, which are correlated with cartilage degeneration, are maximal in the acute injury period but persist for extended periods (3 months to one year), declining slowly and remaining greater than pre-injury baseline levels.

Trauma due to arthroscopic surgery itself causes significant post-surgical inflammation that reflects additional inflammatory activation of cells in the joint, including upregulation of cyclooxygenase-2 and other pro-inflammatory cytokines. A significant proportion (60–90%) of patients with rupture of the ACL show radiographic changes of the knee indicative of osteoarthritis (OA) 10–15 years after injury (Cameron, M. L. et al., supra (1994)). Thus, the combined effects of initial joint injury and surgical trauma may induce a sustained inflammatory state and associated changes in cartilage matrix metabolism which appear to be causative factors resulting in the subsequent development of degenerative changes in articular cartilage and early development of osteoarthritis. The magnitude of this health problem is substantial since the total estimated number of arthroscopic procedures performed in the United States alone in 1996 was 1.8 million with an estimated growth rate of approximately 10% per annum. Thus, it is desirable to provide a pharmaceutical method to prevent degradation of articular cartilage within the joint.

While post-surgical pain and inflammation are recognized as significant clinical problems, current pharmacological treatment regimens for arthroscopic surgery are only directed at acute postoperative analgesia. Existing surgical treatment modalities do not address the chronic inflammatory state that is induced postoperatively and the need to inhibit cartilage destruction of the operatively treated joint. There is a clear need, therefore, to develop an effective, integrated drug therapy that will address both the acute and chronic aspects of pain and inflammation, as well as pathological changes in cartilage metabolism in the injured and operatively treated joint.

According to a first embodiment of this aspect of the invention, a method is provided for reducing or preventing destruction of articular cartilage in a joint, by administering directly to the joint of a patient a composition which includes one or preferably multiple metabolically active chondroprotective agents together with one or more agents for the inhibition of pain and/or inflammation, as previously described, or preferably a combination of two or more metabolically active chondroprotective agents, at least one of which promotes cartilage anabolic processes and at least one of which is an inhibitor of cartilage catabolic processes, in a pharmaceutically effective carrier for intra-articular delivery. Metabolically active agents include, but are not limited to, all compounds that act directly or indirectly to modulate or alter the biological, biochemical or biophysical state of a cell, including agents that alter the electrical potential of the plasma membrane, the ligand binding or enzymatic activity of cellular receptors, intracellular or extracellularly located enzymes, protein-protein interactions, RNA-proteins interactions, or DNA-protein interactions. For example, such agents may include receptor agonists that initiate signal transduction cascades, antagonists of receptors that inhibit signaling pathways, activators and inhibitors of intracellular or extracellular enzymes and agents that modulate the binding of transcription factors to DNA.

Suitable chondroprotective agents include, for example, (1) antagonists of receptors for the interleukin-1 family of proteins, including, for example, IL-1β, IL-17 and IL-18; (2) antagonists of the tumor necrosis factor (TNF) receptor family, including, for example, TNF-R1; (3) agonists for interleukin 4, 10 and 13 receptors; (4) agonists for the TGF-β receptor superfamily, including, for example, BMP-2, BMP-4 and BMP-7; (5) inhibitors of COX-2; (6) inhibitors of the MAP kinase family, including, for example, p38 MAP kinase; (7) inhibitors of the matrix metalloproteinases (MMP) family of proteins, including, for example, MMP-3 and MMP-9; (8) inhibitors of the NF-κB family of proteins, including, for example, the p50/p65 dimer complex with IκB; (9) inhibitors of the nitric oxide synthase (NOS) family, including, for example, iNOS; (10) agonists and antagonists of integrin receptors, including, for example, agonists of $\alpha_v\beta_3$ integrin; (11) inhibitors of the protein kinase C (PKC) family; (12) inhibitors of the protein tyrosine kinase family, including, for example, the src subfamily; (13) modulators of protein tyrosine phosphatases; and (14) inhibitors of protein src homology 2 (SH2) domains. Other suitable chondroprotective agents for use in the invention include other growth factors, such as by way of example insulin-like growth factors (e.g., IGF-1) and fibroblast growth factors (e.g., bFGF).

A first embodiment of the present invention provides a pharmacological method of treating the injured or operatively treated joint using a combination of cartilage protective agents delivered locally to achieve maximal therapeutic benefit. A second embodiment of the present invention provides a pharmacological method of providing therapeutic treatment by systemically administering a combination of cartilage protective agents. The use of a combination of chondroprotective agents overcomes the limitations of existing therapeutic approaches that rely upon on the use of a single agent to block a multifactorial cartilage destructive process in which a shift between synthesis and degradation, in favor of catabolic processes has occurred. This aspect of the invention uniquely utilizes the approach of combining of agents that act simultaneously on distinct molecular targets to promote cartilage anabolism and inhibit unregulated or excess cartilage catabolic processes to achieve maximum inhibition of inflammatory processes and maintain cartilage homeostasis, thereby achieving a chondroprotective effect within the joint. Inhibition of a single molecular target or biochemical mechanism known to induce cartilage destruction (catabolism), such as inhibiting interleukin-1(IL-1) binding to the IL-1 receptor, will likely not be optimal, since, for example, the actions of TNF-α mediated through its unique receptor shares many overlapping pro-inflammatory and cartilage catabolic functions with IL-1 and is also recognized as a major mediator of cartilage destruction in the joint. Similarly, utilizing pharmaceutical agents that only enhance cartilage anabolic processes in the absence of inhibiting catabolic processes will not optimally counteract catabolic factors present within the injured joint.

Specifically, one aspect of the present invention provides pharmaceutical compositions of metabolically active chondroprotective agents that are based upon a combination of at least two agents that act simultaneously on distinct molecular targets. In a representative embodiment, at least one agent is a cytokine or growth factor receptor agonist which directly provides anti-inflammatory activity and/or promotes cartilage anabolic processes and at least a second agent is a receptor antagonist or enzyme inhibitor that acts to inhibit pro-inflammatory and/or cartilage catabolic processes. A representative drug combination includes at least one agent drawn from a class of anti-inflammatory/anabolic cytokines that act functionally to suppress the role of pro-inflammatory cytokines in the joint, promote cartilage matrix synthesis and inhibit matrix degradation. These receptor agonists include, but are not limited to, specific anti-inflammatory and anabolic cytokines, such as the interleukin (IL) agonists (e.g., IL-4, IL-10 and IL-13) and specific members of the transforming growth factor-β superfamily (e.g., TGFβ and BMP-7), insulin-like growth factors (e.g., IGF-1) and fibroblast growth factors (e.g., bFGF). At least a second agent is drawn from a class of receptor antagonists or enzyme inhibitors that acts to inhibit and reduce the activity or the expression of a pro-inflammatory molecular target (e.g., the IL-1 receptor antagonists, TNF-α receptor antagonists, cyclooxygenase-2 inhibitors, MAP kinase inhibitors, nitric oxide synthase (NOS) inhibitors, and nuclear factor kappaB (NFκB) inhibitors). The metabolically active agents include both functional agonists and antagonists of receptors located on the surfaces of cells, as well as inhibitors of membrane bound or extracellularly secreted enzymes (e.g., stromelysin and collagenase). In addition, many of the agents are directed at novel targets that are the intracellularly localized enzymes and transcription factors that transduce and integrate the signals of the surface receptors, including inhibitors of the enzymes NOS, COX-2, and mitogen-activated protein kinases (MAPK) and inhibitors of protein-DNA interactions such as the transcription factor NFκB. This method allows the integrity of cartilage to be maintained by simultaneously promoting cytokine-driven anabolic processes and inhibiting catabolic processes.

The compositions of preferred embodiments of the present invention constitute a novel therapeutic approach by combining multiple pharmacologic agents acting at distinct receptor and/or enzyme molecular targets. To date, pharmacologic strategies have focused on the development of highly specific drugs that are selective for individual receptor subtypes and enzyme isoforms that mediate responses to individual signaling neurotransmitters and hormones. Furthermore, despite inactivation of a single receptor subtype or enzyme, activation of other receptor subtypes or enzymes and the resultant signal transduction often can trigger a cascade effect. This explains the significant difficulty in employing a single receptor-specific drug to block a pathophysiologic process in which multiple signaling mediators (e.g., cytokines, growth factors or eicosonoids) play a role. Therefore, targeting only a specific individual receptor subtype or isotype is likely to be ineffective.

In contrast to the standard approach to pharmacologic therapy, the therapeutic approach of the present compositions is based on the rationale that a combination of drugs acting simultaneously on distinct molecular targets is highly effective in the inhibition of the full spectrum of events that underlie the development of a pathophysiologic state. Furthermore, instead of targeting a specific receptor subtype alone, the compositions include drugs that target common molecular mechanisms operating in different cellular physiologic processes involved in the development of pain, inflammation, and cartilage degradation (see FIG. 1). In this way, the cascading of additional receptors and enzymes in the nociceptive, inflammatory, and cartilage degradation pathways is minimized. In these pathophysiologic pathways, the compositions inhibit the cascade effect both "upstream" and "downstream".

An example of "upstream" inhibition is the cyclooxygenase antagonists in the setting of pain and inflammation. The cyclooxygenase enzymes ($COX_1$ and $COX_2$) catalyze the conversion of arachidonic acid to prostaglandin H that is an intermediate in the biosynthesis of inflammatory and nociceptive mediators including prostaglandins, leukotrienes, and thromboxanes. The cyclooxygenase inhibitors block "upstream" the formation of these inflammatory and nociceptive mediators. This strategy precludes the need to block the interactions of the seven described subtypes of prostanoid receptors with prostanoid products of the COX biochemical pathway. A similar "upstream" inhibitor is aprotinin, a kallikrein inhibitor. The enzyme kallikrein, a serine protease, cleaves the high molecular weight kininogens in plasma to produce bradykinins, important mediators of pain and inflammation. By inhibition of kallikrein, aprotinin effectively inhibits the synthesis of bradykinins, thereby providing an effective "upstream" inhibition of these inflammatory mediators.

The compositions of the invention may also make use of "downstream" inhibitors to control the pathophysiologic pathways. In synoviocyte and chondrocyte preparations that have been treated with a variety of inflammatory cytokines (e.g., IL-1β and TNFα) implicated in progressive articular cartilage degeneration, MAP kinase inhibitors produce a cartilage protective effect. The p38 MAP kinase is a point of conveyance in signaling pathways for multiple catabolic cytokines, and its inhibition prevents upregulation of multiple cellular products mediating cartilage degradation. The MAP kinase inhibitors, therefore, provide a significant advantage in the setting of joint inflammation by providing "downstream" cartilage protective effects that are independent of the physiologic combination of cytokine receptor agonists initiating the shift cartilage homeostasis.

II. Local Delivery of Chondroprotective Compositions

Specific preferred embodiments of the solution of the present invention for use in chondroprotection and surgical procedures preferably include a combination of agents that act simultaneously on distinct molecular targets to promote cartilage anabolism and inhibit unregulated or excess cartilage catabolic processes to achieve maximum inhibition of inflammatory processes and maintain cartilage homeostasis, thereby achieving a chondroprotective effect within the joint.

The irrigation and injectable solutions of one embodiment of the present invention are dilute solutions of one or preferably more chondroprotective agents and, optionally, one or more pain and/or inflammation inhibitory agents in a physiologic carrier. The carrier is a liquid solution, which as used herein is intended to encompass biocompatible solvents, suspensions, polymerizable and non-polymerizable gels, pastes and salves, as well as sustained release delivery vehicles, such as microparticles, microspheres or nanoparticles composed of proteins, liposomes, carbohydrates, synthetic organic compounds, or inorganic compounds. Preferably the carrier is an aqueous solution that may include physiologic electrolytes, such as normal saline or lactated Ringer's solution.

In each of the surgical solutions of a locally delivered embodiment of the present invention, the agents are included in low concentrations in a liquid or fluid solution and are delivered locally in low doses relative to concentrations and doses required with systemic methods of drug administration to achieve the desired therapeutic effect. As used herein, "liquid" or "fluid" is intended to encompass pharmaceutically acceptable, biocompatible solvents, suspensions, polymerizable and non-polymerizable gels, pastes and salves. Preferably the carrier is an aqueous solution that may include physiologic electrolytes, such as normal saline or lactated Ringer's solution. It is impossible or not practical to obtain an equivalent therapeutic effect by delivering similarly dosed agents via other (i.e., intravenous, subcutaneous, intramuscular or oral) routes of drug administration since drugs given systemically are subject to first- and second-pass metabolism. The concentration of each agent is determined in part based on its receptor dissociation constant, $K_d$ or enzyme inhibition constant, $K_i$. As used herein, the term dissociation constant is intended to encompass both the equilibrium dissociation constant for its respective agonist-receptor or antagonist-receptor interaction and the equilibrium inhibitory constant for its respective activator-enzyme or inhibitor-enzyme interaction. Each agent is preferably included at a low concentration of 0.1 to 10,000 times $K_d$ or $K_i$. Preferably, each agent is included at a concentration of 1.0 to 1,000 times $K_d$ or $K_i$ and most preferably at approximately 100 times $K_d$ or $K_i$. These concentrations are adjusted as needed to account for dilution in the absence of metabolic transformation at the local delivery site. The exact agents selected for use in the solution, and the concentration of the agents, varies in accordance with the particular application, as described below.

A solution in accordance with an aspect of the present invention can include just a single or multiple chondroprotective agent(s), preferably multiple chondroprotective agents at least one of which is an anabolic chondroprotective agent and at least one of which is an inhibitor of cartilage catabolism, or a combination of both chondroprotective agent(s) and pain and/or inflammation inhibitory agents, at low concentration. However, due to the aforementioned synergistic effect of multiple agents, and the desire to broadly inhibit cartilage destruction, and optionally to block pain and inflammation, and it is preferred that multiple agents be utilized.

The multiple drug combination can be delivered locally by intra-articular injection or via infusion, including administration periprocedurally (i.e., preoperatively and/or intraoperatively and/or postoperatively) during surgical arthroscopic procedures, alone or coupled with postoperative sustained delivery, such as by a regulated pump or use of a sustained release delivery vehicle. Sustained release delivery vehicles may include, but are not limited to, microparticles, microspheres or nanoparticles composed of proteins, liposomes, carbohydrates, synthetic organic compounds, or inorganic compounds. Thus, in some embodiments, the invention provides for a combination of agents to be delivered via injection or infusion, alone or together with analgesic and/or anti-inflammatory agents. The rapid onset of action achieved by direct, local delivery of the chondroprotective agents at or closely following the time of injury (e.g., perioperatively) has the potential to inhibit initial processes before they can trigger subsequent responses and thereby preemptively limit local tissue damage and the subsequent loss of cartilage.

Advantages of the present invention include: 1) a combination drug therapy directed to the multifactorial causes of cartilage destruction during acute and/or chronic conditions; 2) the combination of chondroprotective agents may be combined with anti-inflammatory and analgesic agents; 3) local delivery of the drug combination (where applicable) achieves an instantaneous therapeutic concentration of chondroprotective agents within the joint; 4) using an irrigation solution periprocedurally (where applicable) provides continuous maintenance of drug levels within the joint in a therapeutically desirable range during an arthroscopic surgical procedure; 5) local delivery (for this embodiment of the invention) permits a reduction in total drug dose and dosing frequency compared to systemic delivery; 6) local site-directed delivery to the joint (for this embodiment of the invention) avoids systemic toxicity and reduces adverse effects; and 7) direct, local delivery to the joint (for this embodiment of the invention) enables use of novel, pharmaceutically active peptides and proteins, including cytokines and growth factors, which may not be therapeutically useful if limited to systemic routes of administration.

From the molecular and cellular mechanisms of action defined for these chondroprotective agents, these compounds are expected to exhibit chondroprotective action when applied perioperatively in an irrigation solution (in combination with other chondroprotective agents or in combination with other anti-pain and anti-inflammation agents described herein) or otherwise administered directly to the joint via infusion or injection. In particular, these agents are expected to be effective drugs when delivered by an irrigation solution during an arthroscopic surgical procedure. Each metabolically active chondroprotective agent may preferably be delivered in combination with one or more other chondroprotective agents, including small molecule drugs, peptides, proteins, recombinant chimeric proteins, antibodies, oligonucleotides or gene therapy vectors (viral and nonviral), to the spaces of the joint. For example, a drug such as a MAPK inhibitor can exert its actions on any cells associated with the fluid spaces of the joint and structures comprising the joint that are involved in the normal function of the joint or are present due to a pathological condition. These cells and structures include, but are not limited to: synovial cells, including both Type A fibroblast and Type B macrophage cells; the cartilaginous components of the joint such as chondroblasts and chondrocytes; cells associated with bone, including periosteal cells, osteocytes, osteoblasts, osteoclasts; inflammatory cells including lymphocytes, macrophages, mast cells, monocytes, eosinophils; and other cells including endothelial cells, smooth muscle cells, fibroblasts and neural cells; and combinations of the above.

This aspect of the present invention also provides for formulations of the active therapeutic agent(s) that may be delivered in a formulation useful for introduction and administration of the drug into the joint that would enhance the delivery, uptake, stability or pharmacokinetics of the chondroprotective agent(s). Such a formulation may include, but is not limited to, microparticles, microspheres, nanospheres or nanoparticles composed of proteins, liposomes, carbohydrates, synthetic organic compounds, or inorganic compounds. The present invention provides for the delivery of a combination of chondroprotective agents, or one or preferably multiple chondroprotective agents with one or more anti-pain and/or anti-inflammation agents present either as multiple pharmaceutically active substances within a homogeneous vehicle (e.g., a single encapsulated microsphere) or as a discrete mixture of individual delivery vehicles (e.g., a group of microspheres encapsulating one or more agents). Examples of formulation molecules include, but are not limited to, hydrophilic polymers, polycations (e.g. protamine, spermidine, polylysine), peptide or synthetic ligands and antibodies capable of targeting materials to specific cell types, gels, slow release matrices (i.e., sustained delivery vehicles, soluble and insoluble particles) as well as formulation elements not listed.

In one aspect, the present invention provides for the local delivery of a combination of two or more chondroprotective agents, or one or preferably multiple chondroprotective agents in combination with one or more anti-pain and/or anti-inflammation agents, alone or in combination with one or more anti-pain and/or anti-inflammatory agents, via an irrigation solution, an infusion containing the drugs which are present at therapeutically effective low concentrations and which enables the drugs to be delivered directly to the affected tissue or joint. The drug-containing infusion or irrigation solution may be employed preoperatively and/or intraoperatively and/or postoperatively in connection with a surgical procedure or may be administered at other times not related to surgical procedures. Systemic methods of drug delivery (e.g., intramuscular, intravenous, subcutaneous) have required higher concentrations of drugs (and higher total dose) to be administered to the patient in order to achieve significant therapeutic concentrations in the targeted joint. Systemic administration may also result in high concentrations in tissues other than the targeted joint, which is undesirable and, depending on the dose, may result in adverse side effects. These systemic methods subject the drug to second-pass metabolism and rapid degradation, thereby limiting the duration of the effective therapeutic concentration. Because the combination of chondroprotective agents (with or without one or more anti-pain and/or anti-inflammatory agents) are administered directly to the joint by infusion or by irrigation, vascular perfusion is not required to carry the drug to the targeted tissue. This significant advantage allows for the local delivery of a lower therapeutically effective total dose for a variety of chondroprotective drugs.

A. Local Delivery Methods

The solutions of the present invention have application for a variety of operative/interventional procedures, including surgical, diagnostic and therapeutic techniques. The combination of chondroprotective agents of the invention may be administered by injection or by irrigation. For solutions for injection, the amount of active ingredient that may be combined with the carrier materials to produce a single dosage form will vary depending upon the patient to be treated, the nature of the active agents in the solution and the particular mode of administration. It will be understood, however, that the specific dose level for any particular patient will depend upon a variety of factors including the activity of the specific compound employed, the age, body weight, general health, sex and diet of the patient, time of administration, route of administration, rate of excretion of the drug combination, and the severity of the particular disease undergoing therapy.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in propanediol. Among the acceptable vehicles and solvents that may be employed are water, Ringer's solution, and isotonic sodium chloride solution. In addition, sterile, fixed oils are conventionally employed as a solvent or suspending medium. For this purpose any biocompatible oil may be employed including synthetic mono- or diglycerides. In addition, fatty acids such as oleic acid find use in the preparation of injectables.

The solutions for injection of the invention may be administered in connection with an arthroscopic surgical procedure or at any time determined to be desirable by a physician directing patient care.

The irrigation solutions of the invention may be perioperatively applied during arthroscopic surgery of anatomic joints. As used herein, the term "perioperative" encompasses application intraprocedurally, pre- and intraprocedurally, intra- and postprocedurally, and pre-, intra- and postprocedurally. Preferably the solution is applied preprocedurally and/or postprocedurally as well as intraprocedurally. Such procedures conventionally utilize physiologic irrigation fluids, such as normal saline or lactated Ringer's, applied to the surgical site by techniques well known to those of ordinary skill in the art. The method of the present invention involves substituting the anti-pain/anti-inflammatory/chondroprotective irrigation solutions of the present invention for conventionally applied irrigation fluids. The irrigation solution is applied to the wound or surgical site prior to the initiation of the procedure, preferably before tissue trauma, and continuously throughout the duration of the procedure, to preemptively block pain and inflammation, and cartilage degradation. As used herein throughout, the term "irrigation" is intended to mean the flushing of a wound or anatomic structure with a stream of liquid. The term "application" is intended to encompass irrigation and other methods of locally introducing the solution of the present invention, such as introducing a gellable version of the solution to the operative site, with the gelled solution then remaining at the site throughout the procedure. As used herein throughout, the term "continuously" is intended to also include situations in which there is repeated and frequent irrigation of wounds at a frequency sufficient to maintain a predetermined therapeutic local concentration of the applied agents, and applications in which there may be intermittent cessation of irrigation fluid flow necessitated by operating technique.

The concentrations listed above for each of the agents within the solutions of the present invention are the concentrations of the agents delivered locally, in the absence of metabolic transformation, to the operative site in order to achieve a predetermined level of effect at the operative site. It is understood that the drug concentrations in a given solution may need to be adjusted to account for local dilution upon delivery. Solution concentrations in the above embodiments are not adjusted to account for metabolic transformations or dilution by total body distribution because these circumstances are avoided by local delivery, as opposed to oral, intravenous, subcutaneous or intramuscular application.

Arthroscopic techniques for which the present solution may be employed include, by way of non-limiting example, partial meniscectomies and ligament reconstructions in the knee, shoulder acromioplasties, rotator cuff debridements, elbow synovectomies, and wrist and ankle arthroscopies. The irrigation solution is continuously supplied intraoperatively to the joint at a flow rate sufficient to distend the joint capsule, to remove operative debris, and to enable unobstructed intra-articular visualization.

Suitable arthroscopic irrigation solutions for inhibition of cartilage degradation and control of pain and inflammation during such arthroscopic techniques are provided in Examples 1–3 herein below.

In each of the solutions of the present invention intended for local delivery, the agents are included in low concentrations and are delivered locally in low doses relative to concentrations and doses required with systemic methods of drug administration to achieve the desired therapeutic effect. It is impossible to obtain an equivalent therapeutic effect by delivering similarly dosed agents via other (i.e., intravenous, subcutaneous, intramuscular or oral) routes of drug administration since drugs given systemically are subject to first- and second-pass metabolism and are often rapidly cleared from the system circulation.

Practice of the present invention should be distinguished from conventional intra-articular injections of opiates and/or local anesthetics at the completion of arthroscopic or "open" joint (e.g., knee, shoulder, etc.) procedures. The solutions of this aspect of the present invention are used for continuous infusion throughout the surgical procedure to provide preemptive inhibition of pain and inflammation. In contrast, the high concentrations necessary to achieve therapeutic efficacy with a constant infusion of currently used local anesthetics can result in profound systemic toxicity.

Upon completion of the procedure of the present invention, it may be desirable to inject or otherwise apply a higher concentration of the same chondroprotective agent(s) and/or pain and/or inflammation inhibitors as used in the irrigation solution at the operative site, as an alternative or supplement to opiates. It may also be desirable to deliver a sufficient amount of the solution to the joint after the surgical procedure so that a bolus of the solution remains in the synovial capsule of the patient following the surgical procedure.

As noted previously, the compositions of the present invention including multiple chondroprotective agents, including preferably at least one catabolic inhibitory agent and at least one anabolic-promoting agent, may also be adapted for direct injection into an atomic joint. Preferably the agents are selected and each agent is included in a sufficient amount to provide a combination that is therapeutically effective when the solution is delivered locally to the joint of a patient to both inhibit cartilage catabolic processes and to promote cartilage anabolic processes. Such compositions may be locally injected to provide a chondroprotective effect to a patient suffering from a chronic condition, such as osteoarthritis or rheumatoid arthritis, or an acute condition such as trauma from surgery or accidental injury. One suitable composition for local injection is provided in Example 4 below.

III. Systemic Administration of Chondroprotective Compositions

Embodiments of the present invention have thus far been described in terms of local delivery of chondroprotective compositions, such as by intra-articular injection. Local administration has been described as having several advantages over systemic administration, including the avoidance of systemic side effects. While local delivery of the compositions of the present invention is preferred in many instances, it may not be practical for some cartilage degenerative conditions. This is particularly the case for patients suffering from chronic cartilage degenerative diseases in which multiple sites simultaneously are at risk of cartilage degradation, such as rheumatoid arthritis, polyarticular osteoarthritis and other polyarthropathies. For such patients, injection of chondroprotective compositions into each or a majority of their diseased sites (e.g., joints) may be painful, impractical, costly or otherwise dissuasive of treatment. The chondroprotective compositions described above for local delivery may, in accordance with another aspect of the present invention, be adapted for administration via systemic routes. Systemic delivery of the compositions of the present invention is suitable for, but not limited to, treatment of patients with multiple sites at risk of cartilage degeneration. In addition to polyarticular osteoarthritis and rheumatoid arthritis, discussed further below, this aspect of the present invention may be useful for treating other noninflammatory and inflammatory arthrititides including, but not limited to, neuropathic arthropathy, acute rheumatic fever, ochronosis, systemic lupus erythematosus, juvenile rheumatic arthritis, psoriatic arthritis, ankylosing spondylitis, and other spondyloarthropathies and crystalline arthropathies.

A. Arthritis Mechanisms

This aspect of the invention may be better appreciated with an understanding of the mechanisms involved in the degradation of articular cartilage in rheumatologic arthropathies (e.g., rheumatoid arthritis (RA) and osteoarthritis (OA)). RA is the most common form of inflammatory arthritis, affecting approximately 3% of women and 1% of men. The majority of patients have multiple, and usually symmetrical, joint involvement, especially the small joints of the hands, the elbows, the wrists and the shoulders. OA is the most common form of joint disease and is second only to cardiovascular disease as a cause of early retirement and disability. OA commonly is polyarticular. The destruction of hyaline articular cartilage is the hallmark of OA and disabling RA.

Although various therapeutic approaches may provide relief of symptoms, no treatment has been proven to retard progression of articular cartilage degradation. In OA, there may be either a suppression of normal chondrocyte functions or the constitutive inability of these cells to match the rate of repair with the increased rate of degradation of the matrix. Various cytokines and inflammatory mediators have been shown to either create an imbalance in the synthetic functions of the chondrocytes or, alternatively, to increase cartilage matrix catabolism by upregulating various matrix-degrading enzymes, including the matrix metalloproteinases (including collagenases).

To optimally treat diseases that involve cartilage degeneration, it is expected that a treatment regimen that stimulates anabolic processes and simultaneously inhibits cartilage catabolism will be required. Thus, the therapeutic approach described previously for the inhibition of cartilage destruction in joint disease, based upon a combination of a cartilage anabolic agent and an inhibitor of cartilage catabolism, is expected to have utility in the treatment of arthritic conditions such as OA and RA. As noted above, practical considerations dictate that such diseases that simultaneously affect multiple sites in the body are best treated by systemic administration of these therapeutic agents.

B. Combinations of Agents

This aspect of the present invention thus provides compositions including combinations of chondroprotective agents, and methods of systemic administration of such compositions. Agents that target differing receptors or molecular targets are utilized for a multifactorial approach, as described previously. Preferably the therapeutic compositions of the present invention include at least one chondroprotective agent that promotes cartilage anabolic activity, and at least one agent that inhibits cartilage catabolism. This combination is expected to optimize conditions for homeostasis, and to be preferable over conventional therapies that address only cartilage breakdown or more recent research to develop drugs that address only cartilage synthesis. Suitable anabolic-promoting agents and catabolic inhibitory agents have been described above for local administration, and are also expected to be useful for the present systemic compositions. Aspects and advantages of the compositions of the present invention described above with respect to local delivery are to be understood to also apply, to the extent applicable, to the systemic embodiments of the invention.

Thus chondroprotective compositions of the present invention may suitably include one or more of the following anabolic-promoting agents, by way of non-limiting example: interleukin (IL) agonists (e.g., IL-4, IL-10, IL-13 agonists), members of the transforming growth factor-β superfamily, including TGF-β agonists (e.g., TGFβ1, TGFβ2, TGFβ3) and bone morphogenetic protein agonists (e.g., BMP-2, BMP-4, BMP-6, BMP-7), insulin-like growth factors (e.g., IGF-1) and fibroblast growth factors (e.g., bFGF), and fragments, deletions, additions, amino acid substitutions, mutations and modifications that retain the biological characteristics of these naturally occurring agents.

Chondroprotective compositions of the present invention may suitably include one or more of the following inhibitors of cartilage catabolism, by way of nonlimiting example: IL-1 receptor antagonists, TNF-α receptor antagonists, cyclooxygenase-2 specific inhibitors, MAP kinase inhibitors, nitric oxide synthase inhibitors, nuclear factor kB inhibitors, inhibitors of matrix metalloproteinases, cell adhesion molecules (including integrin agonists and integrin antagonists) that inhibit cartilage catabolism, intracellular signaling inhibitors (including protein kinase C inhibitors and protein tyrosine kinase inhibitors) that inhibit cartilage catabolism, and inhibitors of SH2 domains that inhibit cartilage catabolism.

As described with respect to previous embodiments, the at least one inhibitor of cartilage catabolism in the systemic anabolic agent/catabolic inhibitory agent combination may be a soluble receptor that inhibits cartilage catabolism, such as a soluble IL-1 receptor or a soluble tumor necrosis factor receptor. Specific examples include recombinant soluble human IL-1 receptors, soluble tumor necrosis factor receptors and chimeric rhTNFR:Fc. Examples of soluble tumor necrosis factors useful for incorporation in the present invention include the functional TNF-α antagonists disclosed in U.S. Pat. No. 5,605,690 issued to Jacobs et al., while examples of soluble human IL-1 receptors useful in the present invention include those disclosed in U.S. Pat. No. 6,159,460 to Thompson et al., the disclosures of which are hereby expressly incorporated by reference. Particularly promising catabolic inhibitors useful for combination with anabolic agents for systemic delivery in accordance with this aspect of the present invention include IL-1ra, TNFR1-IgG1 fusion protein and inhibitors of matrix metalloproteinases.

As further described below, the chondroprotective compositions may also include one or more inhibitors of pain and/or inflammation or other therapeutic agents. Examples of chondroprotective compositions suitable for systemic delivery are provided in Examples 5 through 20 below.

C. Systemic Delivery

The present aspect of the invention entails systemic delivery of chondroprotective agents, and potentially anti-inflammatory and/or analgesic agents or other therapeutic agents, so as to provide therapeutic effect at multiple articular sites. As used herein, the terms "systemic delivery" and "systemic administration" are intended to include but are not limited to oral, intramuscular, subcutaneous, intravenous, inhalational, sublingual, buccal, topical, transdermal, nasal, and other routes of administration that effectively result in dispersement of the delivered agent to a single or multiple sites of intended therapeutic action. Preferred routes of systemic delivery for the present compositions are intravenous, intramuscular, subcutaneous and inhalational. It will be appreciated that the exact systemic administration route for selected agents utilized in particular compositions of the present invention will be determined in part to account for the agent's susceptibility to metabolic transformation pathways associated with a given route of administration. For example, peptidergic agents may be most suitably administered by routes other than oral.

The compositions of the present invention may be systemically administered on a periodic basis at intervals determined to maintain a desired level of therapeutic effect. For example, compositions may be administered, such as by subcutaneous injection, every two to four weeks. The dosage regimen will be determined by the physician considering various factors that may influence the action of the combination of agents. These factors will include the cartilage site intended for treatment, the size of the joint (if appropriate), the amount of cartilage tissue to be treated, the site of cartilage damage, the condition of the damaged cartilage at the time of treatment, the patient's age, sex and weight, and other clinical factors. The dosage for each individual agent will vary as a function of the other anabolic and catabolic inhibitory agents that are included in the composition, as well as the presence and nature of any drug delivery vehicle (e.g., a sustained release delivery vehicle). In addition, the dosage quantity may be adjusted to account for variation in the frequency of administration and the pharmacokinetic behavior of the delivered agent(s). Progress in the treatment of an individual can be monitored through a variety of methods known to those in the art, including clinical assessment, radiographic and magnetic resonance imaging, computed tomography, biochemical markers and arthroscopic evaluation.

D. Delivery Vehicles and Targeting

Methods of compounding compositions for various routes of systemic administration are known and may be adapted for use with the present compositions. The chondroprotective agents and, if included, inflammation and pain inhibitory agents or other therapeutic agents are suitably compounded in a physiologic carrier or delivery vehicle, such as those described previously, as appropriate for a given route of systemic administration. In one aspect of the present invention, systemic delivery of these combinations of agents, or any component or components thereof, may be incorporated in or combined with a drug delivery vehicle such as a sustained release delivery vehicle and/or a depot.

As used herein, the term "delivery vehicle" is intended to include all structures that contain, couple to or carry a therapeutic agent, such as nanospheres and other nanoparticles, microspheres and other microparticles, micelles and liposomes, including such vehicles formed of proteins, lipids, carbohydrates, synthetic organic compounds or inorganic compounds. Preferred delivery vehicles for the targeted systemic compositions of the present invention, decribed further below, are "particles," which is intended to include nanospheres and other nanoparticles, microspheres and other microparticles, micelles, and other delivery vehicles, but excluding liposomes which are less preferred as also described below. The term "delivery system" is intended to refer to a delivery vehicle and one or more contained or coupled therapeutic agents.

The term "sustained release system" is intended to mean a delivery system that provides for extended, enhanced or regulated delivery, duration or availability of any or all of the incorporated agents. Examples of sustained release systems include but are not limited to drug-containing microparticles, microspheres, nanoparticles, proteins, liposomes, carbohydrates, synthetic organic compounds, inorganic compounds and injectable hydrogels such as that disclosed by U.S. patent application Ser. No. 09/861,182 to Jun Li et al., hereby expressly incorporated by reference. Suitable sustained release systems are known for other pharmaceuticals and may be adapted in accordance with the present invention to deliver chondroprotective agents at a relatively consistent therapeutic level, thereby reducing side effects and providing a longer duration of action when compared to a bolus systemic delivery of agents.

The term "depot" as used herein is intended to mean a drug delivery system, delivered at the site of intended action or remote from the site of intended action, which provides a reservoir of therapeutic agents for sustained release.

The individual agents may be compounded in a homogeneous mixture, may be a mixture or administration of separate microparticles, microspheres, etc., or may be concurrently and separately administered.

In order to minimize adverse or unwanted systemic effects, in the one aspect of the invention, a therapeutic strategy is to deliver the combination of agents in a delivery vehicle that is preferentially targeted to a site or sites in the body that contain cartilage, in particular joints. As used herein, a "targeted delivery vehicle" is a delivery vehicle that can be used for the systemic delivery of a drug and that is adapted such that a greater quantity of the drug reaches the joint or desired local site of action than would otherwise reach the joint or desired local site of action using a non-adapted delivery vehicle or in the absence of a delivery vehicle (i.e., the drug is preferentially localized to the joint because the targeted delivery vehicle preferentially associates with molecules, cells or anatomic structures of the joint). Likewise, a "targeted delivery system" is such a targeted delivery vehicle containing one or more therapeutic drugs. A "targeted drug" is intended to refer to a therapeutic agent that is directly linked or coupled to a targeting structure. As used herein, a systemically administered drug that has a "preferential effect" at a joint or desired local site of action exhibits greater pharmacological activity at the joint or desired local site of action than at the majority of other sites in the body.

1. Targeting Rationale

In OA, there may be either a suppression of normal chondrocyte function or the constitutive inability of these cells to match the rate of repair with the increased rate of degradation of the matrix. Various cytokines and inflammatory mediators have been shown to either create an imbalance in the synthetic function of the chondrocytes or, alternatively, to increase cartilage matrix catabolism by upregulating various matrix-degrading enzymes, including the matrix metalloproteinases (including collagenases). Thus, the loss of integrity of the cartilage extracellular matrix (CEM) is the result of a dynamic imbalance between the synthetic activities of the cartilage anabolic processes and catabolic activities that lead to degradation.

Systemic administration of cytokines, growth factors and other bioactive molecules is often associated with serious side effects. For example, pathological effects have been correlated with the administration of systemic TGF-β1 and other factors. In addition, systemic delivery of an unprotected (naked) polypeptide, often preferable for poly-joint arthropathies as previously noted, frequently is limited by problems with stability of protein agents due to rapid degradation and inactivation of the therapeutic protein in the circulation.

The breakdown of articular cartilage in OA and RA is likely to be related to the synthesis and release of catabolic factors in the microenvironment of the joint. Prior studies have demonstrated that pro-inflammatory cytokines (e.g., IL-1) and inducible genes (e.g., NO synthase, COX-2, MMPs) are highly expressed in synovial membranes from patients with inflammatory arthritides. Similarly, these mediators and genes are frequently expressed in OA-affected chondrocytes. In both cases, it is a specialized microenvironment of the joint that defines a pathophysiological milieu that critically affects the state of articular cartilage. For this reason, it is desirable to target therapeutic molecules to preferentially localize and act on their intended targets within the joint space. This aspect of the invention provides a mechanism for targeting a systemically administered anabolic chondroprotective agent and/or a systemically administered catabolic inhibitory chondroprotective agent, and preferably both, to the joint for cartilage protection of the joint.

A preferred route of delivery is thus to target these protein factors to the site of action in the joint. To achieve clinical use, a safe method is needed for the delivery of these agents within the joints of patients in a sustained and localized manner. A biodegradable drug delivery vehicle that both protects and stabilizes systemically administered anabolic factors and/or catabolic inhibiting factors while outside the joint, and that simultaneously provides a unique method to target the drug delivery vehicle to the joint, is also desired.

Cartilage anabolic growth factors are potent mediators that are secreted by the body locally within the joint in minute quantities to elicit local biological responses in articular cartilage. Under normal physiologic conditions, appropriate anabolic growth factors are produced by chondrocytes within cartilage and synoviocytes within other joint structures in sufficient concentrations to serve as the necessary signal to maintain the cartilage in a healthy, stable state by influencing cartilage matrix metabolism.

2. Antibody Targeted Delivery Vehicles

A preferred targeted chondroprotective composition of the present invention includes at least one anabolic-promoting chondroprotective agent and/or at least one catabolic inhibitory chondroprotective agent, and preferably both an anabolic-promoting chondroprotective agent and a catabolic inhibitory chondroprotective agent, contained within a targeted delivery vehicle. The targeted delivery vehicle preferably comprises particles, and most preferably nanoparticles, that encapsulate at least one, and preferably all, of the chondroprotective agents. The particles are targeted to the joint by a targeting antibody or antibody fragment that is coupled to the particle, which antibody or fragment is specific for an antigenic determinant that is localized within the joint (i.e., preferentially expressed within the joint relative to most other locations within the body, preferably highly expressed within the joint, and more preferably that is restricted in expression to the joint). The antibody-targeted particles, also referred to herein as "targeted immunoparticles," and the chondroprotective agent(s) encapsulated therein are systemically administered. A portion of the targeted composition is taken up by the joint. The remainder of the composition is excreted and/or metabolized. Within the joint, the targeting antibodies or fragments bind to the targeted antigen. Over time, the particles degrade within the joint, delivering a therapeutic concentration of the chondroprotective agent(s) locally within the joint in a sustained release manner over a predetermined period of time to act locally on the cells to be modulated (e.g., the primary cells of the joint) including the synoviocytes and the chondrocytes. The therapeutic agents may diffuse or be released into the synovial fluid to subsequently bind to the surfaces of the cells of the joint structures, undergo uptake or entry into cells of the joint structures, or directly act on cytokines and/or proteases that may be present within the synovial fluid.

The targeted compositions of this aspect of the present invention can be targeted to the joints of a patient in accordance with the present invention, without knowledge of the specific molecular pathology that underlies the joint disease. The targeting antibody ensures that the encapsulated agents are preferentially localized within the joint, and more preferably are localized in close proximity to or are bound to a constituent of the articular cartilage.

This aspect of the present invention thus provides a method to treat patients suffering from inflammatory, non-inflammatory or other joint diseases involving onr or multiple joints by administering a pharmaceutical preparation including a targeted drug delivery vehicle, preferably containing both a cartilage anabolic agent and an anti-catabolic agent. Such patients may suffer from OA, RA or other diseases of the joint such as noninflammatory and inflammatory arthrititides including, but not limited to, neuropathic arthropathy, acute rheumatic fever, ochronosis, systemic lupus erythematosus, juvenile rheumatic arthritis, psoriatic arthritis, ankylosing spondylitis, and other spondyloarthropathies and crystalline arthropathies. The targeted treatment methods and compositions of this aspect of the invention are particularly well suited for patients suffering from osteoarthritis. The systemic delivery of the combination of agents in a carrier that is targeted to the joint enables treatment of such conditions while minimizing adverse or unwanted systemic effects.

a. Characteristics and Identification of Targets within the Joint

The present invention provides methods and compositions for targeting drugs to the joint, and specifies preferred targets within the joint including antigenic determinants associated with molecules, cells and tissues of articular cartilage and other joint structures. Examples of such targets are selected from: collagens, including collagen Type II and the minor collagens Type V, VI, IX, X and XI; proteoglycans including large aggregating proteoglycans, aggrecan, decorin, biglycan, fibromodulin and lumican; cartilage oligomeric matrix protein, glycoprotein-39; proteoglycan chondroitin-sulfate and glycosaminoglycans; macrophage synoviocytes and fibroblast synoviocytes; and chondrocytes.

In a preferred embodiment, the targeted immunoparticles react irreversibly, bind in a reversible manner, or associate with specific components of the articular cartilage (also known as hyaline cartilage) within the joint. Other molecular targets within the joint may include components of the articular cartilage extracellular matrix, such as cartilage specific collagens, including collagen Type II, V, VI, IX, X, and XI, aggrecan and other small leucine-rich proteoglycans including decorin, biglycan, fibromodulin and lumican. The proteoglycans are high molecular weight complexes of protein and polysaccharide and are found throughout the structural tissues of vertebrates, such as cartilage, but also are present on cell surfaces. Glycosaminoglycans (GAGs), the polysaccharide units in proteoglycans, are polymers of acidic disaccharides containing derivatives of the amino sugars glucosamine or galactosamine, and are useful targets. Cartilage oligomeric matrix protein (COMP) and glycoprotein-39 (HC-gp39), also termed YKL-40, similarly are useful targets.

Articular cartilage contains several genetically distinct types of collagen that are useful in the present invention as molecular targets to which immunoparticles, including corresponding antibodies, can attach, thus permitting delivery of the encapsulated therapeutic agents to the site of antibody binding. Type II collagen, the primary collagen of articular cartilage, accounts for 90% to 95% of the total collagen content of articular or hyaline cartilage and forms the cross-banded fibrillar structure noted by electron microscopy. Type II collagen is also a unique and specific marker of hyaline cartilage. Hollander, et al., *J. Clin. Invest.* 93:1722 (1994); Freed, L et al., *Exp. Cell Res.* 240:58 (1998). A major extracellular modification of the collagen molecules, which occurs after fibril formation, is the development of covalent interfibrillar cross-links. Antibodies that bind to epitopes specific to Type II collagen have been described. Kafienah, W. et al., *Tissue Engineering* 8:817–826 (2002); Kolettas, E, et al., *Rheumatology* 40:1146–1156 (2001). Type II collagen and its associated epitopes in articular cartilage represent preferred targets for the present invention.

For example, a monoclonal antibody to Type II collagen, isotype $IgG_1$, designated clone 6B3 (Linsenmayer, T. F. et al., *Biochem. Biophys. Res. Commun.* 92(2):440–6 (1980)) recognizes both α1(II) and α3(XI) chains that have identical primary structures. In Western blotting, this mAb reacts with the $TC^A$ fragment of lathyritic Type II collagen after digestion with mammalian collagenase. It also reacts with pepsin-digested Type II collagen. Its epitope is localized in the triple helix of Type II collagen and it shows no cross-reaction with Type I or Type III collagen. Immunoblotting of cyanogen bromide (CNBr) peptides of collagen II shows that this mAb reacts with the CB11 fragment, which is the site of immunogenic epitopes along the intact Type II molecule.

In yet another example, a monoclonal antibody to Type II collagen (isotype $IgG_1$) (Miller, E. J., *Biochemistry* 11:4903–4909 (1972); Glant, T. T., et al., *Histochemistry* 82:149–158 (1985a); *British Journal of Haematology* 90:757–766 (1995)) was developed using human cartilage specific CNBr-cleaved collagen II as the immunogen. This mAb, available commercially through Chemicon International (Temecula, Calif.), reacts with both pepsin-solubilized and CNBr-cleaved human and bovine Type II collagen. No cross-reactivity is observed with collagen Types I, III, V and IX. In a preferred embodiment of the present invention, the antibody to Type II collagen binds to the target epitope with a dissociation constant in the range of 0.1–10 nM.

The quantitatively minor collagens of articular cartilage also contribute to the structure of the matrix and serve as useful targets for the present invention. For example, Type IX collagen, a short nonfibrillar collagen (which contains a glycosaminoglycan chain and is therefore also considered a proteoglycan) binds covalently to Type II collagen fibrils and may help link fibrils together or bind fibrils to other matrix molecules. Type XI collagen, a minor fibrillar collagen, may be involved in controlling the diameter of the Type II fibrils. Other collagens, including Type V and Type VI, may also form part of the matrix. These minor collagens of articular cartilage may also function as targets for antibody-directed immunoparticle binding with appropriate antibodies.

In another embodiment of the invention, distinct types of proteoglycans contained in articular cartilage are useful in the present invention as molecular targets for the binding of immunoparticles, thus permitting delivery of the therapeutic agents to the site of antibody binding. In articular cartilage, proteoglycans constitute the second largest portion of the solid phase, accounting for 5% to 10% of the wet weight. The proteoglycans of the cartilage matrix consist primarily of large aggregating (50% to 85%) and large nonaggregating (10% to 40%) proteoglycans. Distinct small proteoglycans are also present.

The proteoglycans of cartilage that contribute most significantly to the material properties of the tissue are the large, high-molecular weight monomers (molecular weight, $1-4 \times 10^6$). Structurally, the large proteoglycans consist of an extended protein core with several distinct regions: an N-terminal region with two globular domains (G1 and G2), a domain rich in keratan sulfate; a longer domain rich in chondroitin sulfate that may also contain some interspersed keratan sulfate and neutral oligosaccharide chains; and a C-terminal globular domain, G3. Aggregates are formed by many proteoglycan monomers binding to a chain of hyaluronate at the G1 globular domain. Each proteoglycan-hyaluronate bond is stabilized by a separate globular link protein (molecular weight, 41,000 to 48,000). The large size of the chondroitin sulfate-rich region (200–400 nm) and abundance of chains of the chondroitin-sulfate proteoglycan aggregate make this a preferred target for targeted immunoparticles of this aspect of the invention.

An additional target for antibodies or fragments thereof that are coupled to immunoparticles of the present invention is provided by HC gp-39. Within the joint, fragments of HC gp-39 that have appropriate antigenic properties also are sufficient for targeting the drug delivery vehicle.

Immunoparticles may be targeted with antibodies or fragments thereof to react irreversibly, bind in a reversible manner (most commonly), or associate with specific structures of the synovial membrane of the joint. The specialized cells of the joint that are preferred targets include the two principal cell types of the synovium, macrophage synoviocytes (Type A) and fibroblast synoviocytes (Type B).

Additional targets for antibodies or fragments thereof that are coupled to immunoparticles of the present invention are chondrocytes. These cells are known to express a variety of proteins which are present on their surfaces and which can serve as epitopes for cellular targeting.

In another embodiment of the invention, the chondroitin-sulfate proteoglycan associated with articular cartilage represents a preferred target for the targeted drug delivery system. Monoclonal antibodies useful for the present invention that bind to epitopes specific to chondroitin-sulfate proteoglycan have been described. Morgan Jr., A. et al., *Hybridoma* 1:27–36 (1981); Schrappe, M. et al., *Cancer Res.* 52:3838–3844 (1992); Schrappe, M. et al., *Cancer Res.* 51:4986–93 (1991). One such example is a mouse-anti-human chondroitin-sulfate proteoglycan monoclonal antibody, designated clone 9.2.27 ($IgG_{2a}$ isotype). The 9.2.27 antibody recognizes the mature chondroitin sulfate proteoglycan core glycoprotein of 250 kDa as well as precursor polypeptides of 210, 220 and 240 kDa. A mouse anti-human aggregan monoclonal antibody, clone 2A2.1, is also suitable for the present invention and is commercially available from United States Biological (Swampscott, Mass.). This antibody does not react with chondroitin sulfate linkage regions. Transmission electron microscopy indicates that it binds within the N-terminal portion of the chondroitin sulfate-attachment region.

b. Targeting of Neoepitopes Associated with Cartilage Degeneration

Biomolecular constituents of cartilage that may be either absent from normal adult cartilage or present at very low levels, but that are elevated or more highly expressed in certain stages of either RA or OA, also may serve as targets for the targeted drug delivery systems of the present invention. Preferred targets associated with cartilage degenerative conditions are neoepitopes that appear on articular cartilage of patients diagnosed with OA, RA or other degenerative joint diseases, such as neoepitopes of aggrecan or other cartilage proteoglycans, and specifically neoepitopes that are immunolocalized in the superficial layer of articular cartilage of such patients.

In one aspect of the invention, the targeting antibodies or antibody fragments specifically bind to neoepitopes or cleavage sites of Type II collagen or Type II collagen fragments, particularly such neoepitopes or cleavage sites generated by the individual or combined action of matrix metalloproteinase (MMP)-1, 3, 8 or 13, or other members of the MMP protein family, or a member of the A Disintegrin And Metalloproteinase with Thrombospondin motifs' (ADAMTS) protein family. ADAMTS are further described in Patent Applications WO 00/04917, EP 0 823 478 and U.S. Pat. No. 5,811,535 and in Tang, B. et al., *FEBS Lett.* 445 (2–3):223–225 (1999).

Antibodies directed at specific epitopes that are defined by specified regions of the Type II collagen structure are useful for targeting compositions of this invention. These structural regions are, in part, important in cartilage affected by degradation of Type II collagen that occurs in OA and RA. Degradation of Type II collagen results in fragments of the collagen protein that are released from the cartilage matrix and appear in the synovial fluid, move into the circulation, and are eliminated through the urine. To have maximal utility, compositions of the present invention target epitopes that remain physically associated with the cartilage matrix rather than on released fragments.

Each of the collagenases, MMP-1 (EC 3.4.24.7), MMP-8 (EC 3.4.24.34), and MMP-13 (EC 3.4.24.-) has the capacity to cleave triple-helical fibril-forming Type II collagen, giving rise to a large (¾-length) amino-terminal fragment and a smaller (¼-length) carboxy-terminal fragment. Kafienah, W. et al., *Biochem. J.* 331:727–732 (1998). They all initially cleave at a specific Gly-Leu/Ile bond to generate the characteristic ¾ and ¼ fragments. Specific collagenase isotypes have been implicated in the pathologic loss of cartilage. Billinghurst, R. et al., *J. Clin. Invest.* 99:1534–1545 (1997). For example, in an animal model of OA, focal areas of collagenase 1 and collagenase 3 proteins have been localized to the extracellular matrix of OA lesion sites in the knee joint, coincident with ¾–¼ collagen cleavage. Collagenase 3 protein was also abundant throughout the medial tibial cartilage in the diseased joints. Huebner, J. et al., *Arthritis & Rheumatism* 41:877–890 (1998).

Collagenase 1 (MMP-1) has been detected in synovium, synovial fluid, and cartilage samples from humans with RA and with OA. Collagenase 3 (MMP-13) cleaves collagen Type II at a rate that is 5–10 times faster than collagenase 1.

Significantly, MMP-13 has been identified in the syonvium of humans with RA and OA, as well as in human OA cartilage.

Fibrillar collagen can be damaged by helical cleavage, resulting in denaturation, or by telopeptide cleavage, leading to removal of cross-links. Two studies have demonstrated the presence of active collagenases in cartilage with polyclonal antisera specific for cryptic epitopes within the helical region of Type II collagen, which are exposed upon collagen unwinding due to collagenase cleavage, and for a collagen neoepitope generated by collagenase. These findings indicate that collagenase 1, collagenase 3, or both are involved in the cartilage degradation associated with various arthritides. Thus, the specific degradation of Type II collagen from collagenase cleavage creates neoepitopes for antibody targeting that are useful for specific targeting aspects of this invention. These neoepitopes will be located within the N-terminal ¾ fragment sequence of the alpha1(II) chain, which is known to contain epitopes to AH12L3 and CB11B (recognized by antibody COL2-¾ m).

In arthritides, the increased catabolism of the cartilage proteoglycan, aggrecan, is one of the principal pathological processes that leads to the degeneration of articular cartilage. The consequent loss of sulphated glycosaminoglycans, which are intrinsic components of the aggrecan molecule, compromises both the functional and structural integrity of the cartilage matrix. Over a period of time, this process leads to cartilage degradation. In situ degradation of aggrecan is a proteolytic process involving cleavage at specific peptide bonds located within the core protein. The most well characterised enzymatic activities contributing to this process are a result of the specific action of metalloproteinases. In vitro aggrecanolysis by matrix metalloproteinases (MMPs) has been widely studied. However, it is now well recognised that the principal proteinases responsible for aggrecan degradation in situ in articular cartilage are the aggrecanases, two recently identified isoforms of which are members of the A Disintegrin And Metalloproteinase with Thrombospondin motifs' (ADAMTS) gene family. Monoclonal antibody technologies exist to identify novel neoepitopes on aggrecan or aggrecan degradation products. Furthermore, another aspect of this invention is the use of such monoclonal antibodies or fragments thereof that bind to neoepitopes on aggrecan or aggrecan fragments to target nanoparticles containing a combination of an anabolic promoting agent and a catabolic inhibitor.

Temporal studies have established that aggrecanases are primarily responsible for the catabolism and loss of aggrecan from articular cartilage in the earlier stages of arthritic joint diseases. Although a continuum, this process appears largely to precede collagen catabolism. At a later stage in the disease process, when collagen catabolism is occurring, there is evidence for MMP-mediated degradation of the small proportion of aggrecan remaining in the cartilage.

It has been possible to develop and use monoclonal antibody technologies to identify catabolic neoepitopes on proteolytic degradation products to identify specific cleavage sites that are unique and characteristic for different families of matrix degrading enzymes. In these studies, several monoclonal antibodies were characterized that specifically identified catabolic neoepitopes (new epitopes created as specific N- or C-terminal amino acid sequences of a proteolytic cleavage product) that were generated by the action aggrecanases (or MMPs) on the interglobular (IGD) domain of aggrecan. These antibodies have been used to monitor the proteolysis of aggrecan and link proteins. Furthermore, those skilled in the art will recognize that the use of antibodies that recognize neoepitopes on degradation products of matrix proteins generated during cartilage catabolism can be used to target immunoparticles to the joint, without departing from the scope of this invention.

In another aspect of the invention, the targeting antibodies or antibody fragments specifically bind to neoepitopes or cleavage sites of aggrecan or aggrecan fragments within cartilage, particularly such neoepitopes or cleavage sites generated by the individual or combined action of MMP-1, 3, 8 or 13, or other members of the MMP protein family or a member of the ADAMTS protein family. Examples of monoclonal antibodies that recognize different structural epitopes or neoepitopes within aggrecan or aggrecan fragments are 8-A-4 or BC-3. MAb 2-B-6 has been used to detect the large number of aggrecan degradation products that result from either aggrecanase, MMP or other proteolytic activities at many sites along the core protein of aggrecan. MAb 2-B-6 recognizes 4-sulphated unsaturated dissaccharides of chondroitin sulphate that are attached to these core protein fragments. A related antibody, MAb 3-8-3, has also been used to identify different deglycosylated aggrecan metabolites containing 6-sulphated chondroiten sulfate oligosaccharides. MAb BC-3 recognizes the N-terminal neoepitope sequence defined by the amino acid sequence, alanine-arginine, glycine (ARGxx . . . ) generated after aggrecanase catabolism within the 1GD domain of aggrecan.

The ADAMTS-4 gene (Genbank NM-005099) and ADAMTS-5 gene (Genbank 007038) encode a disintegrin and a metalloproteinase with thrombospondin motifs-4 and 5, which are members of the ADAMTS protein family. Members of the family share several distinct protein modules, including a propeptide region, a metalloproteinase domain, a disintegrin-like domain, and a thrombospondin Type 1 (TS) motif. Individual members of this family differ in the number of C-terminal TS motifs, and some have unique C-terminal domains. The enzyme encoded by the ADAMTS-4 gene lacks a C-terminal TS motif. The enzyme encoded by the ADAMTS-5 gene contains 2 C-terminal TS motifs and functions as aggrecanase to cleave aggrecan, a major proteoglycan of cartilage. Thus, both of these enzymes are responsible for the degradation of aggrecan and the generation of neoepitopes on aggrecan and aggrecan fragments (Tortorella, M., et al., *J. Biol. Chem.* 275(33): 25791–25797 (2000); Tortorella, M. et al., *J. Biol. Chem.* 275(24):18566–18573 (2000); Abbaszade, I. et al., *J. Biol. Chem.* 274(33):23443–23450 (1999)).

In another embodiment of this invention for treatment of human cartilage in the setting of OA, an antibody is used that targets the early biochemical neoepitope marker of OA, termed 3-B-3(−). The 3-B-3(−) epitope is an OA-related phenotypic change in the termini of the chondroitin sulfate (glycosaminoglycan) chains of aggrecan.

c. Targeting Antibody Characteristics

As used herein, the term "antibody" is intended to include immunoglobulin molecules and immunologically active portions of immunoglobulin molecules (i.e., molecules that contain an antigen binding site that specifically binds or immunoreacts with an antigen). The term describes an immunoglobulin, whether it is naturally or synthetically produced. The proteins comprising the antibody can be derived from natural sources, or synthetically produced either in part or in whole. Examples of antibodies include all immunoglobulin subtypes and Fab and F(ab')$_2$, scFv, Fv, dAb, Fd fragments, as well as fragments disclosed in U.S. Pat. No. 5,534,254. ScFV refers to single-chain minimum binding domains of an immunoglobulin molecule. The term "antibody" is also intended to refer to an antibody that functions in the extracellular space, within the plasma membrane of a cell, or in an intracellular region of a cell (e.g., the cytoplasm or nucleus) to modulate the expression or activity of one or more genes that regulate cartilage metabolism. Preferred antibodies for use in the present invention include humanized, chimeric and human monoclonal antibodies.

In the context of an antibody, the term "fragment" refers to any sequence of amino acids that is part of any targeted polypeptide defined above, having common relevant elements of origin, structure and mechanism and functional equivalence to the whole antigen for purposes of targeting within the present invention. The calling out of an antibody in the compositions and methods described herein is also intended to include the use of fragments of such antibodies.

A preferred embodiment of the present invention employs humanized or human antibodies or fragments thereof that are covalently attached to the surface of the nanospheres or other particles in which the therapeutic chondroprotective agents of the present invention are encapsulated. Antibodies or fragments thereof are preferred as the targeting molecules on the surface of particles in which therapeutic chondroprotective agents are encapsulated, because they must be sufficiently stable in vivo and exhibit a minimum potential of being removed from the surface of the particle by serum containing extracellular fluid proteins. It is envisioned that fully human monoclonal antibodies or humanized murine antibodies, which bind to any molecules of the cartilage extracellular matrix or to cells of the joint, will be most useful as the type of joint-targeting antibodies that direct the delivery of the therapeutic agent(s) to be administered to human patients because they will not generate an immune response upon administration.

For example, a murine monoclonal antibody may be chimerized by genetically recombining the nucleotide sequence encoding the murine Fv region (i.e., containing the antigen binding sites) with the nucleotide sequence encoding a human constant domain region and an Fc region. Some murine residues may also be retained within the human variable-region framework domains to ensure proper target-site binding characteristics. Humanized antibodies for use in targeting will be recognized to have the advantage of decreasing the immunoreactivity of the antibody or polypeptide in the host recipient, and may be useful for increasing the in vivo half-life and reducing the possibility of adverse immune reactions to the conjugated antibody on the surface of the nanoparticle or other encapsulating particle.

It is highly advantageous to employ antibodies or their analogs with fully human characteristics for treatment of human patients. Methods may be employed which are similar to those disclosed in U.S. Pat. Nos. 6,075,181, 6,235,883 and 6,492,160 and Patent Application EP 1 167 537 A1, the disclosures of which are hereby expressly incorporated by reference. Such methods previously have been used to generate a variety of fully human antibodies against human IL-8 and epidermal growth factor receptor. In the most preferred embodiments of the present invention, the antibody or antibody fragment binds to a target epitope with dissociation constant in the range of 0.1 to 10 nanomolar.

While fully human or humanized antibodies are preferred for use in the present invention to treat human patients, it should also be understood that the methods and compositions of the present inventions are also useful in veterinary applications to treat other mammals susceptible to joint degeneration, (e.g., horses and dogs).

d. Chondroprotective Agents for Targeted Delivery

A preferred aspect of the targeted embodiment of the present invention will include at least one chondroprotective agent that is encapsulated or contained within a nanoparticle or other delivery vehicle to which a targeting antibody, antibody fragment or other targeting structure is attached. The encapsulated or contained agent may be any one of anabolic chondroprotective agents or catabolic inhibitory agents disclosed herein having chemical or structural characteristics rendering it amenable to encapsulation or containment in a selected nanoparticle or other delivery vehicle. Additionally, agents that would otherwise be highly susceptible to metabolic degradation from systemic administration (e.g., proteins and peptides) or that cause harmful side effects if administered systemically without targeting are preferable for targeting. For example, each of the classes of anabolic chondroprotective agents disclosed herein below (including members of the transforming growth factor (TGF)-$\beta$ superfamily, including TGF-$\beta$ agonists and bone morphogenetic protein agonists, insulin-like growth factors and fibroblast growth factors) and certain of the classes of catabolic inhibitory agents disclosed herein below (Interleukin-1 receptor antagonists and TNF-$\alpha$ receptor antagonists) are proteins, and as such are well suited for delivery in targeted encapsulated form.

A most preferred targeted encapsulated composition of the present invention will include both an anabolic chondroprotective agent and a catabolic inhibitory chondroprotective agent encapsulated in the same targeted immunoparticles (or other targeted particles), preferably both agents being proteins. Alternately, each agent may be separately encapsulated, and an admixture of the two (or more than two) types of targeted particles may be administered, or less preferably the two or more targeted agents may be delivered separately, either concurrently or sequentially, to result in coincident presence of the agents within the joint.

In some instances either only the anabolic chondroprotective agent or the catabolic inhibitory agent may be amenable to encapsulation, or one agent may not be associated with undesirable systemic side effects. In such instances, one agent may be delivered in encapsulated targeted form, while the other agent is delivered in non-targeted, non-encapsulated form, either together in the same dosage form as an admixture, or separately.

While not as preferred as administering both an anabolic agent and a catabolic inhibitory agent, given all of the advantages provided by this combination described above, the delivery of a single chondroprotective agent (either anabolic-promoting or catabolic inhibitory) encapsulated within an immunoparticle that targets an antigen localized within the joint is also possible.

e. Encapsulation of Agents

The size of a substance is a major factor determining whether it can permeate the wall of synovial capillaries and move from the systemic circulation into the joint. The maximum diameter of particles that can move across the synovial capillary wall is generally regarded to be 50 nanometers. However, some studies of the permeability of the synovial capillaries of the rat using lecitihin-coated polystyrene particles up to 240 nanometers in diameter can be transported across synovial capillary walls via transcytosis. The present invention overcomes the limitation imposed by the synovial permeability barrier by preferably employing a class of encapsulation particles (e.g., nanoparticles (preferably nanospheres)), which are constrained in size distribution.

Sustained release dosage forms of the invention may comprise microparticles and/or nanoparticles having therapeutic agents dispersed therein, or may comprise the therapeutic agent in pure, preferably crystalline, solid form. The therapeutic dosage forms of this aspect of the present invention may be of any configuration suitable for sustained release. Preferred sustained release therapeutic dosage forms of the present invention will have the following size, biodegradation and biocompatibility characteristics.

The targeted delivery system of the present invention preferably utilizes nanoparticles that are limited in size from about 5 nanometers to about 750 nanometers in diameter, with about 10 to about 500 nanometers being more preferred, most preferably from about 20 to about 200 nanometers. Alternately useful but less preferred, if demonstrated to result in sufficient permeability in the diseased state, are microparticles that range in size from about 1 micrometer to about 100 micrometers in diameter, with about 1 to about 25 micrometers being more preferred; more preferably from about 1 to about 10 micrometers.

Preferred particles are biodegradable structures that biodegrade and release loaded drug at therapeutic levels over a period of time preferably between from about 1 to about 150 days, preferably from about 7 to about 60 days, with from about 14 to about 30 days being more preferred. It is understood by those in the art that drug release from nanoparticles and microparticles may occur by a combination of physical processes, which include, but are not limited to, diffusion and degradation and may be described by complex kinetic processes that are unique to each carrier formulation and combination of anabolic and anti-catabolic therapeutic agents.

Preferred particles are biocompatible with targeted tissues of the joint and the local physiological environment into which the dosage form is administered, including yielding biocompatible biodegradation products. Suitable compositions include biodegradable particles formulated from natural polymers, including hyaluronan, chitosan, collagen, gelatin and alginate. These natural polymers may be combined with other polymers to produce copolymer particles composed of, for example, chitosan and gelatin. Synthetic biodegradable poly(alpha-hydroxy esters) such as polylactic acid (PLLA), polyglycolic acid (PGA) and the copolymer PLGA have been used successfully for the production of microparticles that incorporate protein therapeutics, such as human growth hormone. Another example of a biodegradable polymer that may be suitable for use in preparing targeted particles of of the present invention are amphiphilic ABA triblock copolymers such as poly(ethylene oxide):poly (3-hydroxybutyrate):poly(ethylene oxide).

In selecting a polymer nanoparticle system for use with selected chondroprotective agents of the present invention, it is also important to ensure adequate bioactivity of the encapsulated drug.

The use of targeted, biodegradable polymeric nanospheres has the advantage of providing selected differential release profiles for the encapsulated therapeutic agents. For some drug combinations, the optimal release kinetics may consist of a dual-release process, wherein each active agent demonstrates a different sustained release kinetic profile to provide the most optimal drug pharmacokinetics within the joint. Those skilled in the art will recognize, based on the disclosure herein, that the optimal release kinetics from the nanoparticles or microparticles will vary for each individual drug, and will also be a function of the amount of drug loaded into particles during formulation, the size of the particles, and other physiochemical properties that are determined by the composition of the particles. Quantitative release rates for each drug from the encapsulating particles resident in the joint will be adjusted to obtain the optimal therapeutic concentration in the synovial fluid and intra-articular space to achieve the desired therapeutic concentrations. In vitro studies can be conducted to characterize the dual-release kinetics for the sustained release formulation in which each component (e.g., the anabolic drug and the catabolic inhibitor) demonstrate sustained release over a period of 7–30 days, by way of example. Methods to quantitate the amount of each drug released into the synovial fluid are well known in the art, and may include measurements of radioactively labeled drug. Alternatively, it is possible to covalently attach fluorescent or other optical reporter molecules to prepare labeled drugs. Those skilled in the art will recognize that many indirect methods for quantitation exist, such as ELISAs or mass-spectrometry, which are specific to each agent.

For practical reasons, it is difficult to achieve similar release kinetics for two drugs that vary substantially in size, as is the case for many of the anabolic and catabolic combinations. For example, in one preferred embodiment of this invention, it is desirable to deliver a catabolic inhibitor such as a p38 MAP kinase inhibitor that may be characterized by a molecular weight of 200–500 (for example, SB203580, MW=377) with an anabolic agent, such as human IL-10, which is 160 amino acids in length and has a MW of approximately 18 Kda. Independent control of the sustained release rates for each agent can be achieved by varying the structural composition of the particles and/or by creating an admixture of two or more immunoparticles. In the admixture, one set of particles is homogeneous with respect to the encapsulated anabolic agent, while a distinct set of particles is homogeneous with respect to the encapsulated catabolic inhibitor. The two sets of admixed particles may vary in their respective sizes and polymeric composition, but will be characterized, if appropriate, by similar release rates for their active agents, or by release rates that are consistent, optimizing the local therapeutic effects of each of the encapsulated agents, respectively.

Liposomes are not preferred delivery vehicles for the targeted systemic delivery of chondroprotective agents in accordance with the present invention. Relative to nanospheres and other sustained release particle delivery systems, liposomes have a short half-life within the circulatory system. Liposome drug conjugates may be trapped in the liver and spleen, resulting in liposomal breakdown and release of the active agents. The agents are thus distributed systemically in the active state rather than being protected until localized within the joint. The release of agents from targeted liposomal delivery systems is not highly sustained and is much less localized than for targeted immunoparticle delivery systems. For these reasons, the use of particles (e.g., nanospheres) is highly preferred relative to the use of liposomes. None the less, for systemically delivered anabolic chondroprotective agents, or combinations of chondroprotective agents including an anabolic agent, for which targeting is highly desired, targeted liposomes may prove to be suitable and offer advantages relative to naked drug delivery.

f. Coupling of Antibodies to Encapsulated Agents

Representative "coupling" methods for linking the targeting antibody to the sustained release nanoparticle through covalent or non-covalent bonds include chemical cross-linkers and heterobifunctional cross-linking compounds (i.e., "linkers") that react to form a bond between reactive groups (such as hydroxyl, amino, amido, or sulfhydryl groups) of the targeting antibody and other reactive groups (of a similar chemical nature) that are present on the surface of the nanoparticle or other targeting vehicle. This bond formed between the targeting antibody and the particle or other delivery vehicle may include but is not limited to the following: a peptide bond, a disulfide bond, a thioester bond, an amide bond and a thioether bond Direct conjugation of sustained release dosage forms to the targeting protein (antibody) may disrupt recognition of the targeted molecule or cell by the modified targeting antibody. Ligand sandwich attachment techniques are useful alternatives to achieve attachment of the sustained release dosage form to the targeting binding proteins (antibodies). These techniques may involve the formation of a primary peptide or protein shell using a protein that does not bind to the target cell population. Binding protein is then bound to the primary peptide or protein shell to provide the resultant particle with functional binding protein/peptide. An exemplary ligand sandwich approach involves covalent attachment of avidin or streptavidin to the particles through functional groups as described above with respect to the "direct" binding approach. The binding protein is derivatized, preferably minimally, via functionalized biotin (e.g., through active ester, hydrazide, iodoacetal, maleimidyl or like functional groups). Ligand (i.e., binding peptide or protein/functionalized biotin) attachment to the available biotin binding sites of the avidin/streptavidin primary protein shell occurs through the use of a saturating amount of biotinylated protein/peptide.

3. Alternative Targeting and Preferential Effect Delivery Methods

Other methods of targeting the chondroprotective agents and combinations thereof in the present invention, or in achieving preferential effectiveness of such agents or combinations at the joint relative to other sites of the body, are also within the scope of the present invention. For example, the two principle cell types of the synovium, macrophage synoviocytes (Type A) and fibroblast synoviocytes (Type B), and chondrocytes are known to express a variety of unique proteins that are present on the surfaces of these cells, and that could serve as epitopes for specific cellular targeting. Selecting agents, and preferably a combination of an anabolic-promoting agent and a catabolic inhibitory agent, that are directed to proteins that are preferentially expressed in the joint, or that are preferentially expressed in an inflamed or diseased joint, may preferentially increase local effect while minimizing unwanted systemic effects.

As discussed above, molecular targets within the joint may include components of the cartilage extracellular matrix, such as cartilage specific collagens, including collagen Type II, IX, X, XI, aggrecan and other small leucine-rich proteoglycans (e.g., decorin, biglycan, fibromodulin and lumican). Also included as targets are cartilage oligomeric matrix protein (COMP) and glycoprotein-39 (HC-gp39), also termed YKL-40. A desirable target for use in this aspect of the invention would be a biochemical cartilage marker that may be either absent from normal adult cartilage, or present at very low levels, but that is present in certain stages of either RA or OA. Likewise, selection of chondroprotective agents, and preferably a combination of an anabolic-promoting agent and a catabolic inhibitory agent that are specific to receptors that are upregulated in the diseased or inflamed state, may also preferentially increase local effect relative to other areas of the body.

As noted above, an encapsulated agent or agents may be targeted to one or more structures within the joint by coupling the encapsulated agent to a corresponding targeting antibody (or antibody fragment). Potentially such antibodies may also be coupled to the naked drugs themselves, using a linkage that is cleaved within the local environment of the joint to achieve targeting and delivery of the systemically administered drugs to the joint. Similarly, the chondroprotective agents that are included in an anabolic-promoting and catabolic inhibitory composition of the present invention may be selected such that they preferentially act on sites within the joint, relative to the rest of the body, thereby preferentially exerting their effects on synoviocytes and/or chondrocytes and/or components of the extracellular matrix.

E. Methods for Selection of Delivery Vehicles and Dosage

The specific nanosphere system and targeting antibody or fragment to be used in accordance with the present invention to deliver selected agents, and the precise loading or dosage of therapeutic agents to include in the targeted compositions, may be determined analytically in accordance with the invention. The analytical method includes administering an antibody-labeled nanosphere (or other targeted particle) containing encapsulated therapeutic agents to a patient in need of such a diagnostic test, and subjecting the patient to imaging analysis to determine the location of the drug-containing nanospheres. The extent of deposition in the joint of a patient may then be determined by using imaging analysis. Imaging analysis is well known in the medical art, and includes, without limitation, x-ray analysis, magnetic resonance imaging (MRI) or computed tomography (CT). In a preferred embodiment, the joint-targeting antibodies may be labeled with a detectable agent that can be imaged in a patient. For example, the targeting antibody may be labeled with a contrast agent, such as barium, which can be used for x-ray analysis, or a magnetic contrast agent, such as a gadolinium chelate, which can be detected using MRI or CT. Other labeling agents include, without limitation, radioisotopes, such as $^{99}$Tc. In additiona to imaging analysis, a biopsy can be obtained from the patient to determine the presence and concentration of the particles in the joint (e.g., synovial tissues).

The local delivery embodiment of the present invention was described in terms of suitable concentrations for the therapeutic agents when delivered locally, sufficient to provide a predetermined level of inhibitory or therapeutic effect at the local delivery site (e.g., the joint). When delivered systemically, a greater concentration or dosage of the agents will need to be administered. This systemic dosage and/or concentration is that which is required to result, after any metabolic transformation processes, in the supply of sufficient active agent(s) at the desired site(s) of potential cartilage degradation necessary to achieve a desired level of local therapeutic effect. In particular, suitable therapeutic and preferred levels for systemic dosages and/or concentrations are those which result in the supply of active agents at the local site (e.g., the joint) at a concentration level that is within the local delivery therapeutic and preferred concentration ranges, respectively, previously described.

For targeted sustained release delivery systems, a sufficient dosage or load of the agent is included in the composition to result in a local concentration at the joint or site of action over a predetermined sustained release period that achieves a desired level of therapeutic effect over the substantial duration of the desired sustained release period. Thus a sufficient dosage or load of the agent is included to result in a predetermined amount of the encapsulated agent that is taken up by the joint, accounting for any metabolic transformation of the agent that occurs before reaching the joint or in the local environment of the joint. This predetermined amount of encapsulated agent reaching the joint will be determined in accordance with the disclosure contained herein such that as the nanosphere or other encapsulating delivery system degrades, agent is released at the local site of action to provide a local concentration that is within the therapeutic concentration range for that agent during a desired period of sustained release (e.g., over a period of 1 day to 4 weeks, more preferably between 1 day and 2 weeks).

IV. Agents for the Inhibition Of Cartilage Degradation

The following is a description of exemplary classes of chondroprotective agents, and exemplary drugs within each class, that are suitable for use in the compositions of the present invention. While not wishing to be limited by theory, the justification behind the selection of the various classes of agents that is believed to render the agents operative is also set forth.

1. Interleukin-1 (IL-1) Receptor Antagonists

The interleukin IL-1 exists in two forms, IL-1α and IL-1β, which are polypeptides derived from separate gene products that share a similar spectrum of immunoregulatory and pro-inflammatory functions. IL-1 is a 17 kD polypeptide that can both act upon and be produced by a number of cell types in the joint, including synovial fibroblasts and macrophages, chondrocytes, endothelial cells and monocytes and macrophages. There is substantial evidence that IL-1 plays a pivotal role in joint inflammation and in the pathophysiological loss of articular cartilage that occurs in the injured joint.

The actions of both forms of this cartilage destructive cytokine are mediated by one of two IL-1 receptors (IL-1R), Type I IL-1 or Type II IL-1 receptors. IL-1 receptors are structurally distinct and belong to a separate superfamily characterized by the presence of immunoglobulin binding domains. These receptors bear close amino acid homology with other receptors containing immunoglobulin domains. Expression of the larger Type I IL-1 receptor is present on T cells and fibroblasts while the smaller Type II IL-1 receptor is present on B cells, monocytes, neutrophils, and bone marrow cells.

Type II IL-1 receptors bind IL-1β with high affinity, but IL-1β binding does not initiate intracellular signal transduction as it does upon binding to the Type I IL-1 receptor. In contrast, the Type II receptor serves as a precursor for a soluble IL-1 binding factor that has been shown to be shed from cells and this soluble receptor acts as a physiological IL-1β antagonist. A naturally occurring IL-1 binding protein has been described which corresponds to the soluble external portion of the Type II receptor.

A naturally occurring secreted, soluble ligand that binds to IL-1 receptors, alternatively referred to as the IL-1 receptor antagonist (sIL-1RA, IL-1Ra, IL-1ra), has been cloned, sequenced and found to encode a 22 kD protein. IL-1Ra competitively inhibits the binding of IL-1α and IL-1β to both Type I and II IL-1 receptors. IL-1Ra is a pure receptor antagonist since its binding to the receptor does not activate the cellular signal transduction machinery of membrane associated IL-1 receptors. Despite high affinity binding of this protein to the IL-1Rs, a 10–100 fold molar excess is required to inhibit IL-1 biological responses of cells that express the Type I IL-1R. Cells known to produce IL-1Ra include monocytes, neutrophils, macrophages, synoviocytes and chondrocytes. IL-1Ra has been shown to inhibit PGE$_2$ synthesis, induction of pro-inflammatory cytokines and MMPs, and nitric oxide production. Secreted IL-1Ra is released in vivo during experimentally induced inflammation. Importantly, IL-1Ra is expressed in synovial tissue and is present in normal human synovial fluid. In patients with knee injuries, levels of IL-1Ra in the synovial fluid dramatically increase in the acute phase after injury, and subsequently decrease to below normal levels in sub-acute and chronic states. Thus, the IL-1Ra has been shown to play a physiological role in responses of the joint to injury.

IL-1 is considered the dominant cartilage destructive cytokine that plays a pivotal role in joint destruction due to its ability to stimulate the production of degradative enzymes and pro-inflammatory cytokines by both chondrocytes and synoviocytes. Moreover, IL-1β is a potent inhibitor of proteoglycan and collagen synthesis by chondrocytes. At the cellular level, IL-1β-induced responses of synovial fibroblasts include increased production of PGE2, collagenase and other neutral proteases and the upregulation of pro-inflammatory cytokines, IL-6 and IL-8.

IL-1, which is present in the joint fluid of patients with arthritic diseases, stimulates chondrocytes to: 1) synthesize elevated amounts of enzymes such as stromelysin, fibroblast and neutrophil collagenase and plasminogen activator, and 2) inhibit synthesis of plasminogen activator inhibitor-1 and TIMP. In addition, IL-1β is a potent inhibitor of the synthesis of matrix constituents such as Type II collagen, the predominant form of collagen in articular cartilage, and proteoglycans. The imbalance between the levels of inhibitors and proteases leads to an increase in the amount of active proteases. This increase, combined with a suppression of matrix biosynthesis, results in degradation of cartilage. In animal studies, injection of IL-1 into rabbit knee joints causes depletion of proteoglycan from the articular cartilage.

Since IL-1 is one of the key cytokines involved in the pathogenesis of chronic synovitis and cartilage degradation, reducing its production or blocking its action represents an appropriate strategy for new treatments to reduce synovial inflammation and to provide a chondroprotective effect. A variety of therapeutic approaches for antagonizing the interaction of the agonist, IL-1, with its natural membrane bound receptor can be utilized which include: 1) naturally occurring specific inhibitors of IL-1 activity that have been characterized to date, including IL-1Ra and soluble IL-1 receptors; 2) anti-IL-1 Abs; and 3) small molecule antagonists which may be either peptidic or nonpeptidic.

The ability to block the actions of this key cytokine will have effects on many cell types in the joint (e.g., synovial fibroblasts and chondrocytes), thus inhibiting subsequent pathological effects such as infiltration of inflammatory cells into the joint, synovial hyperplasia, synovial cell activation, as well as cartilage breakdown and inhibition of cartilage matrix synthesis. An IL-1 receptor antagonist should block the propagation of the inflammatory response by IL-1 and thereby interrupt the disease process. The therapeutic potential of a number of IL-1 receptor antagonists have been established in animal models of inflammation and arthritis (RA and OA). Patients suffering from RA have improved clinically following a subcutaneous injection of IL-1Ra or an intra-articular injection of soluble Type I IL-1R.

The effects of IL-1β and IL-1Ra depend on their respective local concentrations. In the supernatants of RA synovium pieces, IL-1β levels were threefold higher than those of IL-1Ra. Thus, the spontaneous local production of IL-1Ra is not sufficient to inhibit IL-1β effects because a larger (10 to 100-fold) molar excess of IL-1Ra is required to inhibit IL-1-induced biological responses in cells that express Type I IL-1R. Thus, high doses of IL-1Ra have been used in vivo to block IL-1 in human volunteers in patients with RA. IL-1Ra present locally in the synovium provides a negative signal, down-regulating at least part of the IL-1-mediated processes in synovitis, such as leukocyte accumulation in the inflamed tissue, $PGE_2$ production and collagenase production by synovial cells. A chondroprotective effect of IL-1Ra has been demonstrated using direct injection of IL-1Ra into the joint in a canine ACL model and by employing a gene therapy approach based upon transfection of the IL-1Ra gene into human synovial fibroblasts.

The present invention discloses local and systemic delivery of an IL-1 soluble receptor protein, which is comprised of an extracellular domain of a IL-1R, and which is capable of binding an IL-1 cytokine molecule in solution. In particular, and by way of example, a soluble human IL-1 receptor (shuIL-1R) polypeptide comprising essentially the amino acid sequence 1–312, as disclosed within U.S. Pat. No. 5,319,071 and U.S. Pat. No. 5,726,148, is disclosed herein for use in combination with one or more drugs chosen from either an anti-inflammatory class, anti-pain class, or chondroprotective class. Alternatively, the local or systemic delivery of a fusion protein consisting of the sIL-1R binding domain polypeptide is proposed for use to promote chondroprotection, as disclosed in U.S. Pat. No. 5,319,071. In addition, the local or systemic delivery of an IL-1 receptor antagonist as disclosed within U.S. Pat. No. 5,817,306 is disclosed for use in the present invention. The shuIL-1R soluble receptor has been shown to bind IL-1 with nanomolar affinity. Local delivery of a therapeutically effective concentration of an IL-1R soluble receptor, such as shuIL-1R, may occur by direct injection of the joint or in an irrigation solution (e.g., during an arthroscopic surgical procedure) in combination with one or more chondroprotective drugs, anti-inflammatory drugs, or anti-pain drugs and is disclosed herein as a cartilage protective agent when applied locally to tissues of the joint in a variety of inflammatory or pathophysiological conditions. Alternately such agents may be delivered systemically, such as in a targeted systemic delivery system. Such treatment will preemptively inhibit IL-1 stimulation of production of collagenase-1 and stromelysin-1. Employing a wholly different method based on gene delivery for local production of Type 1 soluble receptors for IL-1 and/or TNF-α, it has been found that the presence of soluble receptors for these cytokines are able to confer protection to the rabbit knee joint during the acute inflammatory phase of antigen induced-arthritis.

IL-1 receptor antagonist peptides (11–15 amino acids) that bind specifically with high affinity to the human Type I IL-1 receptor are suitable for use in the present invention as chondroprotective agents. These small peptides provide a number of advantages over larger recombinant IL-1 soluble receptors or recombinant IL-1ra, including ease and cost of synthesis and the ability to penetrate biological barriers. Two of the most potent peptides, based on in vitro efficacy are: Ac-FEWTPGWYQJYALPL-$NH_2$ (AF12198, $IC_{50}$=0.5–2 nM) and Ac-FEWTPGWYQJY-$NH_2$ (AF11567). AF11567 is a truncated version of AF12198, lacking the 4 C-terminal residues and exhibiting slightly lower affinity for the Type I IL-1 receptor but possessing a similar plasma half-life of 2.3–2.6 hrs. Poor solubility and rapid metabolism appeared to limit the in vivo efficacy of AF12198 when administered systemically via intravenous infusion. These limitations are in part overcome through direct, local delivery methods such as injection into the intra-articular joint space or by inclusion in the surgical irrigation fluid or other infusion, or through systemic delivery using targeted delivery vehicles, as described above. Examples of IL-1 receptor antagonist agents suitable for the present invention are listed below. For all modes of local delivery (i.e., injection, infusion and irrigation) and systemic delivery (including though use of a targeted delivery system) the optimal dose and/or concentration of each suitable agent is that which is therapeutically effective. As an example, for each of the listed agents, the preferred and most preferred concentrations of an irrigation solution containing the listed agent are provided. Such concentrations are expected to be therapeutically effective. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 1

Therapeutic and Preferred Concentrations of Interleukin-1 Receptor Antagonists

| Compound | Local Delivery Therapeutic Concentrations (nM) | Most Preferred Local Delivery Concentrations (nM) |
| --- | --- | --- |
| rshuIL-1R | 0.2–2000 | 200 |
| rhIL-1ra | 0.2–2000 | 200 |
| anti-IL1-antibody | 0.2–2000 | 200 |
| AF12198 | 0.2–2000 | 200 |
| AF11567 | 0.2–2000 | 200 |

2. Tumor Necrosis Factor (TNF) Receptor Antagonists

TNF-α, a cytokine mainly produced by activated macrophages, has many biological actions including transcriptional regulation of several genes that are mediated by specific TNF receptors, as well as immunoregulatory activities. Originally, two different receptors termed TNF-R1 and TNF-R2 were cloned and characterized and also found to be produced as soluble receptors.

Receptors in this family are single transmembrane proteins with considerable homology in their extracellular domains whereas their relatively short intracellular domains bear very little sequence homology. The actions of TNF are the result of the factor binding to cell surface receptors that are present on virtually all cell types that have been studied. Two receptors have been identified and cloned. One receptor Type, termed TNFR-II (or Type A or 75 kDa) encodes a transmembrane protein of 439 amino acids and has an apparent molecular weight of 75 kDa. The second receptor type, termed TNFR-I (or Type B or 55 kDa) shows an apparent molecular weight of 55 kDa and encodes a transmembrane protein of 426 amino acids. TNFR1 contains an intracellular domain that can initiate signaling through the NF-κB pathway.

Both of the TNF receptors exhibit high affinity for binding TNFα. Soluble TNF receptors (sTNFR) have been isolated and proved to arise as a result of shedding of the extracellular domains of the membrane bound receptors. Two types of sTNFR have been identified and designated as sTNFR1 (TNF BPI) and sTNFRII (TNF BPII). Both of these soluble receptor forms have been shown to represent the truncated forms of the two types of TNFR described above.

TNF-α plays a central role in the sequence of cellular and molecular events underlying the inflammatory response and cartilage destruction. Many of the effects of TNF-α overlap with the pro-inflammatory effects of IL-1. Among the pro-inflammatory actions of TNF-α is its stimulation of the release of other pro-inflammatory cytokines including IL-1, IL-6 and IL-8. TNF-α also induces the release of matrix metalloproteinases from neutrophils, fibroblasts and chondrocytes that degrade cartilage, in part through the stimulation of collagenase. Furthermore, TNF-α upregulates COX-2 in normal human articular chondrocytes and synovial fibroblasts, resulting in increased PGE2 production.

This cytokine, along with IL-1, is considered to initiate and produce pathological effects on cartilage in the joint, including leukocyte infiltration, synovial hyperplasia, synovial cell activation, cartilage breakdown and inhibition of cartilage matrix synthesis. In particular, during synovial inflammation, increased levels of TNF-α are found in synovial fluid of joints and increased production of TNF-α by synovial cells occurs. Thus, systemic delivery, including in a targeted delivery system, or local delivery of a soluble TNF-α receptor in an irrigation solution, infusion, or injection will bind free TNF-α and function as an antagonist of TNF receptors in the surrounding tissue, thus providing a cartilage protective effect.

The present invention describes the use of functional antagonists of TNF-α that act extracellularly to block interaction of the ligand with their cognate membrane receptors either by scavenging of available free ligand or by direct competitive interaction with the receptor itself, alone or in combination with other agents to provide a chondroprotective effect. A variety of therapeutic approaches for antagonizing the interaction of the agonist, TNF-α, with its natural membrane bound receptor can be utilized which include: 1) the use of naturally occurring specific inhibitors of TNF-α activity that have been characterized to date, including soluble TNF-α receptors; 2) the use of anti-TNF-α antibodies and 3) the use of small molecule antagonists which may be either peptidic or nonpeptidic.

The present invention discloses the use of a chimeric soluble receptor (CSR) protein, in which the extracellular domain of a TNF receptor, which possesses binding activity for a TNF molecule, is covalently linked to a domain of an IgG molecule. In particular, and by way of first example, a chimeric polypeptide (recombinant chimera) comprising the extracellular domain of the TNF receptor extracellular polypeptide coupled to the CH2 and CH3 regions of a mouse IgG1 heavy chain polypeptide could be used, as disclosed in U.S. Pat. No. 5,447,851. The chimeric TNF soluble receptor (also termed the "chimeric TNF inhibitor" in U.S. Pat. No. 5,447,851) has been shown to bind TNF-α with high affinity and has been demonstrated to be highly active as an inhibitor of TNF-α biological activity. In addition, a second example is a chimeric fusion construct comprised of the ligand binding domain of the TNF receptor with portions of the Fc antibody (termed Fc fusion soluble receptors) that have been created for TNF-α receptors. The present invention also discloses the use of a soluble TNF receptor: Fc fusion protein, or any modified forms, as disclosed in U.S. Pat. No. 5,605,690. The molecular form of the active soluble receptor fusion protein can be either monomeric or dimeric. Existing studies establish that such a soluble TNF receptor: Fc fusion protein retains high binding affinity for TNF-α.

Within the context of defining soluble receptors as pharmacological antagonists, the term soluble receptors includes, but is not limited to: (1) soluble receptors which correspond to naturally (endogenous) produced amino acid sequences or soluble fragments thereof consisting of an extracellular domain of full-length membrane receptor, (2) recombinant soluble receptors which are truncated or partial sequences of the full length, naturally occurring receptor amino acid sequences which retain the ability to bind cognate ligand and retain biological activity and analogs thereof, and (3) chimeric soluble receptors which are recombinant soluble receptors comprised of truncated or partial sequences corresponding to a portion of the extracellular binding domain of the full length receptor amino acid sequences attached through oligomers (e.g., amino acids) to a sequence corresponding to a portion of an IgG polypeptide (e.g., IgG hinge and Fc domain) which retain biological activity and the ability to bind cognate ligand.

Soluble, extracellular ligand-binding domains of cytokine receptors occur naturally in body fluids and are thought to be involved in the regulation of the biologic activities of cytokines. The naturally occurring existence of soluble, truncated forms of a number of hematopoietic cytokine receptors has been reported (IL-1R, IL-4R, IL-6R, TNFR). For example, soluble TNFR is found at concentrations of about 1–2 ng/ml in the serum and urine of healthy subjects. Lacking signal transduction functions, these cytokine binding proteins arise as a result of alternative splicing of the mRNA for the complete receptor sequence (membrane-bound form) or as a result of proteolytic cleavage and release of the membrane-bound form of the receptor. Although the in vivo functions of these soluble truncated receptors are not fully established, they appear to act as physiological antagonists of their complementary endogenous cytokines. This antagonism occurs because (1) scavenging of the free ligand through binding to its cognate soluble receptor reduces the effective free concentration available to the membrane-bound receptors and (2) actions of the cytokines are only produced subsequent to binding to cell surface receptors.

The TNF-α soluble receptor will function as a natural antagonist of the TNF-R1 and TNF-R2 by competing with these cell surface receptors for common pool of free ligand. Pharmacologically, the TNF soluble receptor will function as an antagonist through its ability to decrease free ligand bioavailability rather than by a mechanism of competitive inhibition (i.e., competing with an endogenous ligand for a common binding site on a membrane receptor). Addition of a therapeutically effective amount of the TNF soluble receptor to the joint should effectively neutralize the biological activity of the ligand. Experiments in which recombinant soluble receptors have been administered in vivo have demonstrated the capacity to inhibit inflammatory responses and act as antagonists.

In this invention, agents suitable as chondroprotective agents for use in combination with other chondroprotective, anti-pain and/or anti-inflammatory agents to inhibit cartilage destruction include soluble TNFR, the human chimeric polypeptide (recombinant chimera) comprising the extracellular domain of the TNF-α receptor (p80) linked to the Fc portion of human IgG1, and the anti-TNF-α antibody. For all modes of local delivery (i.e., injection, infusion and irrigation) the optimal dose and/or concentration of each suitable agent is that which is therapeutically effective. As an example, for each of the listed agents, the preferred and most preferred concentrations of an irrigation solution containing the listed agent are provided, such concentrations expected to be therapeutically effective. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 2

Therapeutic and Preferred Concentrations TNF-Receptor Antagonists

| Compound | Local Delivery Therapeutic Concentrations (nM) | Most Preferred Local Delivery Concentrations (nM) |
| --- | --- | --- |
| STNFR | 0.1–2000 | 200 |
| chimeric rhTNFR:Fc | 0.1–2000 | 200 |
| anti-TNF-α antibody | 0.2–2000 | 200 |

3. Interleukin Receptor Agonists

Some cytokines are signaling glycoproteins that are important mediators of synovial inflammation and cartilage destruction. Recent analysis of the mechanism of cartilage destruction suggests that not only is the absolute level of pro-inflammatory master cytokine, IL-1, important in determining loss of cartilage, but that cytokine control of cartilage homeostasis is governed by the balance of catabolic and anabolic regulatory cytokines, and anabolic growth factors. If the balance between IL-1β and IL-1Ra production is altered in the inflammatory state in favor of IL-1β, then it will contribute to the pathogenesis of chronic inflammatory conditions and cartilage destruction, such as is known to occur after knee joint surgery. Potential therapeutic agents that would inhibit production of the pro-inflammatory cytokines at the sites of inflammation within the joint include the anti-inflammatory cytokines, IL-4, IL-10, and IL-13. These cytokines have been observed to greatly reduce articular cartilage destruction in vitro and in vivo via their effect on a range of pathways that reduce the impact of IL-1. Thus, anti-inflammatory cytokines such as IL-4, IL-10, and IL-13, may be useful in reducing inflammation by: 1) reducing the production of pro-inflammatory cytokines, and 2) inducing the production of natural anti-inflammatory cytokines such as IL-1Ra, as recently demonstrated in vivo for 1-4.

IL-4 appears to attenuate the inflammatory process in the synovium of rheumatoid arthritis (RA) patients. In rheumatoid synovium, IL-4 has been shown to inhibit the production of pro-inflammatory cytokines by pieces of synovium, to inhibit proliferation of synoviocytes and decrease bone resorption. IL-4 may promote a direct chondroprotective effect through suppression of matrix metalloproteinase-3 (MMP-3) synthesis in human articular chondrocytes. A cell culture system employing human articular chondrocytes was used to evaluate the effect of IL-4 on IL-1-induced production of MMP-3 and tissue inhibitor of metalloproteinase-1 (TIMP-1). It was found that IL-4 suppressed IL-1-stimulated MMP-3 protein and enzyme activity. In addition, IL-4 suppressed IL-1-induced MMP-3 mRNA. Induction of iNOS can be inhibited by IL-4, IL-10 and IL-13. Thus, IL-4 may be characterized as a protective mediator of joint destruction seen in inflammatory joint diseases.

Furthermore, the effects of IL-4 on the balance of IL-1 regulatory cytokine levels have also been found to support a cartilage protective role. IL-4 and IL-10 were found to suppress the production of inflammatory cytokines by freshly prepared rheumatoid synovial cells. While each interleukin was effective alone, the combination of IL-4 and IL-10 synergistically inhibited the IL-1 and TNF-α stimulated production of IL-6 and IL-8, without effects on cell viability. The addition of IL-4 to RA synovium cultures increased the production of IL-1Ra and decreased that of IL-10. In vivo treatment with IL-4 has recently been reported to promote a reduction in rat experimental arthritis by acting differentially on the IL-1β/IL-1Ra balance. IL-13, another cytokine that shares many properties with IL-4, also induced IL-1Ra in RA synovium. Therefore, the systemic or local delivery of an IL-4 and IL-13 combination may provide a synergistic therapeutic value.

IL-10 has a number of properties that indicate that it is a good candidate to inhibit cartilage destruction. It inhibits both IL-1 and TNF-α release and stimulates TIMP-1 production while inhibiting MMP-2. The production of IL-10 inside the RA synovium has recently been reported and anti-inflammatory effects of IL-10 have been characterized. IL-10 suppressed IL-11 production in an ex vivo RA model using pieces of synovium, but to a lesser extent than IL-4.

A protective effect of IL-4 and IL-10 treatment on cartilage destruction has been found in animal models of arthritis employing non-local methods of delivery for the cytokines. In a murine collagen-induced arthritis model, combination treatment of IL-4 and IL-10 produced substantial improvement. In addition to suppression of macroscopic signs of inflammation, combined treatment with IL-4 and IL-10 also reduced cellular infiltrates in the synovial tissue and caused pronounced protection against cartilage destruction. Moreover, levels of mRNA for TNF-α and IL-1 were highly suppressed both in the synovial tissue and in the articular cartilage. In contrast, levels of IL-1 receptor antagonist (IL-1Ra) mRNA remained elevated, which suggests that the mechanism of protection may be related to suppressed production of TNF-α and IL-1, with concomitant up-regulation of the IL-1Ra/IL-1 balance. These data are consistent with a dominant role of IL-10 in the endogenous suppression of the inflammatory response and destruction of articular cartilage, and a combined treatment with IL-4 and IL-10 appears of potential therapeutic value.

The role of endogenous IL-4 and IL-10 and the therapeutic effect of addition of these cytokines on joint inflammation and cartilage destruction in the early stages of the macrophage dependent murine streptococcal cell wall (SCW) arthritis model have also been investigated. It was demonstrated that endogenous IL-10 plays a role in the regulation of SCW arthritis. Addition of exogenous IL-10 further enlarged the suppressive effect of endogenous IL-10. An even more pronounced effect was found with the combination of IL-4 and IL-10. The combination resulted in a reduced swelling and an increase in chondrocyte proteoglycan synthesis. Treatment with the combination of IL-4 and IL-10 substantially diminished levels of TNF-α, as occurs for IL-10 treatment alone, but also resulted in strongly reduced IL-1β levels in the synovium, an added effect of potential clinical benefit. Overall, the data is consistent with a role for both IL-4 and IL-10 as chondroprotective agents delivered systemically or locally to joints to prevent cartilage destruction, and indicates a combination containing IL-4 and IL-10 may provide a greater potential therapeutic value than either agent alone.

Severe combined immunodeficient (SCID) mice were used as a model to assess the effect of IL-4 or IL-10 injection on cartilage degradation and mononuclear cell (MNC) recruitment to human rheumatoid synovium in vivo. Human rheumatoid synovium and cartilage from five rheumatoid arthritis patients were injected with recombinant human IL-4 (rhIL-4, 100 ng; rhL-10, 100 ng), a combination of IL-4 and 1–10, or TNF-alpha (1000 U), or phosphate-buffered saline twice a week for 4 weeks. It was found that a combination of human IL-4 and IL-10 inhibited cartilage degradation and invasion by human synovial tissue, establishing the chondroprotective properties of these interleukin agonists.

Human IL-13 has been cloned and sequenced and has been found to share many of the properties of IL-4. IL-13 is about 25% homologous to IL-4. Like IL-4, IL-13 decreases the production of pro-inflammatory cytokines, including IL-1 and TNF-α, by synovial fluid mononuclear cells. IL-13 exhibits anti-inflammatory effects in vivo and thus has therapeutic potential in the treatment of cartilage destruction in the joint.

Compounds useful as IL-4, IL-10 and IL-13 agonists include naturally occurring human IL-4, IL-10 and IL-13, human recombinant IL-4 (rhIL-4), rhIL-10, and rhIL-13 as well as partial sequences thereof, or peptide sequences which have been constructed using recombinant DNA techniques to recognize the IL-4, IL-10 and IL-13 receptors and are capable of activating these receptors on a cell surface. This specifically includes multispecific molecules comprised of an anti-Fc receptor portion and an anti-IL-4, anti-IL-10, and anti-IL-13 receptor portion, wherein at least one portion is constructed using recombinant DNA techniques. Within the context of defining interleukin agonists as pharmacological agonists, the term interleukin agonist includes, but is not limited to: (1) peptide sequences which correspond to naturally (endogenous) produced amino acid sequences or fragments thereof, (2) recombinant interleukins which are truncated or partial sequences of the full length naturally occurring interleukin amino acid sequences which retain the ability to bind cognate receptor and retain biological activity and analogs thereof, and (3) chimeric interleukins which are recombinant polypeptides comprised of truncated or partial sequences corresponding to a portion of the of the full length amino acid sequences attached through oligomers (e.g., amino acids) to a sequence corresponding to a portion of an IgG polypeptide (e.g., IgG hinge and Fc domain) which retain the ability to bind the cognate receptor and retain biological activity.

Examples of interleukin agonists suitable for the present invention are listed below. For all modes of local delivery (i.e., injection, infusion and irrigation) the optimal dose and/or concentration of each suitable agent is that which is therapeutically effective. As an example, for each of the listed agents, the preferred and most preferred concentrations of an irrigation solution containing the listed agent are provided, such concentrations expected to be therapeutically effective. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 3

Therapeutic and Preferred Concentrations Interleukin Agonists

| Compounds | Local Delivery Therapeutic Concentrations (nanomolar) | Preferred Local Delivery Concentrations (nanomolar) |
| --- | --- | --- |
| rhuman IL-4 | 0.5–5,000 | 5–500 |
| rhuman IL-10 | 0.5–5,000 | 5–500 |
| rhuman IL-13 | 0.5–5,000 | 5–500 |

4. Transforming Growth Factor-β Superfamily Agonists

Transforming growth factor-β (TGF-β) subfamily members are 25 kD pleiotropic, multifunctional proteins capable of influencing a variety of cellular functions and are known to be involved in tissue repair and remodeling. In many cases, it enhances the cell interaction with the extracellular matrix (ECM) and increases accumulation of ECM by stimulating production and secretion of ECM proteins and protease inhibitors. TGF-β also has been shown to have synergistic interactions with other cytokines, generally showing anti-inflammatory activities. Multiple isoforms of TGF-β have been identified which share close amino acid sequence homologies. TGF-β1, TGF-β2, and TGF-β3 have been found in human tissue and are active in mammalian cells, although differing in binding affinity.

Members of the TGF-β subfamily are potent modulators of chondrocyte proliferation, differentiation and extracellular matrix accumulation. In cartilage organ cultures, TGF-β1 regulates metabolism of proteoglycans and stimulates collagen and glycosaminoglycan synthesis by rabbit articular chondrocytes. In addition, TGF-β1 increases TIMP expression in human articular chondrocytes and down-regulates expression of IL-1 receptors in articular cartilage.

Bone morphogenetic proteins (BMPs) are multifunctional regulators of cell growth, differentiation and apoptosis that belong to the transforming growth factor (TGF)-β superfamily. More than a dozen members of the BMP protein family have been identified in mammals, which can be subclassified into several groups depending on their structures. BMP-2 and BMP-4 are highly similar to each other. BMP-5, BMP-6, osteogenic protein (OP)-1 (also called BMP-7), and OP-2/BMP-8 are structurally similar to each other. Growth-differentiation factor (GDF)-5 (also termed cartilage-derived morphogenetic protein-1), GDF-6 (also cartilage-derived morphogenetic protein-2), and GDF-7 form another related group. In contrast to BMP-2, BMP-4, BMP-6, and OP-1/BMP-7, which induce bone and cartilage formation in vivo, GDF-5, GDF-6, and GDF-7 more efficiently induce cartilage and tendon-like structures in vivo (Wolfman et al., 1997).

Members of the TGF-β superfamily exert their effects via binding to two types of serine/threonine kinase receptors, both of which are essential for signal transduction (Massague, 1998). The Type II receptors are constitutively active kinases, which transphosphorylate Type I receptors upon ligand binding. The Type I receptors activate intracellular substrates such as Smad proteins and it is through this mechanism that specificity of intracellular signal transduction occurs. Seven different Type I receptors have been isolated in mammals, which were originally termed activin receptor-like kinase (ALK)-1-ALK7. BMP Type IA receptor (BMPR-IA or ALK-3) and BMP Type IB receptor (BMPR-IB or ALK-6) are structurally similar to each other and specifically bind BMPs together with Type II receptors. ALK-2 has been shown to bind activin, but recent data revealed that it is a Type I receptor for certain BMPs (e.g., OP-1/BMP-7) (Macias-Silva et al., 1998). ALK-1 is structurally highly similar to ALK-2, but its physiological ligand is still unknown. ALK-5 and ALK-4 are Type I receptors for TGF-β (TβR-I) and activin (ActR-IB), respectively. ALK-7 is structurally similar to ALK-4 and ALK-5, but its ligand has not been determined yet.

Naturally occurring TGF-β and BMP agonists as well as synthetic or human recombinant (rh) agonists suitable for use in the cartilage-protective solution of the present invention may interact with any of the BMP receptors described above. As used herein, the term "TGF-β and BMP agonists" includes fragments, deletions, additions, amino acid substitutions, mutations, and modifications thereof that retain the biological characteristics of the naturally occurring human TGF-β and BMP agonist ligands. The TGF-β or BMP agonists may be used alone or in synergistic combination with other members of the TGF-β superfamily as anabolic cartilage agents (chondrogenic or promoting cartilage matrix repair) or in combination with inhibitory agents that block cartilage catabolism.

Type I receptors function as downstream components of Type II receptors. The specificity of the intracellular signals by Type I receptors is determined by a specific region in the serine/threonine kinase domain, termed the L45 loop. Thus, the structures of the LA5 loop of BMPR-IA/ALK-3 and BMPR-IB/ALK-6 (BMPR-I group) are identical to each other, and they may transduce similar signals in cells. Similarly, the L45 loops of TβR-I/ALK-5, ActR-IB/ALK-4, and ALK-7 (TβR-I groups) are identical to each other, and they activate similar substrates (Chen et al., 1998). The L45 loops of ALK-1 and ALK-2 (ALK-1 group) are most divergent from the other Type I receptors, but they activate substrates similar to that of the Type I receptors of the BMPR-I group (Armes et al., 1999).

Various proteins may transduce signals from the TGF-β and BMP serine/threonine kinase receptors. Among them, the best-studied molecules are proteins of the Smad family. Eight different Smad proteins have been identified in mammals, and these proteins are classified into three subgroups, (i.e., receptor-regulated Smads (R-Smads), common partner Smads (Co-Smads), and inhibitory Smads). R-Smads are directly activated by Type I receptors, from complexes with Co-Smads, and translocate into the nucleus. The Smad heteromers bind to DNA directly and indirectly via other DNA-binding proteins and thus regulate the transcription of target genes. Smad1, Smad5, and Smad8 are activated by BMPs, whereas Smad2 and Smad3 are activated by TGF-β. For example, Smad2, in combination with Smad4 that functions as a Co-Smad, is translocated to the nucleus where it activates the transcription of genes that mediate the biological effects of TGF. Smad6 and Smad7 are structurally distantly related to the other Smads and act as inhibitory Smads. It has been shown that BMPs induce new cartilage and bone formation in vitro and in vivo and regulate chondrocyte growth and differentiation. Furthermore, these proteins are also implicated in the cartilage repair process. Various studies have shown that BMPs also promote and maintain the chondrogenic phenotype, which is indicated by their ability to stimulate proteoglycan synthesis in chick limb bud cells culture and fetal rat chondroblasts, as well as in rabbit and bovine articular chondrocytes. The importance of BMPs for cartilage and bone formation has been proven by transgenic approach in which specific BMP gene knockouts were studied.

One member of the BMP family, osteogenic protein (OP-1 or BMP-7), appears particularly important for cartilage homeostasis under normal and pathological conditions, such as during repair of cartilage. OP-1 appears to be the only member of the BMP family, along with cartilage-derived morphogenetic proteins, which is expressed by adult articular chondrocytes (Chubinskaya, S., *J. Histochemistry and Cytochemistry* 48:239–50 (2000)). OP-1 was originally purified from bone matrix and shown to induce cartilage and bone formation. The human OP-1 gene has been cloned and biologically active recombinant OP-1 homodimers have been produced. Human recombinant OP-1 can stimulate synthesis of aggrecan and collagen Type II by human articular chondrocytes in vitro. It can also counteract the deleterious effects of IL-1 on the metabolism of these chondrocytes and block bovine cartilage damage mediated by fibronectin fragments. This effect was demonstrated by studying the effects of recombinant human OP-1 on the production of proteoglycan, prostaglandin E2, and IL-1 receptor antagonist by human articular chondrocytes cultured in the presence of interleukin-1beta. Treatment of human articular chondrocytes with OP-1 was effective in overcoming the down-regulation of proteoglycan synthesis induced by low doses of IL-1β. Furthermore, a study found that OP-1 stimulates the synthesis of hyaluronan and CD44, other molecules required for matrix assembly by human chondrocytes. These studies of the expression and regulation to OP-1 in human adult cartilage suggest a role for OP-1 in cartilage protection and repair and indicate that OP-1 can be used as a therapeutic agent that promotes cartilage anabolism and repair of human articular cartilage.

OP-1 (BMP-7) induces cartilage and bone formation when implanted at intra- and extraskeletal sites in vivo. The influence of OP-1 on healing of full-thickness articular cartilage defects was investigated by drilling two adjacent holes through articular cartilage of rabbit knee joint. OP-1 induced articular cartilage healing and regeneration of the joint surface that contained cells resembling mature joint chondrocytes.

These data suggest that one preferred embodiment of the solution useful for the practice of the present invention for the prevention of cartilage degradation and maintaining biological homeostasis of articular cartilage in humans after surgical trauma could include systemic or local application of a member of the TGF-β superfamily, preferably either TGFβ2, BMP-7 (OP-1) or BMP-2, or an equivalent agonist which acts through the same receptors employed by these ligands. The systemic or local delivery may occur in combination with a drug or drugs that are inhibitors of cartilage catabolic processes (e.g. such as MAP kinase inhibitors, MMP inhibitors or nitric oxide synthase inhibitors) and/or other agents for the inhibition of pain and inflammation.

Within the context of defining TGF-β and BMP agonists as pharmacological agonists, the term TGF-β and BMP agonist includes, but is not limited to: (1) peptide sequences which correspond to naturally (endogenous) produced amino acid sequences or fragments thereof, (2) recombinant TGF-βs and BMPs which are truncated or partial sequences of the full length naturally occurring TGF-β and BMP amino acid sequences which retain the ability to bind cognate their respective receptor and retain biological activity and analogs thereof, and (3) chimeric TGF-βs and BMPs which are recombinant polypeptides comprised of truncated or partial sequences corresponding to a portion of the of the full length amino acid sequences attached through oligomers (e.g., amino acids) to a sequence corresponding to a portion of an IgG polypeptide (e.g., IgG hinge and Fc domain) which retain the ability to bind the cognate receptor and retain biological activity.

Examples of TGF-β and BMP agonists suitable for the present invention are listed below. For all modes of local delivery (i.e., injection, infusion and irrigation) the optimal dose and/or concentration of each suitable agent is that which is therapeutically effective. As an example, for each of the listed agents, the preferred and most preferred concentrations of an irrigation solution containing the listed agent are provided, such concentrations expected to be therapeutically effective. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

A range of therapeutic concentrations for local delivery or local action in the surgical solution to the joint may be estimated from values of the dissociation constants (Kd) of each ligand for its cognate receptor. While these values will vary for particular cell types and tissues, the following example is given for BMP-4. Binding experiments with $^{125}$I-BMP-4, revealed the presence of specific, high-affinity binding sites with an apparent dissociation constant of 110 pM and about 6000 receptors per cell. Therefore, at 11 nM BMP-4, binding of the ligand will be maximal and the available receptors will be fully occupied (saturated). The presence of functional receptors for BMP-4 on primary articular chondrocytes has been demonstrated.

TABLE 4

Therapeutic and Preferred Concentrations
TGF-β and BMP-Receptor Agonists

| Compound | Local Delivery Therapeutic Concentrations (nanomolar) | Most Preferred Local Delivery Concentrations (nanomolar) |
| --- | --- | --- |
| TGF-β1 | 0.05–500 | 0.5–100 |
| TGF-β2 | 0.05–500 | 0.5–100 |
| BMP-2 | 0.1–2000 | 1–200 |
| BMP-4 | 0.1–2000 | 1–200 |
| BMP-7 (OP-1) | 0.1–2000 | 1–200 |

5. Cyclooxygenase-2 (Cox-2) Inhibitors

Nonsteroidal anti-inflammatory drugs (NSAIDs) are widely used as anti-inflammatory agents, but have not been specifically developed or therapeutically employed as chondroprotective agents. The direct molecular target for an NSAID drug is the first enzyme in the prostaglandin synthetic pathway, referred to either as prostaglandin endoperoxide synthase or fatty acid cyclooxygenase. Two related forms of cyclooxygenase, termed cyclooxygenase-1 or Type 1 (COX-1) and cyclooxygenase-2 (COX-2) have been characterized. These isozymes are also known as Prostaglandin G/H Synthase (PGHS)-1 and PGHS-2. Both enzymes catalyze the rate-limiting step in the formation of prostanoids that is the conversion of arachidonic acid to prostaglandin H2. COX-1 is present in platelets and endothelial cells and exhibits constitutive activity. In contrast, COX-2 has been identified in endothelial cells, macrophages, fibroblasts and other cells in the joint and its expression is induced by pro-inflammatory cytokines, such as IL-1 and TNF-α.

Within the inflamed joint, COX-2 expression is upregulated and it has been shown that large increases in activity of COX-2 occur concomitant with its upregulation, leading to increased synthesis of prostaglandins which are present in the synovial fluid of patients suffering from inflammatory arthropathies. Cellular sources of prostaglandins (PGs) in the joint include activated chondrocytes, Type A and B synoviocytes and infiltrating macrophages. Cellular functions important in cartilage metabolism modulated by PGs include gene expression, extracellular matrix synthesis and proliferation. Because COX-2 is expressed in inflamed joint tissue or after exposure to mediators of inflammation (e.g., as a result of injury or surgical trauma), the use of a COX-2 inhibitor is expected to provide both anti-inflammatory and cartilage protective activity.

Cartilage destruction in inflammatory arthropathies can be triggered as a consequence of joint injury and as a result of arthroscopic surgical procedures. Chondrocytes are the only cell type in articular cartilage and are known to participate in the breakdown of their own matrix through release of endogenous inflammatory mediators, including PGs. Studies have shown that COX-2 gene expression, protein synthesis, and PG release in normal human articular chondrocytes is rapidly induced by cytokines, including IL-1, TNF-α and IL-6. Levels of mRNA are detected as early as 2 hours after cytokine induction, reach high levels at 6 hours and show a remarkably long duration of expression for at least 72 hours. Similarly, cell culture studies of IL-1α and TNF-α activation of human synoviocytes have shown large increases in expression of COX-2 and production of prostaglandin E2 (PGE2). Treatment with a variety of NSAIDS, such as ketoprofen, abolishes the induced PGE2 response. In a chondrocyte cell culture system, the specific COX-2 inhibitor compound NS-398 prevented the increase in PGE2 production induced by the cytokines while COX-1 levels remained stable (Morisset, S., 1998, J. Rheumatol. 25:1146–53). Thus, it can be deduced that blocking PG production by activated chondrocytes, which is associated with expression of COX-2, can provide a chondroprotective effect.

NSAIDs are commonly used in the treatment of patients with osteoarthritis or rheumatoid arthritis, but their effects on articular cartilage metabolism in the context of these arthritic diseases remains a subject of debate. For instance, the clinical treatment of osteoarthritis and rheumatoid arthritis with NSAIDs is successful in reducing inflammation. However, it is thought that some NSAIDs which are not selective for COX-2, primarily salicylates and indomethacin, accelerate osteoarthritic cartilage destruction by impairing proteoglycan synthesis by chondrocytes, whereas other NSAIDS are thought to have a somewhat chondroprotective effect by stimulating cartilage repair. Most studies have shown that NSAIDs have little or no effect on cartilage. Due to the current lack of use of this class of drugs in the treatment of synovitis and cartilage destruction following traumatic joint injury and surgical trauma, the unique properties of each NSAID on the pathophysiological mechanisms that contribute to cartilage destruction will need to be established.

Since the two COX isozymes are pharmacologically distinct, isozyme-specific (selective) cyclooxygenase inhibitors that are useful for anti-inflammatory therapy have been developed and some of these same COX-2 inhibitors have been tested in models of joint inflammation. However, the effects in vitro of the COX-2 inhibitors on the synthesis and degradation of cartilage proteoglycans, as well as synovial production of IL-1, IL-6, IL-8, and prostanoids, indicate that certain NSAIDs may vary considerably in their effects in vivo on cartilage and synovial production of interleukins and eicosonoids, such that the integrated effects of these parameters may influence the outcome of COX-2 inhibitors on cartilage integrity. For example, some NSAIDS can accelerate joint damage in osteoarthritis by enhancing the production of pro-inflammatory cytokines or inhibiting cartilage proteoglycan synthesis. However, despite the possible variance in clinical effect among COX-2 specific inhibitors, inhibition of COX-2 typically results in a reduction of synovitis and an expected decrease in the risk of cartilage damage.

A variety of biochemical and cellular and animal assays have been developed to assess the relative selectivity of inhibitors for the COX-1 and COX-2 isoforms. In general, a criteria for defining selectivity is the ratio of the COX-1/COX-2 inhibitory constants (or COX-2/COX-1) obtained for a given biochemical or cellular assay system. The selectivity ratio accounts for different absolute $IC_{50}$ values for inhibition of enzymatic activity that are obtained between microsomal and cellular assay systems (e.g., platelet and macrophage cell lines stably expressing recombinant human COX isozymes). Furthermore, inhibition of COX-2 mimics the inhibitory effects triggered by chondroprotective (inhibitory) cytokines, such as IL-4, which down-regulate intracellular COX-2 synthesis. Comparison of the selectivity of more than 45 NSAIDs and selective COX-2 inhibitors (*Can. J. Physiol. Pharmacol.* 75:1088–95 (1997)) showed the following rank-ordered relative selectivity for COX-2 vs. COX-1: DuP 697>SC-58451=celecoxib>nimesulide= meloxicam=piroxicam=NS-398=RS-57067>SC-57666> SC-58125>flosulide>etodolac>L-745,337>DFU-T-614, with $IC_{50}$ values ranging from 7 nM to 17 μM.

From the molecular and cellular mechanism of action defined for selective COX-2 inhibitors, such as celecoxib and rotecoxib, as well as from animal studies, these compounds are expected to exhibit chondroprotective action when applied perioperatively in an irrigation solution or in an injection directly to a joint. In particular, COX-2 inhibitors are expected to be effective drugs delivered in an irrigation solution during an arthroscopic surgical procedure or by direct injection into a joint prior to, during or after a surgical procedure or other injury to the joint.

Examples of COX-2 inhibitors suitable for the present invention are listed below. For all modes of local delivery (i.e., injection, infusion and irrigation) the optimal dose and/or concentration of each suitable agent is that which is therapeutically effective. As an example, for each of the listed agents, the preferred and most preferred concentrations of an irrigation solution containing the listed agent are provided, such concentrations expected to be therapeutically effective. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 5

Therapeutic and Preferred Concentrations of Cyclooxygenase-2 Inhibitors

| Compounds | Local Delivery Therapeutic Preferred Concentrations (nM) | Most Preferred Local Delivery Concentrations (nM) |
| --- | --- | --- |
| rofecoxib (MK 966) | 0.3–30,000 | 30–3,000 |
| SC-58451 | 0.3–30,000 | 30–3,000 |
| celecoxib (SC-58125) | 0.3–30,000 | 30–3,000 |
| meloxicam | 0.5–50,000 | 50–5,000 |
| nimesulide | 0.5–50,000 | 50–5,000 |
| diclofenac | 0.3–30,000 | 30–3,000 |
| NS-398 | 0.3–30,000 | 30–3,000 |
| L-745,337 | 0.2–100,000 | 20–10,000 |
| RS57067 | 0.2–100,000 | 20–10,000 |
| SC-57666 | 0.2–100,000 | 20–10,000 |
| flosulide | 0.2–100,000 | 20–10,000 |

6. MAP Kinase Inhibitors

The mitogen-activated protein (MAP) kinases are a group of protein serine/threonine kinases that are activated in response to a variety of extracellular stimuli and function in transducing signals from the cell surface to the nucleus. The MAP kinase cascade is one of the major intracellular signaling pathways that transmit signals from growth factors, hormones and inflammatory cytokines to intermediate early genes. In combination with other signaling pathways, these activated mitogen-activated protein-kinases (MAPKs) differentially alter the phosphorylation state and activity of transcription factors, and ultimately regulate cell proliferation, differentiation and cellular response to environmental stress. For example, a member of the MAPK family (p38) mediates the major biochemical signal transduction pathways from the potent pro-inflammatory cytokines, IL-1 and TNF-α, leading to induction of cyclooxygenase-2 (COX-2) in stimulated macrophages, through cis-acting factors involved in the transcriptional regulation of the COX-2 gene.

The members of the MAP kinase class of agents are composed of at least three families that are known to differ in sequence, size of the activation loop, activation by extracellular stimuli and participation in distinct signal transduction pathways. Prominent members among this family of MAP kinases include the extracellular signal-regulated kinases (ERKs), ERK1 and ERK2 (p44MAPK and p42MAPK, respectively); stress-activated protein kinase 1 (SAPK1) family which is also referred to as the JNK or jun N-terminal kinase family; and the p38 MAP kinase family which is also known as stress-activated kinase 2/3 (SAPK-2/3). The p38 kinases are activated by stresses, most notably pro-inflammatory cytokines. Within the p38 family, there are at least four distinct homologs (isotypes or isoenzymes) which standard nomenclature refers to either as SAPK2a, SAPK2b, SAPK2d, SAPK3, or p38α, β, δ (SAPK4) and γ, respectively. The inhibitors of MAP kinases useful for the practice of this invention may interact with any one or combination of the above MAP kinases. For specific MAP kinase inhibitors, the inhibitory constants characterized through assays of purified in vitro enzymes and in cellular assays may vary over a wide range of concentrations and demonstrate utility in this application. Activation of p38 MAP kinase is mediated by dual phosphorylation of threonine and tyrosine residues. Both TNF-α and IL-1 treatment of cells has been shown to rapidly (within 5 min) increase phosphorylation and activate p38 MAP kinase.

Previous work has shown that small-molecule inhibitors can specifically inhibit p38 MAP kinase (Lee, J. et al., *Nature* 372:739–746 (1994)) and produce anti-inflammatory effects at the biochemical level and in various animal models. Cuenda and coworkers (Cuenda, A. et al., *FEBS Lett.* 364:229 (1995)) showed that the compound, SB203580 [4-(4-fluorophenyl)-2-(4-methylsulfinylphenyl)-5-(4-pyridyl)imidazole] inhibited p38 in vitro ($IC_{50}$=0.6 μM), suppressed the activation of MAPK activating protein kinase-2 and prevented the phosphorylation of heat shock protein (hsp) 27 in response to IL-1 and cellular stresses in vivo. The kinase selectivity of SB203580 inhibitory action for p38 was demonstrated by its failure or at best weak inhibition of at least 15 other protein kinases in vitro, including members of the PKC, PKA, src and receptor tyrosine kinase families (Lee, J., *Pharmacol. Ther.* 82:389–397 (1999)). In cellular studies, pre-incubation with SB 203580 has been shown to block the IL-1 and TNF-α induced phosphorylation of the enyzme and subsequent IL-8 production. This supports the preemptive effect of delivering the inhibitors during the surgical procedure.

The role of p38 mitogen-activated protein kinase (MAPK) in biochemical inflammatory responses resulting in destruction of cartilage has been studied using SB203580, which specifically inhibits the enzyme. Actions of IL-1 that are selectively controlled by p38 MAPK are the regulation of prostaglandin H synthase-2 (COX-2), metalloproteinases, and IL-6 (Ridley, S. et al., *J. Immunol.* 158:3165–73 (1997)). In human fibroblasts and vascular endothelial cells, SB203580 inhibited ($IC_{50}$=0.5 µM) IL-1-induced phosphorylation of hsp 27 (an indicator of p38 MAPK activity) in fibroblasts without affecting the other known IL-1-activated protein kinase pathways (p42/p44 MAPK, p54 MAPK/c-Jun N-terminal kinase). In addition, SB203580 significantly inhibited IL-1-stimulated IL-6 (30 to 50% at 1 µM) but not IL-8 production from human fibroblasts and endothelial cells.

Importantly, SB203580 strongly inhibited IL-1-stimulated prostaglandin production by fibroblasts and human endothelial cells. This was associated with the inhibition of the induction of COX-2 protein and mRNA. $PGE_2$ contributes to increased expression of matrix metalloproteinases that are important mediators of cartilage degradation. Both synovial fibroblasts and chondrocytes express the COX-2 gene at high levels upon activation by cytokines and extracelluar stimuli. The MAPK inhibitor provides chondroprotective activity due to its inhibitory activity on MAP kinases expressed in these and other cell types.

MAPK inhibitors are expected to be effective as cartilage protective agents when applied systemically or locally to tissues of the joint in a variety of inflammatory or pathophysiological conditions. SB 203580 has been characterized in several pharmacological models in vivo and demonstrated to have activity under long term, oral dosing. SB203580 was found to inhibit the stimulation of collagenase-1 and stromelysin-1 production by IL-1 without affecting synthesis of TIMP-1. Furthermore, SB203580 prevented an increase in IL-1-stimulated collagenase-1 and stromelysin-1 mRNA. In a model of cartilage breakdown, short-term IL-1-stimulated proteoglycan resorption and inhibition of proteoglycan synthesis were unaffected by SB 203580, while longer term collagen breakdown was prevented. In addition, SB203580 was found to be effective in inhibiting IL-1-induced nitric oxide production in bovine articular cartilage explants and chondrocytes (Badger, 1998). These in vitro observations provide a basis for cartilage protective activity of the MAP kinase inhibitor administered systemically or directly and locally to these tissues in the joint.

p38 MAP kinase is involved in TNF-induced cytokine expression, and drugs which function as inhibitors of p38 MAP kinase activity block the production of pro-inflammatory cytokines (Beyaert, R. et al., *EMBO J.* 15:1914–23 (1996)). TNF-α treatment of cells activated the p38 MAPK pathway as shown by increased phosphorylation of p38 MAPK itself and activation of its substrate proteins. Pretreatment of cells with SB203580 completely blocked TNF-α induced activation of MAPK activating protein kinase-2 and hsp27 phosphorylation. Under the same conditions, SB203580 also completely inhibited TNF-α induced synthesis of IL-6 and expression of a reporter gene that was driven by a minimal promoter containing two NF-6B elements. Thus, these studies and related studies on other p38 inhibitors show that the action of inhibitors, such as SB203580 and FR133605, on p38 MAPK interfere selectively with TNF-α- and IL-1-induced activation of various proteins linked to the cartilage degradation. Thus, the selective inhibition of the MAP kinase signaling pathways of these key pro-inflammatory cytokines by inhibition of a kinase downstream of the receptor indicate that MAP kinase inhibitors may provide a chondroprotective effect.

SB 203580 has been evaluated in several animal models of cytokine inhibition and inflammatory disease. It was demonstrated to be a potent inhibitor of inflammatory cytokine production in vivo in both mice and rats with $IC_{50}$ values of 15 to 25 mg/kg. SB 203580 possessed therapeutic activity in collagen-induced arthritis in DBA/LACJ mice with a dose of 50 mg/kg resulting in significant inhibition of paw inflammation. Antiarthritic activity was also observed in adjuvant-induced arthritis in the Lewis rat when SB203580 was administered p.o. at 30 and 60 mg/kg/day. Additional evidence was obtained for beneficial effects on bone resorption with an $IC_{50}$ of 0.6 µM.

In summary, a variety of biochemical, cellular and animal studies show that p38 MAPK plays an important role in the regulation of responses to IL-1 and TNF-α and that it is involved in the regulation of mRNA levels of some inflammatory-responsive genes, such as COX-2. Inhibitors of p38 block the production of pro-inflammatory cytokines and inhibit the production of MMPs, and have been demonstrated to inhibit collagen breakdown in cartilage explants.

The use of MAPK inhibitor to block the actions of key pro-inflammatory cytokines, such as IL-1 and TNF-α, will have beneficial effects on many cell types in the joint, including synovial fibroblasts, macrophages and chondrocytes, thus inhibiting subsequent pathological effects such as infiltration of inflammatory cells into the joint, synovial hyperplasia, synovial cell activation, and cartilage breakdown. Thus, a MAPK inhibitor should block the propagation of the inflammatory response by the aforementioned cytokines, and thereby interrupt the disease process.

Examples of MAPK inhibitors suitable for the present invention are listed below. For all modes of local delivery (i.e., injection, infusion and irrigation) the optimal dose and/or concentration of each suitable agent is that which is therapeutically effective. As an example, for each of the listed agents, the preferred and most preferred concentrations of an irrigation solution containing the listed agent are provided, such concentrations expected to be therapeutically effective for local delivery. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 6

Therapeutic and Preferred Concentrations of MAP Kinase Inhibitors

| Compounds | Local Delivery Therapeutic Concentrations (nanomolar) | Local Delivery Preferred Concentrations (nanomolar) |
| --- | --- | --- |
| SB 203580 | 0.5–50,000 | 50–5,000 |
| SB 203580 iodo | 0.5–50,000 | 50–5,000 |
| SB 202190 | 0.2–20,000 | 20–2,000 |
| SB 242235 | 0.2–10,000 | 20–1,000 |
| SB 220025 | 0.2–10,000 | 20–1,000 |
| RWJ 67657 | 0.3–30,000 | 30–3,000 |
| RWJ 68354 | 0.9–90,000 | 90–9,000 |
| FR133605 | 1–100,000 | 10–10,000 |
| L-167307 | 0.5–50,000 | 50–5,000 |
| PD 98059 | 0.1–10,000 | 10–1000 |
| PD 169316 | 1–100,000 | 10–10,000 |

7. Inhibitors Of Matrix Metalloproteinases

Destruction of articular cartilage is a common feature in joint diseases such as osteoarthritis and rheumatoid arthritis, but also occurs following injury to the joint. Pathophysiologically, a structural breakdown of proteoglycans and collagen is observed, which impairs the biomechanical properties of cartilage. The maintenance of a normal, healthy extracellular matrix reflects a balance between the rate of biosynthesis and incorporation of matrix components, and the rate of their degradation and subsequent loss from the cartilage into the synovial fluid. A variety of proteases have the potential to cleave cartilage and are involved in the degradation process, most notably the matrix metalloproteinases.

Matrix metalloproteinases (MMPs), or matrixins, are a family of at least 15 zinc endopeptidases that function extracellularly and play a key role in pathological degradation of tissue. Current nomenclature and alternative names for members of the MMP are provided in Table 7. Most MMPs are highly regulated and most are not constitutively expressed in normal tissues. However, pro-inflammatory cytokines, such as IL-1 and TNF-$\alpha$, initiate transcription and expression. An imbalance created by upregulation and activation of tissue-degrading MMPs is a primary causative factor in the cartilage breakdown process during chronic inflammatory diseases and sustained synovial inflammatory responses subsequent to joint injury. Cartilage matrix metabolism has been studied in patients with either a meniscal injury or anterior cruciate ligament rupture in the knee. It was shown that concentrations of stromelysin-1 (MMP-3), collagenase, tissue inhibitor of metalloproteinases (TIMP-1), and proteoglycan fragments increased in human knee synovial fluid after traumatic knee injury. Temporally, these values increased immediately over reference levels and remained significantly elevated (10-fold increase) over a period of one year. These changes likely drive the increase in the concentration of proteoglycan fragments that are observed in synovial fluid after knee ligament injury.

TABLE 7

Matrix Metalloproteinases

| MMP | Alternative Names | EC Number | Substrates |
|---|---|---|---|
| MMP-1 | Collagenase Fibroblast Collagenase Interstitial Collagenase | EC3.4.24.7 | Collagens (I, II, II, VII, and X); Gelatin; aggrecan; hyaluronidase-treated versican; proteoglycan link protein; large tenascin-C; $\alpha_1$-antitrypsin/$\alpha_1$-proteinase inhibitor ($\alpha_1$-AT); $\alpha_1$ anti-chymotrypsin ($\alpha_1$-ACHYM); $\alpha_2$ M; rat $\alpha_1$ M; pregnancy zone protein; rat $\alpha_1 I_3$ ($\alpha_1$-inhibitor 3); ovostatin; entactin; MBP; GST-TNF/TNF peptide; L-selection; IL-1$\beta$; serum amyloid A; IGF-BP5; IGF-BP3; MMP-2; MMP-13 |
| MMP-2 | 72-kDa Gelatinase Gelatinase A Type IV Collagenase Neutrophil Gelatinase | EC3.4.24.24 | Collagens (I, IV, V, VI, X, XI, and XIV); Gelatin; elastin; fibronectin; laminin-1, laminin-5; gelactin-3; aggrecan; decorin; hyaluronidase-treated versican; proteoglycan link protein; osteonectin; MBP; GST-TNF/TNF peptide; IL-1$\beta$; A$\beta_{1-40}$; A$\beta_{10-20}$; APP$_{695}$; $\alpha_1$-AT; prolysyl, oxidase fusion protein; IGF-BP5; IGF-BP3; FGF R1; MMP-1; MMP-9; MMP-13 |
| MMP-3 | Stromelysin-1 Transin | EC3.4.24.17 | Collagens (III, IV, V, IX); Gelatin; aggrecan; versican and hyaluronidase-treated veriscan; perlecan; decorin; proteoglycan link protein; large tenascin-C; fibronectin; laminin; entactin; osteonection; elastin; casein; $\alpha_1$-ACHYM; antithrombin-III; $\alpha_2$ M; ovostain; Substance P; MBP; GST-TNF/TNF peptide; IL-$\beta$3; serum amyloid A; IGF-BP3; fibrinogen and cross-linked fibrin; plasminogen; MMP-1 "superactivation", MMP-2/TIMP-2 complex; MMP-7; MMP-8; MMP-9; MMP-13 |
| MMP-7 | Matrilysin PUMP | EC3.4.24.23 | Collagen IV and X; Gelatin; aggrecan; decorin; proteoglycan link protein; fribronectin and laminin; insoluble fibronectin fibrils; enactin; large and small tenascin-C; osteonectin; $\beta$4 integrin; elastin; casein; transferrin; MBP; $\alpha_1$-AT; GST-TNF/TNF peptide; plasminogen; MMP-1; MMP-2; MMP-9; MMP-9/TIMP-1 |
| MMP-8 | Neutrophil Collagenase Collagenase I | EC3.4.24.34 | Collagens (I, II, III, V, VII and X); Gelatin; aggrecan; $\alpha_1$-AT; $\alpha_1$-ACHYM; $\alpha_2$-antiplasmin; fibronectin |
| MMP-9 | 92 kDa Gelatinase Gelatinase B | EC3.4.24.35 | Collagens (IV, V, VII, X and XIV); Gelatin; elastin; galectin-3; aggrecan; hyaluronidase-treated versican; proteoglycan link protein; fibronectin; entactin; osteonectin; $\alpha_1$-AT; MBP; GST-TNF/TNF peptide; IL-1$\beta$; A$\beta_{1-40}$; plasminogen |
| MMP-10 | Stromelysin-2 | EC3.4.24.22 | Collagens (III, IV and V); Gelatin; casein; aggrecan; elastin; proteoglycan link protein; MMP-1; MMP-8 |
| MMP-11 | Stromelysin-3 | EC3.4.24 | Human enzyme: $\alpha_1$-AT; $\alpha_2$ M; casein, laminin, fibronectin, gelatin, collagen IV and carboxy-methylated transferrin |
| MMP-12 | Macrophage Metalloelastase | EC3.4.24 | Collagen IV; Gelatin; elastin and $\kappa$-elastin; casein; $\alpha_1$-AT; fibronectin; vitronectin; laminin; enactin; proteoglycan monomer; |

TABLE 7-continued

Matrix Metalloproteinases

| MMP | Alternative Names | EC Number | Substrates |
|---|---|---|---|
| MMP-13 | Collagenase-3 | EC3.4.24 | GST-TNF; MBP; fibrinogen; fibrin; plasminogen Collagens (I, II and III, IV, IX, X and XIV); Gelatin, α1-ACHYM and plasminogen activator inhibitor 2; aggrecan; perlecan; large tenascin-C, fribronectin; osteonectin; MMP-9 |
| MMP-14 | MT-MMP-1 | EC3.4.24 | Collagen (I, II and III); Gelatin, casean, κ-elastin, fribronectin, laminin, vitronectin and proteoglycans; large tenascin-C, enactin; $\alpha_1$-AT, $\alpha_2$ M; GST-TNF; MMP-2; MMP-13 |
| MMP-15 | MT-MMP-2 | | Fibronectin, large tenascin-C, entactin, laminin, aggrecan, perlecan; GST-TNF; MMP-2 |

The MMP family of enzymes has been shown to be secreted from human chondrocytes and by cells of the synovium, such as synovial fibroblasts. Furthermore, using in situ hybridization, it was shown that human synovium synthesizes both stromelysin-1 and collagenase. Stromelysin-1 (MMP-3) is capable of degrading all of the components of the cartilage matrix. There is evidence that chondrocytes contribute to cartilage degradation by the release of the matrix-degrading enzyme, collagenase-3. Upon activation by pro-inflammatory cytokines, MMPs are secreted from cells in a latent form, are activated extracellularly, and are inhibited by tissue inhibitors of metalloproteinases (TIMPs). The balance between the activities of MMPs and TIMPs is thought to be important for the maintenance of an intact cartilage matrix. Under pathological conditions such as osteoarthritis and rheumatoid arthritis, several studies have shown elevated amounts of MMPs, resulting in an imbalance between MMPs and TIMPs that is considered to account for the observed cartilage destruction.

The MMPs are regulated by cytokines, such as interleukin-1 (IL-1), and growth factors that act on chondrocytes and synoviocytes to enhance their protease production. Other pro-inflammatory cytokines, such as IL-6, IL-8 and TNF-α, also upregulate the production of matrix-degrading enzymes. This leads to cartilage destruction, which is usually assessed as the loss of sulfated glycosaminoglycans (GAGs) and the cleavage of collagen. IL-1, which is present in the joint fluid of patients with arthritic diseases, stimulates chondrocytes to synthesize elevated amounts of enzymes such as stromelysin, fibroblast and neutrophil collagenase, and plasminogen activator. In addition, IL-1 inhibits synthesis of plasminogen activator inhibitor-1 and TIMP, and also inhibits synthesis of matrix constituents such as collagen. The imbalance between the levels of inhibitors and enzymes leads to an increase in the amount of active proteases and, combined with a suppression of matrix biosynthesis, results in cartilage degradation.

Using cartilage slices as an in vitro model, it has been shown that collagenase inhibitors can inhibit either the IL-1 or IL-8 stimulated invasion of articular cartilage by rheumatoid synovial fibroblasts (RSF). The collagenase inhibitors, 1,10-o-phenanthroline and phosphoramidon, substantially inhibited the concentration-dependent penetration of cartilage by RSF cells at concentrations of 10–150 µM. The selective effect of cytokines on the secretion of proteinases demonstrates that synovial fibroblast-like cell-mediated articular degradation is a highly regulated process. Thus, the ability to inhibit protease activity and associated matrix degradation locally within the joint is expected to inhibit the cartilage destruction process. The action of the inhibitors in the limited in vitro system suggests that therapeutic intervention using systemic or local delivery of synthetic MMP inhibitors with appropriate pharmokinetics will be effective as chondroprotective agents.

Examples of MMP inhibitors suitable for the present invention include U-24522 ((R,S)-N-[2-[2-(hydoxylamino)-2-oxoethyl]-4-methyl-1-oxopentyl]-L-leucyl-L-phenylalaniamide); BB2516; ($N^2$-[35[Hydroxy-4-(N-hydroxyamino)-2R-isobutyl]-L-leucine-$N^1$-methylamide, also known as marimastat) peptides such as MMP Inhibitor I and MMP-3 Inhibitor, and larger proteins such as TIMP-1 or fragments thereof, and are listed in the Table below: For all modes of local delivery (i.e., injection, infusion and irrigation) the optimal dose and/or concentration of each suitable agent is that which is therapeutically effective. As an example, for each of the listed agents, the preferred and most preferred concentrations of an irrigation solution containing the listed agent are provided, such concentrations expected to be therapeutically effective when delivered locally. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 8

Therapeutic and Preferred Concentrations of Matrix Metalloproteinases (MMPs) Inhibitors

| Compounds | Local Delivery Therapeutic Concentrations (nanomolar) | Most Preferred Local Delivery Concentrations (nanomolar) |
|---|---|---|
| 1. BB2516 | 0.2–2000 | 2–200 |
| 2. GM1489 | 0.2–400 | 2–100 |
| 3. GM6001 | 0.4–800 | 2–200 |
| 4. U-24522 | 0.2–2,000 | 20–200 |
| minocycline | 30–500,000 | 300–3,000 |
| MMP Inhibitor I 4-Abz-Gly-Pro-D-Leu-D-Ala-NHOH | 0.3–3,000 | 3–600 |
| MMP-3 Inhibitor Ac-Arg-Cys-Gly-Val-Pro-Asp-NH$_2$ | 0.5–5,000 | 5–500 |
| rhuman TIMP1 | 0.5–5,000 | 5–500 |
| rhuman TIMP2 | 0.3–3,000 | 3–600 |

8. Inhibitors of Nuclear Factor Kappa B (NFκB)

Pro-inflammatory and cartilage-destructive cellular pathways are regulated by extracellular and intracellular signaling mechanisms that are targets for novel therapeutic local and systemic drug delivery. The complete molecular signaling mechanisms utilized by the pro-inflammatory cytokine interleukin-1 (IL-1) to activate the transcription factor, nuclear factor kappaB (NFκB), are poorly defined. Nevertheless, a key molecule that is involved in intracellular signaling at the level of gene transcription is the pro-inflammatory transcription factor, (NFκB). NFκB activity is mediated by a family of transcription factor subunits that bind to DNA either in the form of homodimers or heterodimers. These subunits are typically present within the cytoplasm of cells in an inactive form due to the binding of the inhibitory subunit called IκB. Activation of IL-1 receptors, and other extracellular signals, induce degradation of IκB and concomitant dissociation of NFκB from the inhibitors, followed by translocation to the nucleus. NFκB, was found to be involved in IL-1 induced expression and was capable of increasing pro-inflammatory COX-2 protein expression in RA synovial fibroblasts.

The identification of NFκB as a key molecular target is based upon its role as a common downstream signaling element regulating gene expression of several critical inflammatory mediators linked to joint inflammation and cartilage-destructive pathways. The response of many genes (COX-2, collagenase, IL-6, IL-8) are governed by promoters which contain both NFκB promoter elements. Activation of NFκB mediates the induction of many proteins central to the inflammatory process, such as cytokines, cell-adhesion molecules, metalloproteinases and other proteins that participate in the production of prostaglandins and leukotrienes (COX-2) in synoviocytes. Thus, this transcription factor represents a physiologically significant target in therapies directed to the injury responses of human synovial fibroblasts, human articular chondrocytes, as well as other cells in the joint.

Specifically, it has been shown that exposure of human rheumatoid synovial fibroblasts (RSF) to interleukin 1beta (IL-1beta) results in the coordinate up-regulation of 85-kD phospholipase A2 (PLA2) and inducible cyclooxygenase (COX-2). Together, these two enzymes promote the subsequent biosynthesis of $PGE_2$, a primary inflammatory mediator in the joint. Oligonucleotide decoys and antisense were used to demonstrate the participation of the (NFκB), in the regulation of the prostanoid-metabolizing enzymes. Antagonizing NFκB mRNA using anti-sense oligonucleotide resulted in decreased binding to the COX gene promoter.

Hymenialdisine, a marine natural product, has recently been characterized as an inhibitor of NFκB activation and exposure of IL-1-stimulated RSF-inhibited PGE2 production in a concentration-dependent manner ($IC_{50}$=1 µM). The specificity of the molecular target was shown through use of an analog, aldisine, and the protein kinase C inhibitor, RO 32-0432, which were inactive. Direct action of hymenialdisine on IL-1-induced NFκB activation was demonstrated by a significant reduction (approximately 80%) in NFκB binding to the classical κB consensus motif and inhibition of stimulated p65 migration from the cytosol of treated cells. As expected for an inhibitor of NFκB transcriptional regulation, hymenialdisine-treated RSF did not transcribe the mRNAs for either COX-2 or PLA2 in response to IL-1. Consequently, reduced protein levels for these enzymes and reductions in the ability to produce PGE2 were observed. Furthermore, IL-1-stimulated interleukin-8 (IL-8) production, which is known to be an NFκB-regulated event, was also inhibited by hymenialdisine, whereas IL-1-induced production of vascular endothelial growth factor, a non-NFκB-regulated gene, was not affected by exposure to hymenialdisine. Thus, hymenialdisine inhibits IL-1-stimulated synovial fibroblast formation of PGE2 through its inhibitory effect on NFκB activation. This provides a basis to define its use as a novel inhibitor to block the role of NFκB in joint inflammation and cartilage destruction.

Examples of NFκB inhibitors suitable for the present invention are listed below. For all modes of local delivery (i.e., injection, infusion and irrigation), the optimal dose and/or concentration of each suitable agent is that which is therapeutically effective. As an example, for each of the listed agents, the preferred and most preferred concentrations of an irrigation solution containing the listed agent are provided, such concentrations expected to be therapeutically effective when delivered locally. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 9

Therapeutic and Preferred Concentrations of Inhibitors of NFκB

| Compounds | Local Delivery Therapeutic Concentrations (nanomolar) | Most Preferred Local Delivery Concentrations (nanomolar) |
| --- | --- | --- |
| Caffeic acid phenylethyl ester (CAPE) | 1–100,000 | 50–20,000 |
| DM-CAPE | 0.5–50,000 | 50–5,000 |
| SN-50 peptide | 0.1–100,000 | 100–20,000 |
| hymenialdisine | 1–100,000 | 100–10,000 |
| pyrolidone dithiocarbamate | 1–50,000 | 50–10,000 |

9. Nitric Oxide Synthase Inhibitors

Nitric oxide (NO) is a widespread intracellular and intercellular mediator involved in the pathophysiological mechanisms of some connective tissue diseases. NO is formed from L-arginine by a family of enzymes, the NO synthases, which are localized intracellularly. Three isoforms of NO synthase have been cloned and sequenced. Endothelial cell NO synthase (ecNOS) and brain NO synthase (bNOS) are constitutively active. A distinct isoform of NO synthase, inducible NOS (iNOS), is found in many cell types, including chondrocytes. It is absent under basal conditions, but is upregulated in response to pro-inflammatory mediators such as IL-1β and TNF-α. Recent findings show that IL-1 is a very potent stimulator of chondrocyte NO synthesis and that IL-1 acts through its ability to upregulate the level of the iNOS. Within the joint, chondrocytes are the major source of NO and chondrocytic iNOS induced by pro-inflammatory cytokines is considered to mediate many effects of IL-1 in inflammatory arthropathies.

Drugs that specifically inhibit chondrocyte inducible NO synthase (iNOS) may have a therapeutic role in the prevention of chondrodestruction that occurs due to joint injury (e.g., surgical procedures involving the joint). Evidence supporting such a beneficial therapeutic effect is based upon a substantial number of studies which have evaluated a variety of iNOS inhibitors for their ability to inhibit inducible NO synthase activity in cultured chondrocytes and explants of cartilage from patients with osteoarthritis. A class of compounds, termed S-substituted isothioureas, have been characterized as potent inhibitors of NO biosynthesis in cartilage. S-methyl isothiourea and S-(aminoethyl) isothiourea were 2–4 times more potent than $N^G$-monomethyl-L-arginine, 5–10 times more potent than aminoguanidine and over 300 times more potent than $N^\omega$-nitro-L-arginine and $N^{\omega}$-nitro-L-arginine methyl ester. These isothiourea compounds provide a potent and relatively specific class of inhibitors of iNOS in cartilage and thus are suitable for systemic or local delivery in accordance with aspects of the invention (Jang, D., *Eur. J. Pharmacol.* 312:341–347(1996)).

The cartilage protective therapeutic potential of NO synthase inhibitors has also been assessed using in vitro systems such as isolated chondrocytes to define effects on the cartilage matrix. Inhibition of endogenous NO production by $N^G$-monomethyl-L-arginine (L-NMMA), an established NO synthase inhibitor, leads to the suppression of gelatinase, collagenase, and stromelysin production by IL-1β-stimulated chondrocytes. Inhibition of NO production also partially reduces the increase in the lactate production that occurs from the exposure of chondrocytes to IL-1β. Treatment of cartilage fragments with L-NMMA partially reverses the IL-1β inhibitory effect of glycosaminoglycan synthesis, inhibits IL-1β-stimulated MMP activities, and increases IL-1 receptor antagonist (IL-1ra) production. NO can also modulate proteoglycan synthesis indirectly by decreasing the production of TGF-β1 by chondrocytes exposed to IL-ββ. It prevents autocrine-stimulated increases in TGF-β1, thus diminishing the anabolic effects of this cytokine in chondrocytes.

A study has compared the potency of new aminoguanidine, S-methylisothiourea (SMT), S-aminoethylisothiourea (AETU), L-NMMA and N-nitro-L-arginine methyl ester (L-NAME) NOS inhibitors on the inhibitory effect of recombinant human IL-1 responses on proteoglycan synthesis and NO production. Different culture systems have been shown to respond in a concentration dependent manner to IL-1β challenge with a large increase in NO production and a marked suppression of proteoglycan synthesis. The above NOS inhibitors (at 1 to 1000 μM) inhibited NO production by cartilage cells treated with IL-1β and had marked effects on restoring proteoglycan synthesis in chondrocytes. Therefore, if NO production can be blocked using a therapeutically effective concentration and dose, then IL-1β inhibition of proteoglycan synthesis will be prevented.

NO synthase is expressed in cartilage obtained from the joint of patients with arthritic disease. In patients presenting either rheumatoid arthritis or osteoarthritis, increased levels of nitrite have been observed in the synovial fluid and it has been shown that a significant source of NO production in these patients is derived from articular cartilage. Furthermore, it has been found that sustained systemic delivery of L-NIL, a potent inhibitor of iNOS, reduces the progression of experimental OA in dogs (induced by sectioning of the ACL) and causes a substantial decrease in IL-1β, $PGE_2$, NO and MMP production. These findings suggest that NO is a potent regulator of the effects of IL-1β and contributes to the pathophysiology of joint diseases.

Thus, these in vitro and in vivo results indicate that specific inhibitors of NO synthases are potential novel drugs for the clinical treatment of synovial inflammation and can provide chondroprotective effects when delivered systemically or locally in combination with one or more drugs chosen from the anti-inflammatory, cartilage-protective, and anti-pain classes to treat a surgically treated joint or other injured joint.

Examples of NO synthase inhibitors suitable for the present invention are listed below. For all modes of local delivery (i.e., injection, infusion and irrigation), the optimal dose and/or concentration of each suitable agent is that which is therapeutically effective. As an example, for each of the listed agents, the preferred and most preferred concentrations of an irrigation solution containing the listed agent are provided, such concentrations expected to be therapeutically effective when delivered locally. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period. In one embodiment, the preferred NO synthase inhibitors for inclusion in the solutions of the invention is 1400 W ((N-3-(aminomethyl)benzyl)acetamidine), a selective, slow, tight binding inhibitor of iNOS, diphenyleneiodinium and 1,3-PBIT.

TABLE 10

Therapeutic and Preferred Concentrations of Nitric Oxide Synthase Inhibitors

| Compounds | Local Delivery Therapeutic Concentrations (μM) | Most Preferred Local Delivery Concentrations (μM) |
|---|---|---|
| $N^G$-monomethyl-L-arginine | 50–50,000 | 3,000 |
| 1400 W | 0.1–1,000 | 1–20 |
| diphenyleneiodium | 0.1–1,000 | 1–100 |
| S-methyl isothiourea | 1–1,000 | 10–100 |
| S-(aminoethyl)isothiourea | 1–1,000 | 10–100 |
| L-$N^6$-(1-iminoethyl)lysine | 1–1,000 | 10–100 |
| 1,3-PBITU | 0.5–500 | 5–100 |
| 2-ethyl-2-thiopseudourea | 2–20,000 | 20–2,000 |

10. Cell Adhesion Molecules

10a. Integrin Agonists and Antagonists

Integrins are heterodimer receptors located on the plasma membrane that contain α and β subunits that bind ligands which are extracellular matrix (ECM) components or may be other large proteins, such as collagen, laminin, vitronectin, osteopontin (OPN) and fibronectin (FN). Degradation of the cartilage matrix is regulated by chondrocytes through mechanisms that depend upon the interaction of these cells with the ECM. Chondrocyte gene expression is, in part, controlled through cellular contacts involving the interaction of integrins with components of ECM in the environment surrounding the chondrocyte. Hence, integrins on chondrocytes are involved in control of cartilage homeostasis, and this family of receptors represents a class of therapeutic targets for preventing cartilage degradation.

Human chondrocytes express an array of integrin receptors composed of distinct α and β subunits, including $\alpha_1\beta_1$, $\alpha_5\beta_1$, $\alpha V\beta_3$ and lesser quantities of others. Of particular importance is the $\alpha V\beta_3$ integrin, which is known to bind OPN. The $\alpha V\beta_3$ complex-specific function blocking monoclonal antibody (mAb) LM609 acts as an agonist in a manner that is similar to the ligand, OPN. It attenuates the production of a number of proinflammatory and cartilage destructive mediators, such as IL-1, NO and PGE2. Thus, the agonistic mAb LM609 is thought to be suitable for use in the present invention.

In addition, two peptidomimetics, MK-383 (Merck) and RO 4483 (Hoffmann-LaRoche), have been studied in Phase II clinicals. Since these are both small molecules, they have a short half-life and high potency. However, these seem to also have less specificity, interacting with other closely related integrins. These peptidomimetics are also be suitable for use in the present invention.

TABLE 11

Therapeutic and Preferred Concentrations of Integrins

| Class of Agent | Local Delivery Therapeutic Concentrations (µg/ml) | Local Delivery Preferred Concentrations (µg/ml) |
|---|---|---|
| Integrins: | | |
| αVβ3 mAb LM 609 | 0.05–5,000 | 5–500 |
| echistatin | 0.1–10,000 | 100–1,000 |

11. Anti-Chemotactic Agents

Anti-chemotactic agents prevent the chemotaxis of inflammatory cells.

Representative examples of anti-chemotactic targets at which these agents would act include, but are not limited to, F-Met-Leu-Phe receptors, IL-8 receptors, MCP-1 receptors, and MIP-1-I/RANTES receptors. Drugs within this class of agents are early in the development stage, but it is theorized that they may be suitable for use in the present invention.

12. Intracellular Signaling Inhibitors

12a. Protein Kinase Inhibitors i. Protein Kinase C (PKC) Inhibitors

Protein kinase C (PKC) plays a crucial role in cell-surface signal transduction for a number of physiological processes. PKC isozymes can be activated as downstream targets resulting from initial activation of either G-protein coupled receptors (e.g., serotonin, bradykinin, etc.) or pro-inflammatory cytokine receptors. Both of these receptor classes play important roles in mediating cartilage destruction.

Molecular cloning analysis has revealed that PKC exists as a large family consisting of at least 8 subspecies (isozymes). These isozymes differ substantially in structure and mechanism for linking receptor activation to changes in the proliferative response of specific cells. Expression of specific isozymes is found in a wide variety of cell types, including: synoviocytes, chondrocytes, neutrophils, myeloid cells, and smooth muscle cells. Inhibitors of PKC are therefore likely to effect signaling pathways in several cell types unless the inhibitor shows isozyme specificity. Thus, inhibitors of PKC can be predicted to be effective in blocking the synoviocyte and chondrocyte activation and may also have an anti-inflammatory effect in blocking neutrophil activation and subsequent attachment. Several inhibitors have been described and initial reports indicate an $IC_{50}$ of 50 µM for calphostin C inhibitory activity. G-6203 (also known as Go 6976) is a new, potent PKC inhibitor with high selectivity for certain PKC isotypes with $IC_{50}$ values in the 2–10 µM range. Concentrations of these and another drug, GF 109203X, also known as Go 6850 or bisindoylmaleimide I (available from Warner-Lambert), that are believed to be suitable for local delivery use in the present invention are set forth below. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 12

Therapeutic and Preferred Concentrations of Cartilage Destruction Inhibitory Agents

| Class of Agent | Local Delivery Therapeutic Concentrations (Nanomolar) | Local Delivery Preferred Concentrations (Nanomolar) |
|---|---|---|
| Protein Kinase C Inhibitors: | | |
| calphostin C | 0.5–50,000 | 100–5,000 |
| GF 109203X | 0.1–10,000 | 1–1,000 |
| G-6203 (Go 6976) | 0.1–10,000 | 1–1,000 | ii. Protein Tyrosine Kinase Inhibitors

Figure 5:
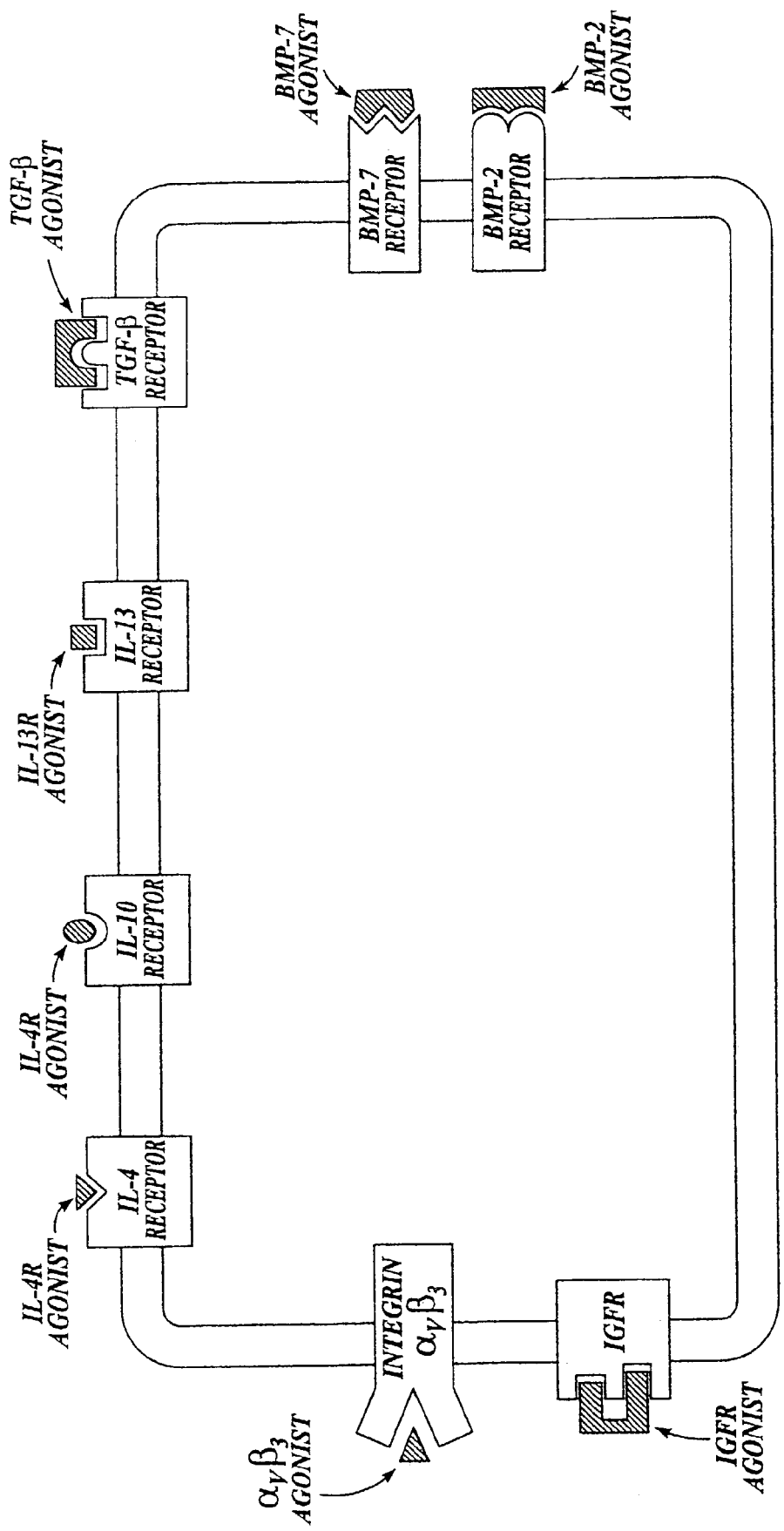
FIG. 5 is a diagram of molecular targets present on either chondrocytes or synoviocytes that promote an anabolic response of cartilage. Specific sites of action of some drugs in the preferred chondroprotective solution of the present are identified.
Figure 6:
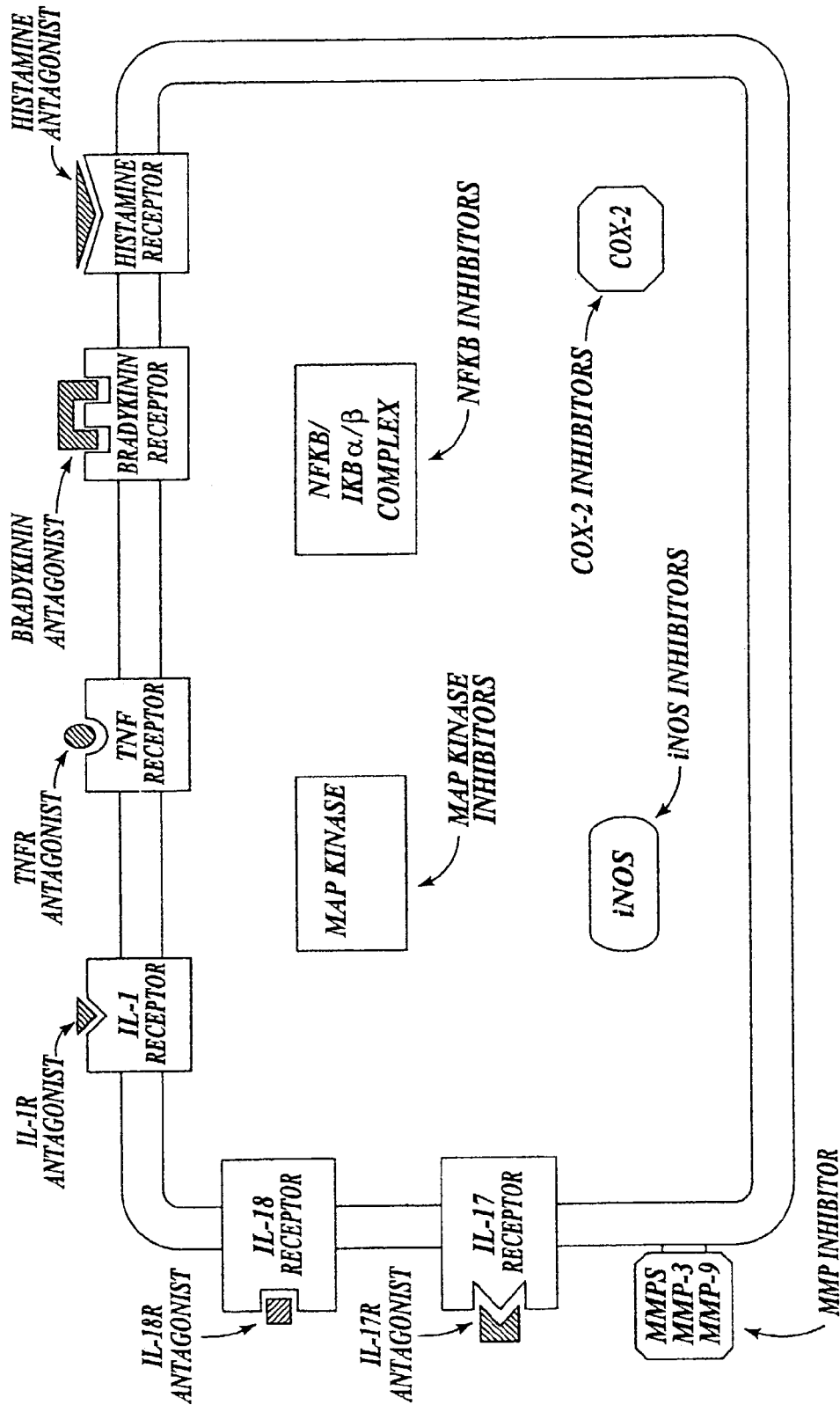
FIG. 6 is a diagram of molecular targets present on either chondrocytes or synoviocytes that promote a catabolic response in cartilage. Specific sites of action of some drugs in the preferred chondroprotective solution of the present invention are identified.

Although there is a tremendous diversity among the numerous members of the receptors tyrosine-kinase (RTK) family, the signaling mechanisms used by these receptors share many common features. Biochemical and molecular genetic studies have shown that binding of the ligand to the extracellular domain of the RTK rapidly activates the intrinsic tyrosine kinase catalytic activity of the intracellular domain (see FIG. 5). The increased activity results in tyrosine-specific phosphorylation of a number of intracellular substrates that contain a common sequence motif. Consequently, this causes activation of numerous "downstream" signaling molecules and a cascade of intracellular pathways that regulate phospholipid metabolism, arachidonate metabolism, protein phosphorylation (involving mechanisms other than protein kinases), calcium mobilization and transcriptional activation (see FIG. 2). Growth-factor-dependent tyrosine kinase activity of the RTK cytoplasmic domain is the primary mechanism for generation of intracellular signals that lead to cellular proliferation. Thus, inhibitors have the potential to block this signaling and thereby prevent synoviocyte and chondrocyte activation.

Any of several related tyrphostin compounds have potential as specific inhibitors of tyrosine kinase activity ($IC_{50}$s in vitro in the 0.5–1.0 µM range), since they have little effect on other protein kinases and other signal transduction systems. To date, only a few of the many tyrphostin compounds are commercially available, and suitable concentrations for these agents as used in the present invention are set forth below. In addition, staurosporine has been reported to demonstrate potent inhibitory effects against several protein tyrosine kinases of the src subfamily and a suitable concentration for this agent as used in the present invention for local delivery also is set forth below. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 13

Therapeutic and Preferred
Concentrations of Inhibitory Agents

| Class of Agent | Local Delivery Therapeutic Concentrations (Nanomolar) | Local Delivery Preferred Concentrations (Nanomolar) |
|---|---|---|
| Protein Kinase Inhibitors | | |
| lavendustin A | 10–100,000 | 100–10,000 |
| tyrphostin | 10–100,000 | 100–10,000 |
| AG1296 tyrphostin | 10–100,000 | 100–10,000 |
| AG1295 | 1–100,000 | 10–1,000 |
| staurosporine | | |
| PD 158780 | 0.1–10,000 | 10–500 |
| PD 174265 | 0.1–10,000 | 10–500 |

12b. Modulators of Intracellular Protein Tyrosine Phosphatases

Non-transmembrane protein tyrosine phosphatases (PTPases) containing src-homology$_2$ SH2 domains are known and nomenclature refers to them as SH-PTP1 and SH-PTP2. In addition, SH-PTP1 is also known as PTP1C, HCP or SHP. SH-PTP2 is also known as PTP1D or PTP2C. Similarly, SH-PTP1 is expressed at high levels in hematopoietic cells of all lineages and all stages of differentiation, and the SH-PTP1 gene has been identified as responsible for the motheaten (me) mouse phenotype and this provides a basis for predicting the effects of inhibitors that would block its interaction with its cellular substrates. Stimulation of neutrophils with chemotactic peptides is known to result in the activation of tyrosine kinases that mediate neutrophil responses (Cui, et al., *J. Immunol.* (1994)) and PTPase activity modulates agonist induced activity by reversing the effects of tyrosine kinases activated in the initial phases of cell stimulation. Agents that could stimulate PTPase activity could have potential therapeutic applications as anti-inflammatory mediators.

These same PTPases have also been shown to modulate the activity of certain RTKs. They appear to counter-balance the effect of activated receptor kinases and thus may represent important drug targets. In vitro experiments show that injection of PTPase blocks insulin stimulated phosphorylation of tyrosyl residues on endogenous proteins. Thus, activators of PTPase activity could serve to reverse activation of RTK-receptor action in restenosis, and are believed to be useful in the solutions of the present invention. In addition, receptor-linked PTPases also function as extracellular ligands, similar to those of cell adhesion molecules. The functional consequences of the binding of a ligand to the extracellular domain have not yet been defined but it is reasonable to assume that binding would serve to modulate phosphatase activity within cells (Fashena et al., *Current Biology*, 5;1367–1369 (1995)). Such actions could block adhesion mediated by other cell surface adhesion molecules (NCAM) and provide an anti-inflammatory effect. No drugs have been developed yet for these applications.

12c. Inhibitors of SH2 Domains (src Homology$_2$ Domains)

SH2 domains, originally identified in the src subfamily of protein tyrosine kinases (PTKs), are noncatalytic protein sequences and consist of about 100 amino acids conserved among a variety of signal transducing proteins (Cohen, et al., 1995). SH2 domains function as phosphotyrosine-binding modules and thereby mediate critical protein-protein associations in signal transduction pathways within cells (Pawson, *Nature*, 573–580, 1995). In particular, the role of SH2 domains has been clearly defined as critical for receptor tyrosine kinase (RTK) mediated signaling such as in the case of the platelet-derived growth factor (PDGF) receptor. Phosphotyrosine-containing sites on autophosphorylated RTKs serve as binding sites for SH2-proteins and thereby mediate the activation of biochemical signaling pathways (see FIG. 2) (Carpenter, G., *FASEB J.* 6:3283–3289 (1992); Sierke, S. et al., *J. Biochem.* 32:10102–10108 (1993)). The SH2 domains are responsible for coupling the activated growth-factor receptors to cellular responses that include alterations in gene expression, and ultimately cellular proliferation. Thus, inhibitors that will selectively block the effects of activation of specific RTKs (excluding IGFR and FGFR) expressed on the surface of synoviocytes are predicted to be effective in blocking cartilage degradation after arthroscopy procedures.

At least 20 cytosolic proteins have been identified that contain SH2 domains and function in intracellular signaling. The distribution of SH2 domains is not restricted to a particular protein family, but found in several classes of proteins, protein kinases, lipid kinases, protein phosphatases, phospholipases, Ras-controlling proteins and some transcription factors. Many of the SH2-containing proteins have known enzymatic activities while others (Grb2 and Crk) function as "linkers" and "adapters" between cell surface receptors and "downstream" effector molecules (Marengere, L., et al., *Nature* 369:502–505 (1994). Examples of proteins containing SH2 domains with enzymatic activities that are activated in signal transduction include, but are not limited to, the src subfamily of protein tyrosine kinases (src (pp60$^{c-src}$), abl, lck, fyn, fgr and others), phospholipaseCγ (PLCγ), phosphatidylinositol 3-kinase (PI-3-kinase), p21-ras GTPase activating protein (GAP) and SH2 containing protein tyrosine phosphatases (SH-PTPases) (Songyang, et al., *Cell* 72: 767–778 (1993). Due to the central role these various SH2-proteins occupy in transmitting signals from activated cell surface receptors into a cascade of additional molecular interactions that ultimately define cellular responses, inhibitors which block specific SH2 protein binding (e.g., c-src) are desirable as agents with potential therapeutic applications in cartilage protection.

In addition, the regulation of many immune/inflammatory responses is mediated through receptors that transmit signals through non-receptor tyrosine kinases containing SH2 domains. T-cell activation via the antigen specific T-cell receptor (TCR) initiates a signal transduction cascade leading to lymphokine secretion and T-cell proliferation. One of the earliest biochemical responses following TCR activation is an increase in tyrosine kinase activity. In particular, neutrophil activation is in part controlled through responses of the cell surface immunoglobulin G receptors. Activation of these receptors mediates activation of unidentified tyrosine kinases that are known to possess SH2 domains. Additional evidence indicates that several src-family kinases (lck, blk, fyn) participate in signal transduction pathways leading from cytokine and integrin receptors and hence may serve to integrate stimuli received from several independent receptor structures. Thus, inhibitors of specific SH2 domains have the potential to block many neutrophil functions and serve as anti-inflammatory mediators.

Efforts to develop drugs targeted to SH2 domains currently are being conducted at the biochemical in vitro and cellular level. Should such efforts be successful, it is theorized that the resulting drugs would be useful in the practice of the present invention.

V. Additional Agents

In addition to the chondroprotective agent(s) described above, locally and systemically delivered compositions of the present invention may also include other therapeutic agents. For example, one or more anti-inflammatory or analgesic agents (also referred to herein as anti-pain agents) may be included. Suitable examples of anti-inflammatory and/or analgesic agents are further described in detail below. As a further example, the compositions of the present invention may include one or more disease modifying anti-rheumatic drugs (DMARDs), such as methotrexate, sulfasalazine, gold compounds such as oral gold, gold sodium thiornalate and aurothioglucose, azathioprine, cyclosporine, antimalarials, steroids, colchicines, cyclophosphanmide, hydroxychloroquine sulfate, leflunomide, minocycline and penicillamine. The anti-inflammation, analgesic and/or DMARD agents may be included in the compositions of the present invention, or may be administered separately, either concurrently or sequentially.

Many of the aspects of the present invention regarding the previously addressed benefits of local administration, targeted systemic administration, and the use of multiple agents in connection with chondroprotective agents also applies to the administration of other agents. Alleviating pain and suffering in postoperative patients is an area of special focus in clinical medicine, especially with the growing number of outpatient operations performed each year. The most widely used systemic agents, cyclooxygenase inhibitors (e.g., ibuprofen) and opioids (e.g., morphine, fentanyl), have significant side effects including gastrointestinal irritation/bleeding and respiratory depression. The high incidence of nausea and vomiting related to opioids is especially problematic in the postoperative period. Therapeutic agents aimed at treating postoperative pain while avoiding detrimental side effects are not easily developed because the molecular targets for these agents are distributed widely throughout the body and mediate diverse physiological actions. Despite the significant clinical need to inhibit pain and inflammation, as well as cartilage degradation, methods for the delivery of inhibitors of pain, inflammation, and cartilage degradation at effective dosages while minimizing adverse systemic side effects have not been developed. As an example, systemic (i.e., intravenous, oral, subcutaneous or intramuscular) methods of administration of opiates in therapeutic doses frequently is associated with significant adverse side effects, including severe respiratory depression, changes in mood, mental clouding, profound nausea and vomiting.

Prior studies have demonstrated the ability of endogenous agents, such as serotonin (5-hydroxytryptamine, sometimes referred to herein as "5-HT"), bradykinin and histamine, to produce pain and inflammation. Sicuteri, F., et al., *Serotonin-Bradykinin Potentiation in the Pain Receptors in Man, Life Sci.* 4: 309–316 (1965); Rosenthal, S. R., *Histamine as the Chemical Mediator for Cutaneous Pain, J. Invest. Dermat.:* 98–105 (1977); Richardson, B. P., et al., *Identification of Serotonin M-Receptor Subtypes and their Specific Blockade by a New Class of Drugs, Nature* 316:, 126–131 (1985); Whalley, E. T., et al., *The Effect of Kinin Agonists and Antagonists, Naunyn-Schmiedeb Arch. Pharmacol.* 36: 652–57 (1987); Lang, E., et al., "Chemo-Sensitivity of Fine Afferents from Rat Skin In Vitro" *J. Neurophysiol.*: 887–901 (1990).

For example, 5-HT applied to a human blister base (denuded skin) has been demonstrated to cause pain that can be inhibited by $5-HT_3$ receptor antagonists. Richardson et al., (1985). Similarly, peripherally-applied bradykinin produces pain that can be blocked by bradykinin receptor antagonists. Sicuteri et al., 1965; Whalley et al., 1987; Dray, A., et al., "Bradykinin and Inflammatory Pain", *Trends Neurosci.* 16: 99–104 (1993). Peripherally-applied histamine produces vasodilation, itching and pain that can be inhibited by histamine receptor antagonists. Rosenthal, 1977; Douglas, W. W., "Histamine and 5-Hydroxytryptamine (Serotonin) and their Antagonists", in Goodman, L. S., et al., ed., *The Pharmacological Basis of Therapeutics*, MacMillan Publishing Company, New York, pp. 605–638 (1985); Rumore, M. M., et al., *Analgesic Effects of Antihistaminics*, Life Sci 36, pp. 403–416 (1985). Combinations of these three agonists (5-HT, bradykinin and histamine) applied together have been demonstrated to display a synergistic pain-causing effect, producing a long-lasting and intense pain signal. Sicuteri et al., 1965; Richardson et al., 1985; Kessler, W., et al., "Excitation of Cutaneous Afferent Nerve Endings In Vitro by a Combination of Inflammatory Mediators and Conditioning Effect of Substance P," *Exp. Brain Res.* 91:467–476 (1992).

In the body, 5-HT is located in platelets and in central neurons, histamine is found in mast cells, and bradykinin is produced from a larger precursor molecule during tissue trauma, pH changes and temperature changes. Because 5-HT can be released in large amounts from platelets at sites of tissue injury, producing plasma levels 20-fold greater than resting levels (Ashton, J. H., et al., "Serotonin as a Mediator of Cyclic Flow Variations in Stenosed Canine Coronary Arteries," *Circulation* 73:572–578 (1986)), it is possible that endogenous 5-HT plays a role in producing postoperative pain, hyperalgesia and inflammation. In fact, activation of platelets has been shown to result in excitation of peripheral nociceptors in vitro. Ringkamp, M., et al., "Activated Human Platelets in Plasma Excite Nociceptors in Rat Skin, In Vitro," *Neurosci. Lett.* 170:103–106 (1994). Similarly, histamine and bradykinin also are released into tissues during trauma. Kimura, E., et al., "Changes in Bradykinin Level in Coronary Sinus Blood After the Experimental Occlusion of a Coronary Artery," *Am Heart J.* 85:635–647 (1973); Douglas, 1985; Dray et al. (1993).

In addition, prostaglandins also are known to cause pain and inflammation. Cyclooxygenase inhibitors (e.g., ibuprofen) are commonly used in non-surgical and postoperative settings to block the production of prostaglandins, thereby reducing prostaglandin-mediated pain and inflammation. Flower, R. J., et al., *Analgesic-Antipyretics and Anti-Inflammatory Agents; Drugs Employed in the Treatment of Gout*, in Goodman, L. S., et al., ed., The Pharmacological Basis of Therapeutics, MacMillan Publishing Company, New York, pp. 674–715 (1985). Cyclooxygenase inhibitors are associated with some adverse systemic side effects when applied systemically. For example, indomethacin or ketorolac have well recognized gastrointestinal and renal adverse side effects.

As discussed, 5-HT, histamine, bradykinin and prostaglandins cause pain and inflammation. The various receptors through which these agents mediate their effects on peripheral tissues have been known and/or debated for the past two decades. Most studies have been performed in rats or other animal models. However, there are differences in pharmacology and receptor sequences between human and animal species.

Furthermore, antagonists of these mediators currently are not used for postoperative pain treatment. A class of drugs, termed 5-HT and norepinephrine uptake antagonists, which includes amitriptyline, has been used orally with moderate success for chronic pain conditions. However, the mechanisms of chronic versus acute pain states are thought to be considerably different. In fact, two studies in the acute pain setting using amitriptyline perioperatively have shown no pain-relieving effect of amitriptyline. Levine, J. D. et al., "Desipramine Enhances Opiate Postoperative Analgesia, *Pain* 27:45–49 (1986); Kerrick, J. M. et al., "Low-Dose Amitriptyline as an Adjunct to Opioids for Postoperative Orthopedic Pain: a Placebo-Controlled Trial Period," *Pain* 52:325–30 (1993). In both studies the drug was given orally. The second study noted that oral amitriptyline actually produced a lower overall sense of well being in postoperative patients, which may be due to the drug's affinity for multiple amine receptors in the brain.

Amitriptyline, in addition to blocking the uptake of 5-HT and norepinephrine, is a potent 5-HT receptor antagonist. Therefore, the lack of efficacy in reducing postoperative pain in the previously mentioned studies would appear to conflict with the proposal of a role for endogenous 5-HT in acute pain. There are a number of reasons for the lack of acute pain relief found with amitriptyline in these two studies. (1) The first study (Levine et al., 1986) used amitriptyline preoperatively for one week up until the night prior to surgery whereas the second study (Kerrick et al., 1993) only used amitriptyline postoperatively. Therefore, the level of amitriptyline that was present in the operative site tissues during the actual tissue injury phase, and the time at which 5-HT is purported to be released, is unknown. (2) Amitriptyline is known to be extensively metabolized by the liver. With oral administration, the concentration of amitriptyline in the operative site tissues may not have been sufficiently high for a long enough time period to inhibit the activity of postoperatively released 5-HT in the second study. (3) Since multiple inflammatory mediators exist, and studies have demonstrated synergism between the inflammatory mediators, blocking only one agent (5-HT) may not sufficiently inhibit the inflammatory response to tissue injury.

There have been a few studies demonstrating the ability of extremely high concentrations (1%–3% solutions—i.e., 10–30 mg per milliliter) of histamine$_1$ (H$_1$) receptor antagonists to act as local anesthetics for surgical procedures. This anesthetic effect is not believed to be mediated via H$_1$ receptors but, rather, due to a non-specific interaction with neuronal membrane sodium channels (similar to the action of lidocaine). Given the side effects (e.g., sedation) associated with these high "anesthetic" concentrations of histamine receptor antagonists, local administration of histamine receptor antagonists currently is not used in the perioperative setting.

A. Synergistic Interactions Derived from Therapeutic Combinations of Anti-Pain and/or Anti-Inflammation Agents and Chondroprotective Agents Given the complexity of the disease process associated with inflammation and loss of cartilage homeostasis after arthroscopic therapeutic procedures and the multiplicity of molecular targets involved, blockade or inhibition of a single molecular target is unlikely to provide adequate efficacy in preventing cartilage degradation and the development of osteoarthritis. Indeed, a number of animal studies targeting different individual molecular receptors and or enzymes have not proven effective in animal models or have not yielded efficacy in clinical trials to date. Therefore, a therapeutic combination of drugs acting on distinct molecular targets and delivered locally or systemically appears desirable for clinical effectiveness in the therapeutic approach to cartilage protection. As described below, the rationale for this synergistic molecular targeted therapy is derived from recent advances in understanding fundamental biochemical mechanisms by which synoviocyte and chondrocyte cells in the synovium and cartilage transmit and integrate stimuli to which they are exposed during arthroscopic procedures.

The molecular switches responsible for cell signaling have been traditionally divided into major discrete signaling pathways, each comprising a distinct set of protein families that act as transducers for a particular set of extracellular stimuli and mediating distinct cell responses. One such pathway transduces signals from neurotransmitters and hormones through G-protein coupled receptors (GPCRs) to produce contractile responses that include the production of inflammatory mediators, such as PGE2. The GPCRs couple to intracellular targets through activation of trimeric G proteins (see FIG. 2). Examples of signaling molecules involved in activation of synoviocytes and chondrocytes through the GPCR pathway are histamine, bradykinin, serotonin and ATP. A second major pathway transduces signals from pro-inflammatory cytokines, such as IL-1, through a kinase cascade and NF-6B protein into regulation of gene expression and the production of catabolic cytokines and other catabolic factors, including NO.

Figure 3:
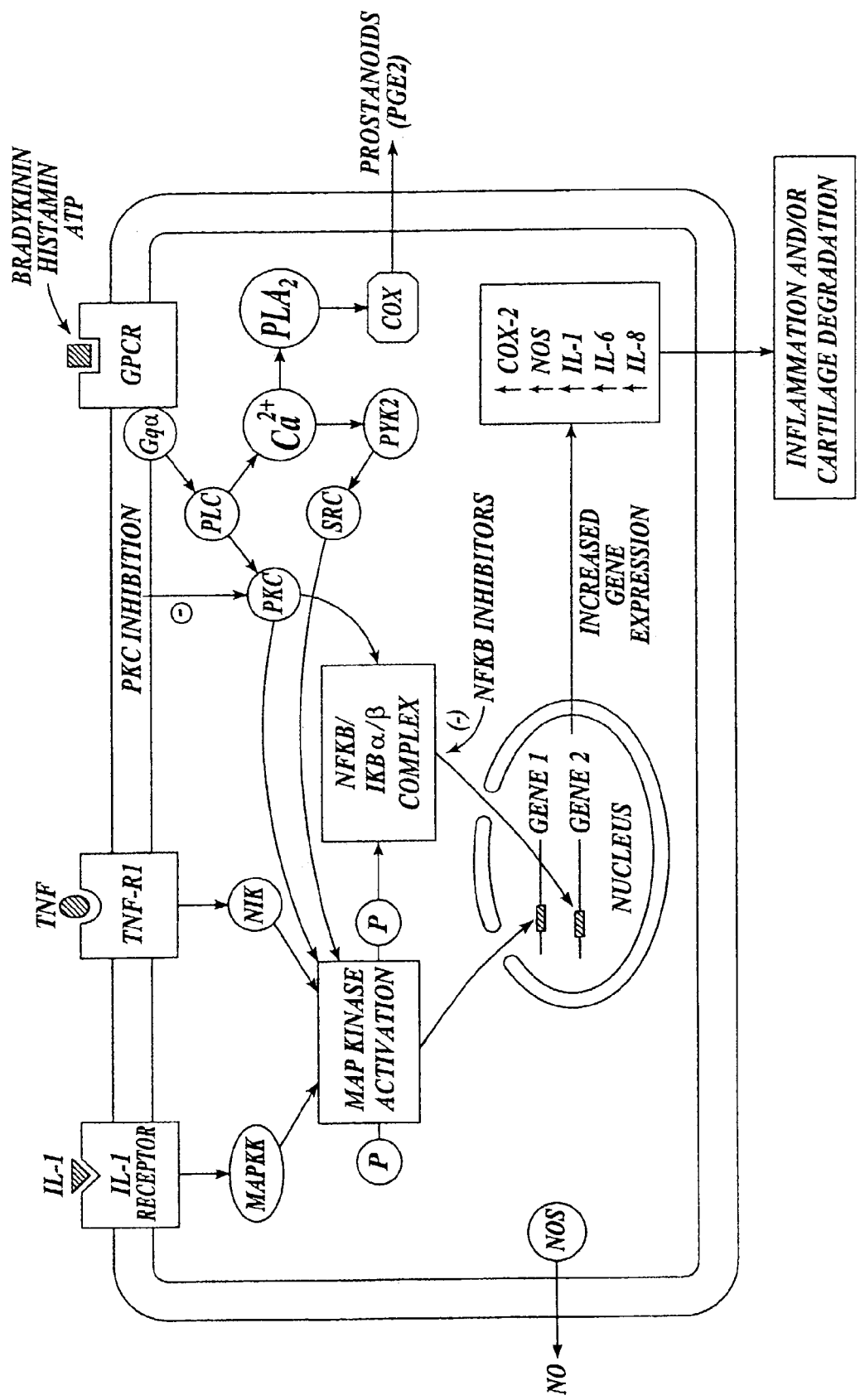
FIG. 3 is a diagram of common signaling pathways in both chondrocyte and synoviocyte cells, including key signaling proteins responsible for "crosstalk" between GPCR activated receptor pathways and pro-inflammatory cytokine pathways that lead to inflammation and or cartilage degradation.

Signals transmitted from neurotransmitters and hormones stimulate either of two classes of receptors: GPCRs, composed of seven-helix transmembrane regions, or ligand-gated ion channels. "Downstream" signals from both kinds of receptors converge on controlling the concentration of cytoplasmic Ca$^{2+}$ (see FIG. 3). Each GPCR transmembrane receptor activates a specific class of trimeric G proteins, including G$_q$, G$_i$ or many others. G$_q$ subunits activate phospholipase Cγ, resulting in activation of protein kinase C (PKC) and an increase in the levels of cytoplasmic calcium (FIG. 3). In turn, elevated intracellular calcium leads to the activation of cPLA2 and the production of arachidonic acid (AA). The AA serves as a substrate for COX in both synoviocytes and chondrocytes, leading to the production of PGE2. PKC activation also results in activation of MAP kinase leading to activation of NF-B and, in cells and tissues which have been primed by exposure to pro-inflammatory cytokines, modulates increased gene expression of proteins involved in cartilage catabolism.

Figure 2:
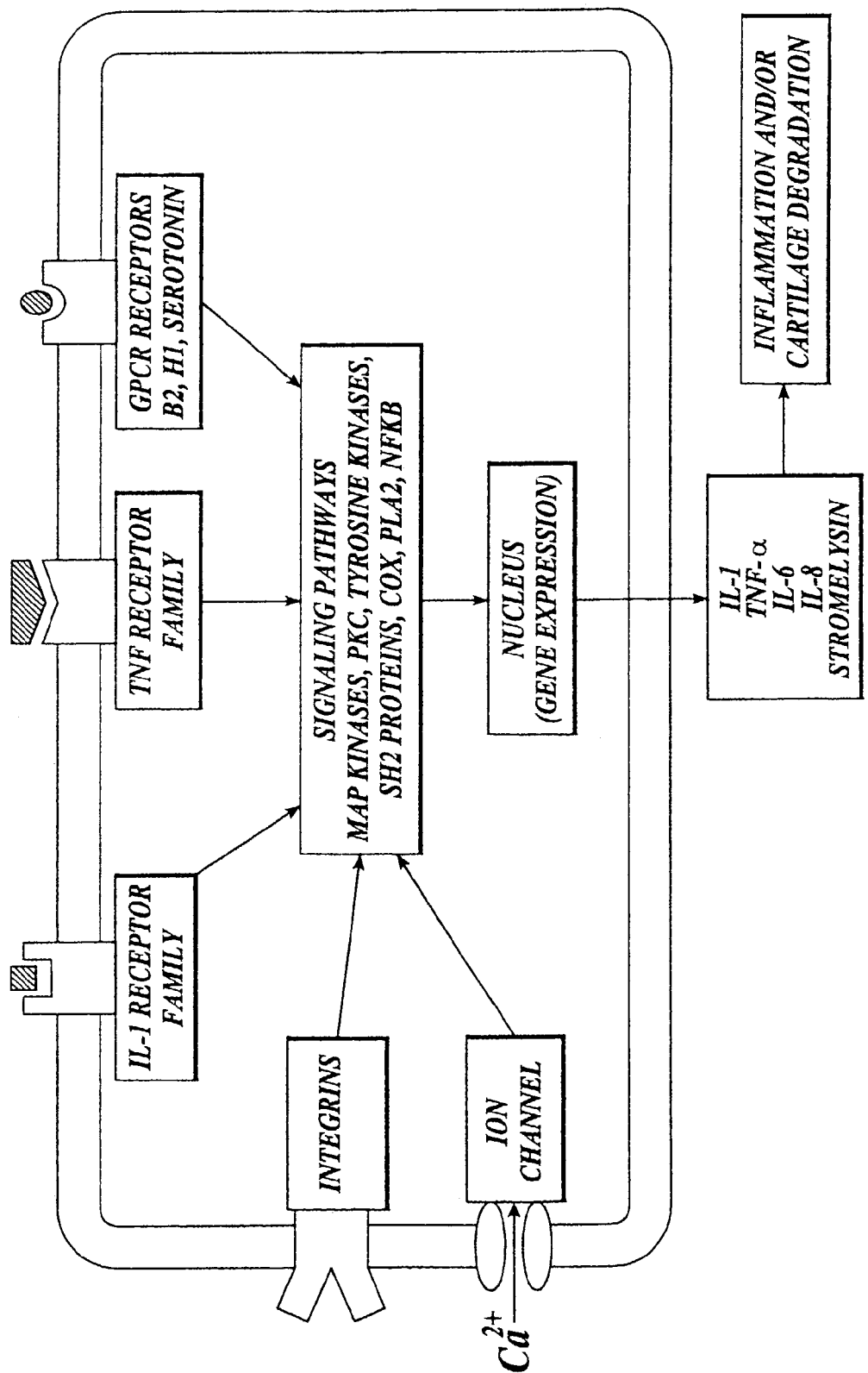
FIG. 2 provides a schematic overview of a synoviocyte cell showing molecular targets and flow of signaling information leading to the production of mediators of inflammation and shifts in cartilage metabolism. The integration of extrinsic signals through several families of cell surface receptors, including cytokine receptors which include the interleukin-1 (IL-1) receptor family and the tumor necrosis factor (TNF) receptor family, the G-protein coupled receptors which include bradykinin, histamine and serotonin subtypes, and integrins is shown to converge on common intracellular signaling pathways that include major groups of protein molecules that are therapeutic targets of drugs included in the solutions of the present invention (MAP kinases, PKC, tyrosine kinases, SH2 proteins, COX, PLA2 and NF-6B). Activation of these signaling pathways controls synoviocyte expression of a number of inducible gene products, including IL-1, TNF-α, IL-6, IL-8 and Stromelysin (MMP-3), which may lead to inflammation and/or cartilage degradation.
Figure 4:
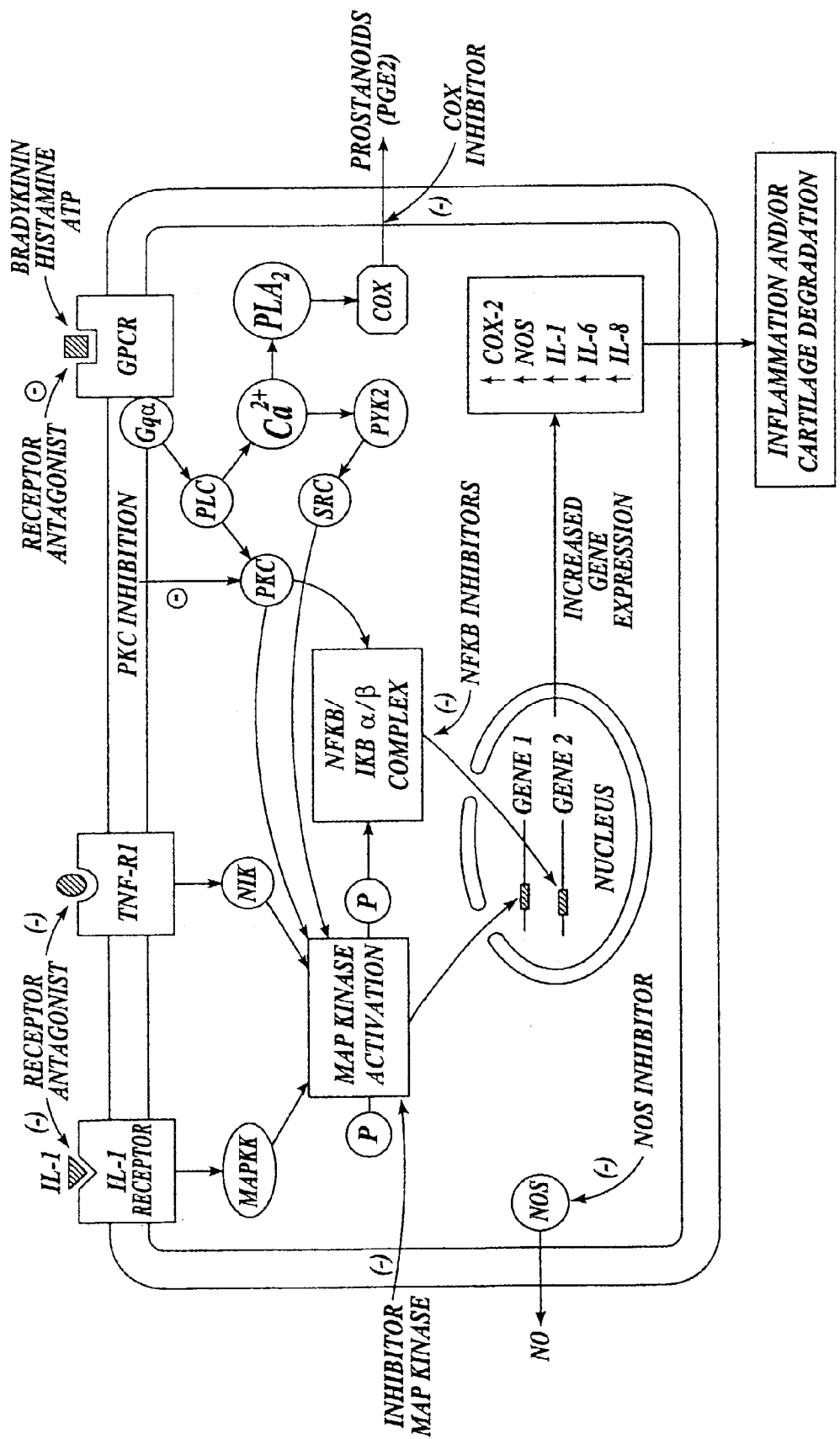
FIG. 4 is a diagram of common signaling pathways in both chondrocyte and synoviocyte cells, including key signaling proteins responsible for "crosstalk" between GPCR activated receptor pathways and pro-inflammatory cytokine pathways. Specific molecular sites of action for some drugs in a preferred chondroprotective solution of the present invention are identified.

Pro-inflammatory cytokine signaling, such as mediated by both IL-1 and TNF-α through their distinct cognate receptors, also converges on regulation of cell gene expression. The signal transduction pathways utilized by these distinct receptors, employ distinct kinases that are proximal to the receptors but the signaling pathways subsequently converge at the level of MAP kinases (FIGS. 3 and 4). Signal transduction depends upon phosphorylation of residues in a cascade of kinases, including "downstream" enzymes such as p38 MAP kinase. Activation of the IL-1-receptor and TNF-receptor also leads to stimulation of MAP kinase, common steps shared by the Gq coupled GPCRs (see FIG. 3). It is now recognized that ligand-independent "crosstalk" can transactivate kinase pathways in response to costimulation of specific GPCRs and cytokines such as IL-1, leading to synergistic cellular responses (see FIG. 3). Thus, a combination of selective inhibitors which blocks transactivation of a common signaling pathway (as shown in FIGS. 1 and 2) leading to increased gene expression of pro-inflammatory cytokines, iNOS, COX-2, and MMPs will act synergistically to prevent inflammation and cartilage degradation after arthroscopic surgical procedures.

B. Anti-Inflammation and Anti-Pain Agents

Suitable classes of anti-inflammation and/or anti-pain agents for use in the compositions and methods of the present invention include: (1) serotonin receptor antagonists; (2) serotonin receptor agonists; (3) histamine receptor antagonists; (4) bradykinin receptor antagonists; (5) kallikrein inhibitors; (6) tachykinin receptor antagonists, including neurokinin$_1$ and neurokintin$_2$ receptor subtype antagonists; (7) calcitonin gene-related peptide (CGRP) receptor antagonists; (8) interleukin receptor antagonists; (9) inhibitors of enzymes active in the synthetic pathway for arachidonic acid metabolites, including (a) phospholipase inhibitors, including PLA$_2$ isoform inhibitors and PLC isoform inhibitors (b) cyclooxygenase inhibitors, and (c) lipooxygenase inhibitors; (10) prostanoid receptor antagonists including eicosanoid EP-1 and EP-4 receptor subtype antagonists and thromboxane receptor subtype antagonists; (11) leukotriene receptor antagonists including leukotriene B$_4$ receptor subtype antagonists and leukotriene D$_4$ receptor subtype antagonists; (12) opioid receptor agonists, including μ-opioid, δ-opioid, and κ-opioid receptor subtype agonists; (13) purinoceptor agonists and antagonists including P$_{2X}$ receptor antagonists and P$_{2Y}$ receptor antagonists; and (14) calcium channel antagonists.

The following is a description of suitable drugs falling in each of the aforementioned classes of anti-inflammation/anti-pain agents, as well as suitable concentrations for use in solutions, of the present invention intended to be delivered locally. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period. While not wishing to be limited by theory, the justification behind the selection of the various classes of agents which is believed to render the agents operative is also set forth.

Each agent is preferably included at a low concentration of 0.1 to 10,000 times $K_d$ or $K_i$, except for cyclooxygenase inhibitors, which may be required at larger concentrations depending on the particular inhibitor selected. Preferably, each agent is included at a concentration of 1.0 to 1,000 times $K_d$ or $K_i$ and most preferably at approximately 100 times $K_d$ or $K_i$. These concentrations are adjusted as needed to account for dilution in the absence of metabolic transformation at the local delivery site. The exact agents selected for use in the solution, and the concentration of the agents, varies in accordance with the particular application, as described below.

1. Serotonin Receptor Antagonists

Serotonin (5-HT) is thought to produce pain by stimulating serotonin$_2$ (5-HT$_2$) and/or serotonin$_3$ (5-HT$_3$) receptors on nociceptive neurons in the periphery. Most researchers agree that 5-HT$_3$ receptors on peripheral nociceptors mediate the immediate pain sensation produced by 5-HT (Richardson et al., 1985). In addition to inhibiting 5-HT-induced pain, 5-HT$_3$ receptor antagonists, by inhibiting nociceptor activation, also may inhibit neurogenic inflammation. Barnes P. J., et al., "Modulation of Neurogenic Inflammation: Novel Approaches to Inflammatory Disease", *Trends in Pharmacological Sciences* 11: 185–189 (1990). A study in rat ankle joints, however, claims the 5-HT$_2$ receptor is responsible for nociceptor activation by 5-HT. Grubb, B. D., et al., "A Study of 5-HT-Receptors Associated with Afferent Nerves Located in Normal and Inflamed Rat Ankle Joints", *Agents Actions* 25: 216–18 (1988). Therefore, activation of 5-HT$_2$ receptors also may play a role in peripheral pain and neurogenic inflammation.

One goal of the solution of the present invention is to block pain and a multitude of inflammatory processes. Thus, 5-HT$_2$ and 5-HT$_3$ receptor antagonists are both suitably used, either individually or together, in the solution of the present invention, as shall be described subsequently. Amitriptyline (Elavil™) is a suitable 5-HT$_2$ receptor antagonist for use in the present invention. Amitriptyline has been used clinically for numerous years as an anti-depressant, and is found to have beneficial effects in certain chronic pain patients. Metoclopramide (Reglan™) is used clinically as an anti-emetic drug, but displays moderate affinity for the 5-HT$_3$ receptor and can inhibit the actions of 5-HT at this receptor, possibly inhibiting the pain due to 5-HT release from platelets. Thus, it also is suitable for use in the present invention.

Other suitable 5-HT$_2$ receptor antagonists include imipramine, trazodone, desipramine and ketanserin. Ketanserin has been used clinically for its anti-hypertensive effects. Hedner, T., et al., "Effects of a New Serotonin Antagonist, Ketanserin, in Experimental and Clinical Hypertension", *Am J of Hypertension* 317s-23s (July 1988). Other suitable 5-HT$_3$ receptor antagonists include cisapride and ondansetron. Suitable serotonin$_{1B}$ receptor antagonists include yohimbine, N-[methoxy-3-(4-methyl-1-piperazinyl)phenyl]-2'-methyl-4'-(5-methyl-1,2,4-oxadiazol-3-yl)[1,1-biphenyl]-4-carboxamide ("GR127935") and methiothepin. Therapeutic and preferred concentrations for local delivery use of these drugs in the solution of an aspect the present invention are set forth in Table 14. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 14

Therapeutic and Preferred Concentrations of Pain and/or Inflammation Inhibitory Agents

| Class of Agent | Local Delivery Therapeutic Concentrations (Nanomolar) | Local Delivery Preferred Concentrations (Nanomolar) |
|---|---|---|
| Serotonin$_2$ Receptor Antagonists: | | |
| Amitriptyline | 0.1–1,000 | 50–500 |
| MDL-11,939 | 0.1–1,000 | 50–500 |
| AMI-193 | 0.1–2,000 | 50–500 |
| Desipramine | 0.1–1,000 | 50–500 |
| Ketanserin | 0.1–1,000 | 50–500 |
| Serotonin$_3$ Receptor Antagonists: | | |
| Tropisetron | 0.01–100 | 0.05–50 |
| Metoclopramide | 10–10,000 | 200–2,000 |
| Cisapride | 0.1–1,000 | 20–200 |
| Ondansetron | 0.1–1,000 | 20–200 |

TABLE 14-continued

Therapeutic and Preferred Concentrations of
Pain and/or Inflammation Inhibitory Agents

| Class of Agent | Local Delivery Therapeutic Concentrations (Nanomolar) | Local Delivery Preferred Concentrations (Nanomolar) |
|---|---|---|
| Serotonin$_{1B}$ (Human 1D$_\beta$) Antagonists: | | |
| Isamoltare | 0.1–1,000 | 50–500 |
| GR127935 | 0.1–1,000 | 10–500 |
| Methiothepin | 0.1–500 | 1–100 |
| SB216641 | 0.2–2,000 | 2–200 |

2. Serotonin Receptor Agonists

5-HT$_{1A}$, 5-HT$_{1B}$ and 5-HT$_{1D}$ receptors are known to inhibit adenylate cyclase activity. Thus including a low dose of these serotonin$_{1A}$, serotonin$_{1B}$ and serotonin$_{1D}$ receptor agonists in the solution should inhibit neurons mediating pain and inflammation. The same action is expected from serotonin$_{1E}$ and serotonin$_{1F}$ receptor agonists because these receptors also inhibit adenylate cyclase.

Buspirone is a suitable 1A receptor agonist for use in the present invention. Sumatriptan is a suitable 1A, 1B, 1D and 1F receptor agonist. A suitable 1B and 1D receptor agonist is dihydroergotamine. A suitable 1E receptor agonist is ergonovine. Therapeutic and preferred concentrations for these receptor agonists when delivered locally are provided in Table 15. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 15

Therapeutic and Preferred Concentrations
of Pain and/or inflammation Inhibitory Agents

| Class of Agent | Local Delivery Therapeutic Concentrations (Nanomolar) | Local Delivery Preferred Concentrations (Nanomolar) |
|---|---|---|
| Serotonin$_{1A}$ Agonists: | | |
| Buspirone | 1–1,000 | 10–200 |
| Sumatriptan | 1–1,000 | 10–200 |
| Serotonin$_{1B}$ Agonists: | | |
| Dihydroergotamine | 0.1–1,000 | 10–100 |
| Sumatriptan | 1–1,000 | 10–200 |
| Naratriptan | 1–1,000 | 10–200 |
| Rizatriptan | 1–1,000 | 10–200 |
| Zolmitriptan | 1–1,000 | 10–200 |
| L-694,247 | 1–1,000 | 10–200 |
| Serotonin$_{1D}$ Agonists: | | |
| Dihydroergotamine | 0.1–1,000 | 10–100 |
| Sumatriptan | 1–1,000 | 10–200 |
| Naratriptan | 1–1,000 | 10–200 |
| Rizatriptan | 1–1,000 | 10–200 |
| Zolmitriptan | 1–1,000 | 10–200 |
| L-694,247 | 1–1,000 | 10–200 |
| Serotonin$_{1E}$ Agonists: | | |
| Ergonovine | 10–2,000 | 100–1,000 |

TABLE 15-continued

Therapeutic and Preferred Concentrations
of Pain and/or inflammation Inhibitory Agents

| Class of Agent | Local Delivery Therapeutic Concentrations (Nanomolar) | Local Delivery Preferred Concentrations (Nanomolar) |
|---|---|---|
| Serotonin$_{1F}$ Agonists: | | |
| Sumatriptan | 1–1,000 | 10–200 |

3. Histamine Receptor Antagonists

Histamine receptors generally are divided into histamine$_1$ (H$_1$) and histamine$_2$ (H$_2$) subtypes. The classic inflammatory response to the peripheral administration of histamine is mediated via the H$_1$ receptor. Douglas, 1985. Therefore, the solution of the present invention preferably includes a histamine H$_1$ receptor antagonist. Promethazine (Phenergan™) is a commonly used anti-emetic drug that potently blocks H$_1$ receptors, and is suitable for use in the present invention. Interestingly, this drug also has been shown to possess local anesthetic effects but the concentrations necessary for this effect are several orders higher than that necessary to block H$_1$ receptors, thus, the effects are believed to occur by different mechanisms. The histamine receptor antagonist concentration in the solution is sufficient to inhibit H$_1$ receptors involved in nociceptor activation, but not to achieve a "local anesthetic" effect, thereby eliminating the concern regarding systemic side effects.

Other suitable H$_1$ receptor antagonists include terfenadine, diphenhydramine, amitriptyline, mepyramine and tripolidine. Because amitriptyline is also effective as a serotonin$_2$ receptor antagonist, it has a dual function as used in the present invention. Suitable therapeutic and preferred concentrations for each of these H$_1$ receptor antagonists for local delivery are set forth in Table 16. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 16

Therapeutic and Preferred Concentrations
of Pain and/or inflammation Inhibitory Agents

| Class of Agent | Local Delivery Therapeutic Concentrations (Nanomolar) | Local Delivery Preferred Concentrations (Nanomolar) |
|---|---|---|
| Histamine$_1$ Receptor Antagonists: | | |
| Promethazine | 0.1–1,000 | 50–200 |
| Diphenhydramine | 0.1–1,000 | 50–200 |
| Amitriptyline | 0.1–1,000 | 50–500 |
| Terfenadine | 0.1–1,000 | 50–500 |
| mepyramine (pyrilamine) | 0.1–1,000 | 5–200 |
| Tripolidine | 0.01–100 | 5–20 |

4. Bradykinin Receptor Antagonists

Bradykinin receptors generally are divided into bradykinin$_1$ (B$_1$) and bradykinin$_2$ (B$_2$) subtypes. Studies have shown that acute peripheral pain and inflammation produced by bradykinin are mediated by the $B_2$ subtype whereas bradykinin-induced pain in the setting of chronic inflammation is mediated via the $B_1$ subtype. Perkins, M. N., et al., "Antinociceptive Activity of the Bradykinin B1 and B2 Receptor Antagonists, des-Arg$^9$, [Leu$^8$]-BK and HOE 140, in Two Models of Persistent Hyperalgesia in the Rat", *Pain* 53: 191–97 (1993); Dray, A., et al., "Bradykinin and Inflammatory Pain", *Trends Neurosci.* 16: 99–104 (1993), each of which references is hereby expressly incorporated by reference.

At present, bradykinin receptor antagonists are not used clinically. Some of these drugs are peptides, and thus they cannot be taken orally, because they would be digested. Antagonists to $B_2$ receptors block bradykinin-induced acute pain and inflammation. Dray et al., 1993. $B_1$ receptor antagonists inhibit pain in chronic inflammatory conditions. Perkins et al., 1993; Dray et al., 1993. Therefore, depending on the application, the solution of the present invention preferably includes either or both bradykinin $B_1$ and $B_2$ receptor antagonists. For example, arthroscopy is performed for both acute and chronic conditions, and thus an irrigation solution for arthroscopy could include both $B_1$ and $B_2$ receptor antagonists.

Suitable bradykinin receptor antagonists for use in the present invention include the following bradykinin$_1$ receptor antagonists: the [des-Arg$^{10}$] derivative of D-Arg-(Hyp$^3$-Thi$^5$-D-Tic$^7$-Oic$^8$)-BK ("the [des-Arg$^{10}$] derivative of HOE 140", available from Hoechst Pharmaceuticals); and [Leu$^8$] des-Arg$^9$-BK. Suitable bradykinin$_2$ receptor antagonists include: [D-Phe$^7$]-BK; D-Arg-(Hyp$^3$-Thi$^{5,8}$-D-Phe$^7$)-BK ("NPC 349"); D-Arg-(Hyp$^3$-D-Phe$^7$)-BK ("NPC 567"); and D-Arg-(Hyp$^3$-Thi$^5$-D-Tic$^7$-Oic$^8$)-BK ("HOE 140"). These compounds are more fully described in the previously incorporated Perkins et al. 1993 and Dray et al. 1993 references. Suitable therapeutic and preferred concentrations for local delivery are provided in Table 17. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 17

Therapeutic and Preferred Concentrations of
Pain and/or inflammation Inhibitory Agents

| Class of Agent | Local Delivery Therapeutic Concentrations (Nanomolar) | Local Delivery Preferred Concentrations (Nanomolar) |
|---|---|---|
| Bradykinin$_1$ Receptor Antagonists: | | |
| [Leu$^8$] des-Arg$^9$-BK | 1–1,000 | 50–500 |
| [des-Arg$^{10}$] derivative of HOE 140 | 1–1,000 | 50–500 |
| [leu$^9$] [des-Arg$^{10}$] kalliden | 0.1–500 | 10–200 |
| Bradykinin$_2$ Receptor Antagonists: | | |
| [D-Phe$^7$]-BK | 100–10,000 | 200–5,000 |
| NPC 349 | 1–1,000 | 50–500 |
| NPC 567 | 1–1,000 | 50–500 |
| HOE 140 | 1–1,000 | 50–500 |

5. Kallikrein Inhibitors

The peptide bradykinin is an important mediator of pain and inflammation, as noted previously. Bradykinin is produced as a cleavage product by the action of kallikrein on high molecular weight kininogens in plasma. Therefore kallikrein inhibitors are believed to be therapeutic in inhibiting bradykinin production and resultant pain and inflammation. A suitable kallikrein inhibitor for use in the present invention is aprotinin. Suitable concentrations for use in the solutions of the present invention when delivered locally are set forth below in Table 18. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 18

Therapeutic and Preferred Concentrations of
Pain and/or inflammation Inhibitory Agents

| Class of Agent | Local Delivery Therapeutic Concentrations (Nanomolar) | Local Delivery Preferred Concentrations (Nanomolar) |
|---|---|---|
| Kallikrein Inhibitor: | | |
| Aprotinin | 0.1–1,000 | 50–500 |

6. Tachykinin Receptor Antagonists

Tachykinins (TKs) are a family of structurally related peptides that include substance P, neurokinin A (NKA) and neurokinin B (NKB). Neurons are the major source of TKs in the periphery. An important general effect of TKs is neuronal stimulation, but other effects include endothelium-dependent vasodilation, plasma protein extravasation, mast cell recruitment and degranulation and stimulation of inflammatory cells. Maggi, C. A., *Gen. Pharmacol.*, 22: 1–24 (1991). Due to the above combination of physiological actions mediated by activation of TK receptors, targeting of TK receptors is a reasonable approach for the promotion of analgesia and the treatment of neurogenic inflammation.

6a. Neurokinin$_1$ Receptor Subtype Antagonists

Substance P activates the neurokinin receptor subtype referred to as NK$_1$. Substance P is an undecapeptide that is present in sensory nerve terminals. Substance P is known to have multiple actions that produce inflammation and pain in the periphery after C-fiber activation, including vasodilation, plasma extravasation and degranulation of mast cells. Levine, J. D., et al., "Peptides and the Primary Afferent Nociceptor", *J. Neurosci.* 13: 2273 (1993). A suitable Substance P antagonist is ([D-Pro$^9$[spiro-gamma-lactam]Leu$^{10}$, Trp$^{11}$]physalaemin-(1-11)) ("GR 82334"). Other suitable antagonists for use in the present invention which act on the NK$_1$ receptor are: 1-imino-2-(2-methoxy-phenyl)-ethyl)-7,7-diphenyl-4-perhydroisoindolone(3aR,7aR) ("RP 67580"); and 2S,3S-cis-3-(2-methoxybenzylamino)-2-benzhydrylquinuclidine ("CP 96,345"). Suitable concentrations for these agents when delivered locally are set forth in Table 19. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 19

Therapeutic and Preferred Concentrations of Pain and/or inflammation Inhibitory Agents

| Class of Agent | Local Delivery Therapeutic Concentrations (Nanomolar) | Local Delivery Preferred Concentrations (Nanomolar) |
|---|---|---|
| Neurokinin$_1$ Receptor Subtype Antagonists | | |
| GR 82334 | 1–1,000 | 10–500 |
| CP 96,345 | 1–10,000 | 100–1,000 |
| RP 67580 | 0.1–1,000 | 100–1,000 |

6b. Neurokinin$_2$ Receptor Subtype Antagonists

Neurokinin A is a peptide which is colocalized in sensory neurons with substance P and which also promotes inflammation and pain. Neurokinin A activates the specific neurokinin receptor referred to as NK$_2$. Edmonds-Alt, S., et al., "A Potent and Selective Non-Peptide Antagonist of the Neurokinin A (NK$_2$) Receptor", *Life Sci.* 50:PL101 (1992). Examples of suitable NK$_2$ antagonists include: ((S)-N-methyl-N-[4-(4-acetylamino-4-phenylpiperidino)-2-(3,4-dichlorophenyl)butyl]-benzamide ("(±)-SR 48968"); Met-Asp-Trp-Phe-Dap-Leu ("MEN 10,627"); and cyc(Gln-Trp-Phe-Gly-Leu-Met) ("L 659,877"). Suitable concentrations of these agents for local delivery are provided in Table 20. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 20

Therapeutic and Preferred Concentrations of Pain and/or inflammation Inhibitory Agents

| Class of Agent | Local Delivery Therapeutic Concentrations (Nanomolar) | Local Delivery Preferred Concentrations (Nanomolar) |
|---|---|---|
| Neurokinin$_2$ Receptor Subtype Antagonists: | | |
| MEN 10,627 | 1–1,000 | 10–1,000 |
| L 659,877 | 10–10,000 | 100–10,000 |
| (±)-SR 48968 | 10–10,000 | 100–10,000 |

7. CGRP Receptor Antagonists

Calcitonin gene-related peptide (CGRP) is a peptide which is also colocalized in sensory neurons with substance P, and which acts as a vasodilator and potentiates the actions of substance P. Brain, S., et al., *Br. J. Pharmacol.* 99: 202 (1985). An example of a suitable CGRP receptor antagonist is I-CGRP-(8-37), a truncated version of CGRP. This polypeptide inhibits the activation of CGRP receptors. Suitable concentrations for this agent when delivered locally are provided in Table 21. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 21

Therapeutic and Preferred Concentrations of Pain and/or inflammation Inhibitory Agents

| Class of Agent | Local Delivery Therapeutic Concentrations (Nanomolar) | Local Delivery Preferred Concentrations (Nanomolar) |
|---|---|---|
| CGRP Receptor Antagonist: | | |
| I-CGRP-(8–37) | 1–1,000 | 10–500 |

8. Interleukin Receptor Antagonist

Interleukins are a family of peptides, classified as cytokines, produced by leukocytes and other cells in response to inflammatory mediators. Interleukins (IL) may be potent hyperalgesic agents peripherally. Ferriera, S. H., et al., *Nature* 334: 698 (1988). An example of a suitable IL-1β receptor antagonist is Lys-D-Pro-Thr, which is a truncated version of IL-1β. This tripeptide inhibits the activation of IL-1β receptors. Suitable concentrations for this agent for local delivery are provided in Table 22. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 22

Therapeutic and Preferred Concentrations of Pain and/or Inflammation Inhibitory Agents

| Class of Agent | Local Delivery Therapeutic Concentrations (Nanomolar) | Local Delivery Preferred Concentrations (Nanomolar) |
|---|---|---|
| Interleukin Receptor Antagonist: | | |
| Lys-D-Pro-Thr | 1–1,000 | 10–500 |

9. Inhibitors of Enzymes Active in the Synthetic Pathway for Arachidonic Acid Metabolites 9a. Phospholipase Inhibitors The production of arachidonic acid by phospholipase A$_2$ (PLA$_2$) enzymes (cPLA$_2$, iPLA$_2$, sPLA$_2$) and phospholipase C (PLC) results in a cascade of reactions that produces numerous mediators of inflammation, know as eicosanoids. There are a number of stages throughout this pathway that can be inhibited, thereby decreasing the production of these inflammatory mediators. Examples of inhibition at these various stages are given below.

Inhibition of the enzyme PLA$_2$ isoform inhibits the release of arachidonic acid from cell membranes, and therefore inhibits the production of prostaglandins and leukotrienes resulting in decreased inflammation and pain. Glaser, K. B., "Regulation of Phospholipase A2 Enzymes: Selective Inhibitors and Their Pharmacological Potential", *Adv. Pharmacol.* 32:31 (1995). An example of a suitable $PLA_2$ isoform inhibitor is manoalide. Inhibition of the phospholipase $C_\gamma$ ($PLC_\gamma$) isoform also will result in decreased production of prostanoids and leukotrienes, and, therefore, will result in decreased pain and inflammation. An example of a $PLC_\gamma$ isoform inhibitor is 1-[6-((17β-3-methoxyestra-1,3,5(10)-trien-17-yl)amino)hexyl]-1H-pyrrole-2,5-dione. Suitable concentrations for this agent when delivered locally are included in Table 23. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 23

Therapeutic and Preferred Concentrations of
Pain and/or inflammation Inhibitory Agents

| Class of Agent | Local Delivery Therapeutic Concentrations (Nanomolar) | Local Delivery Preferred Concentrations (Nanomolar) |
| --- | --- | --- |
| Phospholipase Inhibitor: | | |
| Manoalide | 100–100,000 | 500–10,000 |
| aristolochic acid | 40–400,000 | 400–40,000 |
| ACA | 10–100,000 | 100–10,000 |
| HELSS | 6–6,000 | 60–6,000 |

9b. Cyclooxygenase Inhibitors

Nonsteroidal anti-inflammatory drugs (NSAIDs) are widely used as anti-inflammatory, anti-pyretic, anti-thrombotic and analgesic agents. Lewis, R. A., *Prostaglandins and Leukotrienes*, In: Textbook of Rheumatology, 3d ed. (Kelley W. N., et al., eds.), p. 258 (1989). The molecular targets for these drugs are Type I and Type II cyclooxygenases (COX-1 and COX-2). These enzymes are also known as Prostaglandin H Synthase (PGHS)-1 (constitutive) and -2 (inducible), and catalyze the conversion of arachidonic acid to Prostaglandin H that is an intermediate in the biosynthesis of prostaglandins and thromboxanes. The COX-2 enzyme has been identified in endothelial cells, macrophages, and fibroblasts. This enzyme is induced by IL-1 and TNF-α, and its expression is upregulated at sites of inflammation. Constitutive activity of COX-1 and induced activity of COX-2 both lead to synthesis of prostaglandins that contribute to pain and inflammation.

Many NSAIDs currently on the market (diclofenac, naproxen, indomethacin, ibuprofen, etc.) are generally nonselective inhibitors of both isoforms of COX, but may show greater selectively for COX-1 over COX-2, although this ratio varies for the different compounds. Use of COX-1 and 2 inhibitors to block formation of prostaglandins represents a better therapeutic strategy than attempting to block interactions of the natural ligands with the seven described subtypes of prostanoid receptors. Reported antagonists of the eicosanoid receptors (EP-1, EP-2, EP-3) are quite rare and only specific, high affinity antagonists of the thromboxane A2 receptor have been reported. Wallace, J. et al. *Trends in Pharm. Sci.*, 15:405–406 (1994).

Representative therapeutic and preferred concentrations of cyclooxygenase inhibitors for local delivery use in the solution are provided in Table 24. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 24

Therapeutic and Preferred Concentrations of
Pain and/or inflammation Inhibitory Agents

| Class of Agent | Local Delivery Therapeutic Concentrations (Nanomolar) | Local Delivery Preferred Concentrations (Nanomolar) |
| --- | --- | --- |
| Cyclooxygenase Inhibitors: | | |
| ketorolac | 100–10,000 | 500–5,000 |
| indomethacin | 1,000–500,000 | 10,000–200,000 |

9c. Lipooxygenase Inhibitors

Inhibition of the enzyme lipooxygenase inhibits the production of leukotrienes, such as leukotriene $B_4$, which is known to be an important mediator of inflammation and pain. Lewis, R. A., *Prostaglandins and Leukotrienes*, In: Textbook of Rheumatology, 3d ed. (Kelley W. N., et al., eds.), p. 258 (1989). An example of a 5-lipooxygenase antagonist is 2,3,5-trimethyl-6-(12-hydroxy-5,10-dodecadiynyl)-1,4-benzoquinone ("AA 861"), suitable local delivery concentrations for which are listed in Table 25. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 25

Therapeutic and Preferred Concentrations of
Pain and/or inflammation Inhibitory Agents

| Class of Agent | Local Delivery Therapeutic Concentrations (Nanomolar) | Local Delivery Preferred Concentrations (Nanomolar) |
| --- | --- | --- |
| Lipooxygenase Inhibitor: | | |
| AA 861 | 100–10,000 | 500–5,000 |
| Caffeic acid | 500–50,000 | 2,000–20,000 |

10. Prostanoid Receptor Antagonists

Specific prostanoids produced as metabolites of arachidonic acid mediate their inflammatory effects through activation of prostanoid receptors. Examples of classes of specific prostanoid antagonists are the eicosanoid EP-1 and EP-4 receptor subtype antagonists and the thromboxane receptor subtype antagonists. A suitable prostaglandin $E_2$ receptor antagonist is 8-chlorodibenz[b,f][1,4]oxazepine-10

(1H)-carboxylic acid, 2-acetylhydrazide ("SC 19220"). A suitable thromboxane receptor subtype antagonist is [15-[1α,2β(5Z),3β,4α]-7-[3-[2-(phenylamino)-carbonyl]hydrazino]methyl]-7-oxobicyclo-[2,2,1]-hept-2-yl]-5-heptanoic acid ("SQ 29548"). Suitable concentrations for these agents when delivered locally are set forth in Table 26. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 26

Therapeutic and Preferred Concentrations of Pain and/or inflammation Inhibitory Agents

| Class of Agent | Local Delivery Therapeutic Concentrations (Nanomolar) | Local Delivery Preferred Concentrations (Nanomolar) |
|---|---|---|
| Eicosanoid EP-1 Antagonist: | | |
| SC 19220 | 100–10,000 | 500–5,000 |

11. Leukotriene Receptor Antagonists

The leukotrienes ($LTB_4$, $LTC_4$, and $LTD_4$) are products of the 5-lipooxygenase pathway of arachidonic acid metabolism that are generated enzymatically and have important biological properties. Leukotrienes are implicated in a number of pathological conditions including inflammation. Specific antagonists are currently being sought by many pharmaceutical companies for potential therapeutic intervention in these pathologies. Halushka, P. V., et al., *Annu. Rev. Pharmacol. Toxicol.* 29:213–239 (1989); Ford-Hutchinson, A., *Crit. Rev. Immunol.* 10:1–12 (1990). The $LTB_4$ receptor is found in certain immune cells including eosinophils and neutrophils. $LTB_4$ binding to these receptors results in chemotaxis and lysosomal enzyme release thereby contributing to the process of inflammation. The signal transduction process associated with activation of the $LTB_4$ receptor involves G-protein-mediated stimulation of phosphotidylinositol (PI) metabolism and elevation of intracellular calcium (see FIG. 2).

An example of a suitable leukotriene $B_4$ receptor antagonist is SC (+)-(S)-7-(3-(2-(cyclopropylmethyl)-3-methoxy-4-[(methylamino)-carbonyl]phenoxy(propoxy)-3,4-dihydro-8-propyl-2H-1-benzopyran-2-propanoic acid ("SC 53228"). Other suitable leukotriene $B_4$ receptor antagonists include [3-[-2(7-chloro-2-quinolinyl)ethenyl]phenyl][[3-(dimethylamino-3-oxopropyl)thio]methyl]thiopropanoic acid ("MK 0571") and the drugs LY 66,071 and ICI 20,3219. MK 0571 also acts as a $LTD_4$ receptor subtype antagonist. Concentrations for this agent that are suitable for the practice of local delivery methods of the present invention are provided in Table 27. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 27

Therapeutic and Preferred Concentrations of Pain and/or inflammation Inhibitory Agents

| Class of Agent | Local Delivery Therapeutic Concentrations (Nanomolar) | Local Delivery Preferred Concentrations (Nanomolar) |
|---|---|---|
| Leukotriene $B_4$ Antagonist: | | |
| SC 53228 | 100–10,000 | 500–5,000 |

12. Opioid Receptor Agonists

Activation of opioid receptors results in anti-nociceptive effects and, therefore, agonists to these receptors are desirable. Opioid receptors include the μ-, δ- and κ-opioid receptor subtypes. The μ-receptors are located on sensory neuron terminals in the periphery and activation of these receptors inhibits sensory neuron activity. Basbaum, A. I., et al., "Opiate analgesia: How Central is a Peripheral Target?", *N. Engl. J. Med.* 325:1168 (1991). δ- and κ-receptors are located on sympathetic efferent terminals and inhibit the release of prostaglandins, thereby inhibiting pain and inflammation. Taiwo, Y. O., et al., "Kappa- and Delta-Opioids Block Sympathetically Dependent Hyperalgesia", *J. Neurosci.* 11:928 (1991). The opioid receptor subtypes are members of the G-protein coupled receptor superfamily. Therefore, all opioid receptor agonists interact and initiate signaling through their cognate G-protein coupled receptor. Examples of suitable μ-opioid receptor agonists are fentanyl and Try-D-Ala-Gly-[N-MePhe]-NH($CH_2$)-OH ("DAMGO"). An example of a suitable δ-opioid receptor agonist is [D-$Pen^2$,D-$Pen^5$]enkephalin ("DPDPE"). An example of a suitable κ-opioid receptor agonist is (trans)-3,4-dichloro-N-methyl-N-[2-(1-pyrrolidnyl)cyclohexyl]-benzene acetamide ("U50,488"). Suitable concentrations for the local delivery of each of these agents are set forth in Table 28. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 28

Therapeutic and Preferred Concentrations of Pain and/or inflammation Inhibitory Agents

| Class of Agent | Local Delivery Therapeutic Concentrations (Nanomolar) | Local Delivery Preferred Concentrations (Nanomolar) |
|---|---|---|
| μ-Opioid Agonist: | | |
| DAMGO | 0.1–100 | 0.5–20 |
| sufentanyl | 0.01–50 | 1–20 |
| fentanyl | 0.1–500 | 10–200 |
| PL 017 | 0.05–50 | 0.25–10 |
| δ-Opioid Agonist: | | |
| DPDPE | 0.1–500 | 1.0–100 |
| κ-Opioid Agonist: | | |
| U50,488 | 0.1–500 | 1.0–100 |

13. Purinoceptor Antagonists

Extracellular ATP acts as a signaling molecule through interactions with $P_2$ purinoceptors. One major class of purinoceptors are the $P_{2X}$ purinoceptors which are ligand-gated ion channels possessing intrinsic ion channels permeable to $Na^+$, $K^+$, and $Ca^{2+}$. $P_{2X}$ receptors described in sensory neurons are important for primary afferent neurotransmission and nociception. ATP is known to depolarize sensory neurons and plays a role in nociceptor activation since ATP released from damaged cells stimulates $P_{2X}$ receptors leading to depolarization of nociceptive nerve-fiber terminals. The $P2X_3$ receptor has a highly restricted distribution (Chen, C. C., et al., Nature, Vol. 377, pp. 428–431 (1995)) since it is selectively expressed in sensory C-fiber nerves that run into the spinal cord and many of these C-fibers are known to carry the receptors for painful stimuli. Thus, the highly restricted localization of expression for the $P2X_3$ receptor subunits make these subtypes excellent targets for analgesic action (see FIGS. 3 and 7).

Calcium-mobilizing purine receptors, which belong to the G-protein receptor superfamily, have been described on the surface of mammalian articular chondrocytes. ATP was found to stimulate a dose-dependent, transient rise in the concentration of calcium ions in differentiated, primary chondrocytes. Heterologous desensitization experiments demonstrated that chondrocytes showed no subsequent response to UTP after initial stimulation with ATP. These results are consistent with the presence of a P2Y receptors of the cell surface of chondrocytes. Purine-induced calcium mobilization in passaged chondrocytes showed the same pharmacological profile with respect to agonist sensitivity. ATP and UTP did not alter cartilage matrix synthesis as measured by rate of incorporation of [35S]sulfate into glycosaminoglycan by cartilage explants or primary chondrocytes. Matrix degradation, measured by release of glycosaminoglycan from cartilage explants, was also unaltered by either agonist. The presence of a functional P2Y purine receptor on the surface of primary articular chondrocytes enable concentrations of extracellular purines, such as ATP, to activate chondrocyte metabolism.

Other studies have defined the expression of both P1 and P2 purine receptor genes by human articular chondrocytes and profiled ligand-mediated prostaglandin E2 release. The P2Y2 receptor agonists ATP and UTP stimulated a small release of PGE2 that was synergistically enhanced after pretreatment with human IL-1α. PGE2 release in response to coaddition of ATP and UTP after IL-1 pretreatment was mimicked by phorbol myristate acetate. The function of the P2Y2 receptor is to increase IL-1-mediated PGE2 release, thereby promoting pain and inflammation within the joint. Thus, the use of P2Y antagonists in the present invention should prevent activation of inflammatory mediator production by both synoviocytes and chondrocytes.

Suitable antagonists of $P_{2X}$/ATP purinoceptors for use in the present invention include, by way of example, suramin and pyridoxylphosphate-6-azophenyl-2,4-disulfonic acid ("PPADS"). Suitable concentrations for the local delivery of these agents are provided in Table 29. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 29

Therapeutic and Preferred Concentrations of Pain and/or inflammation Inhibitory Agents

| Class of Agent | Local Delivery Therapeutic Concentrations (Nanomolar) | Local Delivery Preferred Concentrations (Nanomolar) |
| --- | --- | --- |
| P2X and/or P2Y Antagonists: | | |
| Suramin | 100–100,000 | 10,000–100,000 |
| PPADS | 100–100,000 | 10,000–100,000 |

14. $Ca^{2+}$ Channel Antagonists

Calcium channel antagonists are a distinct group of drugs that interfere with the transmembrane flux of calcium ions required for activation of cellular responses mediating neuroinflammation. Calcium entry into synoviocytes and chondrocytes is a key event mediating activation of responses in these cells. Furthermore, the role of bradykinin, histamine, serotonin ($SHT_2$) and neurokinin receptors ($NK_1$ and $NK_2$) in mediating the neuroinflammation signal transduction pathway includes increases in intracellular calcium, thus leading to activation of calcium channels on the plasma membrane. In many tissues, calcium channel antagonists, such as nifedipine, can reduce the release of arachidonic acid, prostaglandins, and leukotrienes that are evoked by various stimuli. Moncada, S. et al., *Goodman's and Gilman's Pharmacological Basis of Therapeutics*, (7th ed.), MacMillan Publ. Inc., 660–5 (1995).

Finally, calcium channel antagonists and either tachykinin, histamine or bradykinin antagonists exhibit synergistic effects in inhibiting neuroinflammation.

The role of neurokinin receptors in mediating neuroinflammation has been established. The neurokinin$_1$ ($NK_1$) and neurokinin$_2$ ($NK_2$) receptor (members of the G-protein coupled superfamily) signal transduction pathway includes increases in intracellular calcium, thus leading to activation of calcium channels on the plasma membrane. Similarly, activation of bradykinin$_2$ ($BK_2$) receptors is coupled to increases in intracellular calcium in synoviocytes and chondrocytes. Thus, calcium channel antagonists interfere with a common mechanism involving elevation of intracellular calcium, part of which enters through L-type channels. This is the basis for synergistic interaction between calcium channel antagonists and antagonists to neurokinin, histamine, $P_2Y$ and bradykinin$_2$ receptors.

Suitable calcium channel antagonists for the practice of the present invention include nisoldipine, nifedipine, nimodipine, lacidipine, isradipine and amlodipine. Suitable concentrations for the local delivery of these agents are set forth in Table 30. Similarly, systemic compositions in accordance with the present invention will suitably include a dosage or load of the agent sufficient to result in a local concentration at the joint or site of action within the listed therapeutic range. For targeted sustained release delivery systems, a sufficient dosage or load of the agent is included in the composition to result in a local concentration at the joint or site of action within the listed therapeutic range over a predetermined sustained release period.

TABLE 30

Therapeutic and Preferred Concentrations of Spasm Inhibitory Agents

| Class of Agent | Local Delivery Therapeutic Concentrations (Nanomolar) | Local Delivery Preferred Concentrations (Nanomolar) |
| --- | --- | --- |
| Calcium Channel Antagonists: | | |
| Nisoldipine | 1–10,000 | 100–1,000 |
| Nifedipine | 1–10,000 | 100–5,000 |
| Nimodipine | 1–10,000 | 100–5,000 |
| Lacidipine | 1–10,000 | 100–5,000 |
| Isradipine | 1–10,000 | 100–5,000 |
| Amlodipine | 1–10,000 | 100–5,000 |

VI. EXAMPLES

The following are several formulations in accordance with the aspects of the present invention suitable for irrigation in certain operative procedures (Examples 1–3), and for systemic delivery, such as by intramuscular or subcutaneous injection (Examples 4–11) and are followed by a summary of three clinical studies utilizing the agents of the present invention.

Example 1

Irrigation Solution for Arthroscopy

The following composition is suitable for use in anatomic joint irrigation during arthroscopic procedures. Each drug is solubilized in a carrier fluid containing physiologic electrolytes, such as normal saline or lactated Ringer's solution, as are the remaining solutions described in subsequent examples.

| Class of Agent | Drug | Concentration (Nanomolar) |
| --- | --- | --- |
| MAP Kinase Inhibitor | SB203580 | 200 |
| Matrix Metalloproteinase Inhibitor | U-24522 | 200 |
| TGF-β Agonist | TGF-β2 | 200 |

Example 2

Alternative Irrigation Solution for Arthroscopy

The following composition is an alternate formulation suitable for use in anatomic joint irrigation during arthroscopic procedures.

| Class of Agent | Drug | Concentration (Nanomolar) |
| --- | --- | --- |
| MAP Kinase Inhibitor | SB203580 | 200 |
| Nitric Oxide Synthase Inhibitor | L-NIL | 1,000 |
| Interleukin Receptor Agonist | IL-10 | 100 |

Example 3

Alternate Irrigation Solution

The following drugs and concentration ranges in solution in a physiologic carrier fluid are suitable for use in the present invention.

| Class of Agent | Drug | Concentration (Nanomolar) |
| --- | --- | --- |
| MAP Kinase Inhibitor | SB242235 | 200 |
| Nitric Oxide Synthase Inhibitor | L-NIL | 10,000 |
| TGF-β Agonist | TGF-β2 | 100 |

Example 4

Chondroprotective Solution for Injection

The following composition is suitable for injection into an anatomic joint. Each drug is solubilized in a carrier fluid containing physiologic electrolytes, such as normal saline or lactated Ringer's solution. A dosage of 20 ml of the solution is suitable for administration to a patient.

| Class of Agent | Drug | Concentration |
| --- | --- | --- |
| BMP Receptor Agonist | BMP-7 | 100 ng/ml |
| Nitric Oxide Synthase Inhibitor | 1,3 PBIT | 4.4 µg/ml |
| NFκB Agonist | pyrrolidine-dithiocarbamate | 16.4 µg/ml |

Example 5

Chondroprotective Composition for Systemic Delivery

The following chondroprotective composition is suitable for systemic delivery, such as by intramuscular or subcutaneous administration. Each drug is included in the composition at a concentration that will result in the following concentration at the site of intended action, and is solubilized in a physiologic carrier fluid or delivery system.

| Class of Agent | Drug | Concentration at Site of Action (Nanomolar) |
| --- | --- | --- |
| MAP Kinase Inhibitor | SB203580 | 200 |
| Matrix Metalloproteinase Inhibitor | U-24522 | 200 |
| TGF-β Agonist | TGF-β2 | 200 |

Example 6

Alternate Chondroprotective Composition for Systemic Delivery

The following chondroprotective composition is suitable for systemic delivery, such as by intramuscular or subcutaneous administration. Each drug is included in the composition at a concentration sufficient to result in the following concentration at the site of intended action, and is solubilized in a physiologic carrier fluid or delivery system.

| Class of Agent | Drug | Concentration at Site of Action (Nanomolar) |
|---|---|---|
| MAP Kinase Inhibitor | SB203580 | 200 |
| Nitric Oxide Synthase Inhibitor | L-NIL | 1,000 |
| Interleukin Receptor Agonist | IL-10 | 100 |

Example 7

Alternate Chondroprotective Composition for Systemic Delivery

The following chondroprotective composition is suitable for systemic delivery, such as by intramuscular or subcutaneous administration. Each drug is included in the composition at a concentration sufficient to result in the following concentration at the site of intended action, and is solubilized in a physiologic carrier fluid or delivery system.

| Class of Agent | Drug | Concentration at Site of Action (Nanomolar) |
|---|---|---|
| MAP Kinase Inhibitor | SB242235 | 200 |
| Nitric Oxide Synthase Inhibitor | L-NIL | 10,000 |
| TGF-β Agonist | TGF-β2 | 100 |

Example 8

Alternate Chondroprotective Composition for Systemic Delivery

The following chondroprotective composition is suitable for systemic delivery, such as by intramuscular or subcutaneous administration. Each drug is included in the composition at a concentration sufficient to result in the following concentration at the site of intended action, and is solubilized in a physiologic carrier fluid or delivery system.

| Class of Agent | Drug | Concentration at Site of Action (Nanomolar) |
|---|---|---|
| Soluble TNF-α Receptor (sTNFRII:Fc) | Etanercept (Enbrel ™, Immunex) | 250 |
| MAP Kinase Inhibitor | SB203580 | 500 |
| TGF-β Agonist | TGF-β2 | 200 |

Example 9

Alternate Chondroprotective Composition for Systemic Delivery

The following chondroprotective composition is suitable for systemic delivery, such as by intramuscular or subcutaneous administration. Each drug is included in the composition at a concentration sufficient to result in the following concentration at the site of intended action, and is solubilized in a physiologic carrier fluid or delivery system.

| Class of Agent | Drug | Concentration at Site of Action (Nanomolar) |
|---|---|---|
| IL-1 Receptor Antagonist (IL-1Ra) | Anakinra (Kineret ™, Amgen) | 250 |
| MAP Kinase Inhibitor | SB203580 | 500 |
| TGF-β Agonist | TGF-β2 | 200 |

Example 10

Alternate Chondroprotective Composition for Systemic Delivery

The following chondroprotective composition is suitable for systemic delivery, such as by intramuscular or subcutaneous administration. Each drug is included in the composition at a concentration sufficient to result in the following concentration at the site of intended action, and is solubilized in a physiologic carrier fluid or delivery system.

| Class of Agent | Drug | Concentration at Site of Action (Nanomolar) |
|---|---|---|
| MAP Kinase Inhibitor | SB203580 | 500 |
| IGF-1 | IGF-1 | 250 |
| BMP Agonist | BMP-2 | 200 |

Example 11

Alternate Chondroprotective Composition for Systemic Delivery

The following chondroprotective composition is suitable for systemic delivery, such as by intramuscular or subcutaneous administration. Each drug is administered at the noted dosage, and is solubilized in a physiologic carrier fluid or delivery system.

| Class of Agent | Drug | Dosage (mg/kg/day) |
|---|---|---|
| Soluble TNF-α Receptor (sTNFRII:Fc) | Etanercept (Enbrel ™, Immunex) | 0.5–1.0 |
| MAP Kinase Inhibitor | SB203580 | 30–60 |
| TGF-β Agonist | TGF-β2 | 0.1–10 |

Example 12

Alternate Chondroprotective Composition for Systemic Delivery

The following chondroprotective composition is suitable for systemic delivery, such as by intramuscular or subcutaneous administration. Each drug is administered at the noted dosage, and is solubilized in a physiologic carrier fluid or delivery system.

| Class of Agent | Drug | Dosage (mg/kg/day) |
| --- | --- | --- |
| IL-1 Receptor Antagonist (IL-1Ra) | Anakinra (Kineret ™, Amgen) | 2.0 |
| MAP Kinase Inhibitor | SB203580 | 30–60 |
| TGF-β Agonist | TGF-β2 | 0.1–10 |

Example 13

Targeted Chondroprotective Drug Delivery System

The following chondroprotective composition is suitable for systemic delivery, such as by intravenous, intramuscular, subcutaneous or inhalation administration. The drugs are encapsulated within a DL-lactide/glycolide copolymer (PLGA) nanosphere, to which is coupled an anti-human Type II collagen monoclonal antibody. This antibody targets epitopes on human Type II collagen in articular cartilage. Each drug is included in the composition at a concentration sufficient to result in the following average concentration at the site of intended action upon degradation of the nanosphere and release of the agents over a period of sustained release.

| Class of Agent | Drug | Concentration at Site of Action (Nanomolar) |
| --- | --- | --- |
| Growth Factor | IGF-1 | 250 nM |
| MAP Kinase inhibitor | SB220025 | 1000 nM |
| MMP inhibitor | BB2516 (marimastat) | 200 nM |

Example 14

Targeted Chondroprotective Drug Delivery System

The following chondroprotective composition is suitable for systemic delivery, such as by intravenous, intramuscular, subcutaneous or inhalation administration. The drugs are encapsulated within a biodegradable PLA/PLGA co-polymeric nanosphere, to which is coupled an anti-human aggrecan monoclonal antibody. This antibody targets neoepitopes on human aggrecan in articular cartilage. Each drug is included in the composition at a concentration sufficient to result in the following concentration at the site of intended action upon degradation of the nanosphere and release of the agents over a desired period of sustained release.

| Class of Agent | Drug | Concentration at Site of Action (Nanomolar) |
| --- | --- | --- |
| Growth Factor | IGF-1 | 250 nM |
| MAP Kinase inhibitor | SB220025 | 1000 nM |
| MMP inhibitor | BB2516 (marimastat) | 200 nM |

Example 15

Targeted Chondroprotective Drug Delivery System

The following chondroprotective composition is suitable for systemic delivery, such as by intravenous, intramuscular, subcutaneous or inhalation administration. The drugs are encapsulated within a chitosan/gelatin nanosphere, to which is coupled an anti-human Type II collagen monoclonal antibody. This antibody targets neoepitopes on human Type II collagen. Each drug is included in the composition at a concentration sufficient to result in the following concentration at the site of intended action upon degradation of the nanosphere and release of the agents over a desired period of sustained release.

| Class of Agent | Drug | Concentration at Site of Action (Nanomolar) |
| --- | --- | --- |
| BMP Receptor agonist | BMP-7 | 200 |
| MAP Kinase Inhibitor | SB203580 | 500 |

Example 16

Targeted Chondroprotective Drug Delivery System

The following chondroprotective composition is suitable for systemic delivery, such as by intravenous, intramuscular, subcutaneous or inhalation administration. The drugs are encapsulated within an albumin nanosphere, to which is coupled an anti-human Type II collagen monoclonal antibody. This antibody targets neoepitopes on human Type II collagen. Each drug is included in the composition at a concentration sufficient to result in the following concentration at the site of intended action upon degradation of the nanosphere and release of the agents over a desired period of sustained release.

| Class of Agent | Drug | Concentration at Site of Action (Nanomolar) |
| --- | --- | --- |
| BMP Receptor agonist | BMP-7 | 200 |
| MMP inhibitor | BB2516 | 200 |

Example 17

Targeted Chondroprotective Drug Delivery System

The following chondroprotective composition is suitable for systemic delivery, such as by intravenous, intramuscular, subcutaneous or inhalation administration. The drugs are encapsulated within a poly(lactide-co-glycolide)/poly(ethyleneglycol) copolymer nanosphere, to which is coupled an anti-human Type II collagen monoclonal antibody. This antibody targets neoepitopes on human Type II collagen in articular cartilage. Each drug is included in the composition at a concentration sufficient to result in the following concentration at the site of intended action upon degradation of the nanosphere and release of the agents over a desired period of sustained release.

| Class of Agent | Drug | Concentration at Site of Action (Nanomolar) |
|---|---|---|
| BMP Receptor agonist | BMP-7 | 200 |
| MAP Kinase Inhibitor | SB203580 | 500 |

Example 18

Targeted Chondroprotective Drug Delivery System

The following chondroprotective composition is suitable for systemic delivery, such as by intravenous, intramuscular, subcutaneous or inhalation administration. The BMP receptor agonist, BMP-7 is encapsulated within a poly(lactide-co-glycolide) (PLGA) nanosphere to which is coupled an anti-human Type II collagen monoclonal antibody. The IGF Receptor agonist, IGF-1 is separately encapsulated within a chondroiten-6-sulfate/gelatin nanosphere to which is also coupled an anti-human aggrecan monoclonal antibody. The antibody used for targeting each type of nanosphere binds to neoeptitopes on human Type II collagen and neoepitopes on aggrecan in articular cartilage. Each drug is included in the composition at a concentration sufficient to result in the following average concentration at the site of intended action upon degradation of the nanosphere and release of the agents over a desired period of sustained release.

| Class of Agent | Drug | Concentration at Site of Action (Nanomolar) |
|---|---|---|
| BMP Receptor agonist | BMP-7 | 200 |
| IGF-Receptor agonist | IGF-1 | 500 |

Example 19

Targeted Chondroprotective Drug Delivery System

The following chondroprotective composition is suitable for systemic delivery, such as by intravenous, intramuscular, subcutaneous or inhalation administration. The drugs are encapsulated within an albumin nanosphere, to which is coupled an anti-human F(ab')$_2$ fragment that binds to Type II collagen monoclonal antibody. This F(ab')$_2$ antibody targets neoeptitopes on human Type II collagen. Each drug is included in the composition at a concentration sufficient to result in the following concentration at the site of intended action upon degradation of the nanosphere and release of the agents over a desired period of sustained release.

| Class of Agent | Drug | Concentration at Site of Action (Nanomolar) |
|---|---|---|
| BMP Receptor agonist | BMP-7 | 200 |
| MMP inhibitor | BB2516 | 200 |

Example 20

Targeted Chondroprotective Drug Delivery System

The following chondroprotective composition is suitable for systemic delivery, such as by intravenous, intramuscular, subcutaneous or inhalation administration. The drugs are encapsulated within an albumin nanosphere, to which is coupled an anti-human single-chain minimum binding domain of an immunoglobulin molecule (scFV) that binds to Type II collagen monoclonal antibody. This scFV antibody targets neoeptitopes on human Type II collagen. Each drug is included in the composition at a concentration sufficient to result in the following concentration at the site of intended action upon degradation of the nanosphere and release of the agents over a desired period of sustained release.

| Class of Agent | Drug | Concentration at Site of Action (Nanomolar) |
|---|---|---|
| BMP Receptor agonist | BMP-7 | 200 |
| MMP inhibitor | BB2516 | 200 |

Study 1

Synergistic Stimulation of a Rapid PGE2 Burst upon Exposure to IL-1 and GPCR Agonists Fibroblast-like synoviocytes exhibit characteristics of inflammatory cells and seem to be crucial regulators of joint inflammation and cartilage degradation. A synoviocyte cell culture model system was used to characterize the synergistic interactions between IL-1 and non-cytokine inflammatory mediators which are important in modulating the destruction of joint tissue, including damage that occurs as a consequence of tissue injury during arthroscopic surgery. Experiments were conducted to investigate G-protein coupled receptor (GPCR) agonists (histamine, bradykinin and isoproteronol) on the regulation of cytokine and prostanoid production in cultured human synovial fibroblasts and to characterize the activities of ketoprofen in this system. The kinetics of induction of prostaglandin E2 (PGE$_2$), interleukin-6 (IL-6) and interleukin-8 (IL-8) in response to stimulation with interleukin-1 (IL-1) are described. The ability of GPCR ligands to potentiate cytokine production following IL-1 priming was investigated.

In Studies 1–3, the following experimental methods and materials were employed unless otherwise indicated.

1. Cell Culture. Synovial tissue was obtained from osteoarthritis patients undergoing joint replacement surgery through the Clinical Research Center, MacNeal Hospital, and transported to the laboratory in Dulbecco's Modified Eagle's Medium (DMEM) containing penicillin (100 units/ml), streptomycin (100 μg/ml), and fungizone (0.25 μg/ml). The synovium was dissected and minced with scissors, and plated as explants in culture medium composed of DMEM containing L-glutamine (2 mM), heat inactivated fetal bovine serum (10% v/v), plus antibiotics. Cultures were housed at 37° C. in a humidified atmosphere of 5% CO$_2$. Adherent synovial cells grew out of the explants within 2–3 weeks, and were passaged by trypsinization. Seed cultures were fed twice weekly and were passaged at confluency. Experiments were performed on cells from passages 3–8.

Experimental cultures were plated into 35 mm dishes at a density of $7.5\times10^3$ cells/cm$^2$ in 2 ml culture medium. Cultures were grown to near confluency for experiments, and contained $2.3\pm0.3\times10^5$ cells (mean±S.E.M., n=3), and $104\pm13$ μg protein (n=10). The growth medium was replaced twice weekly.

2. Experimental Treatments. One day prior to initiation of experimental treatments, medium was changed to experimental growth medium composed of DMEM containing 2% heat-inactivated fetal bovine serum, plus L-glutamine and antibiotics as above, to render the cells quiescent. The next day, cultures were primed by addition of specified concentrations of IL-0.1 or additional ligands to the conditioned growth medium for 12–24 hr intervals, as indicated. In some experiments, conditioned growth medium was collected for analysis following priming with IL-1. Acute experimental treatments were performed after this priming interval, as follows. Cultures were removed from the incubator, washed three times with 2 ml aliquots of Locke's physiological buffer (LB composition in mM: NaCl, 154; KCl, 2.6; KH$_2$PO$_4$, 2.15; K$_2$HPO$_4$, 0.85; MgCl$_2$, 5; CaCl$_2$, 2; D-glucose, 10; HEPES, 10; pH 7.4, BSA, 0.1% w/v), and then equilibrated with an additional aliquot of LB containing specified ligands for 10 min on a 37° bath. This solution was removed by aspiration and replaced with a fresh buffer aliquot containing indicated ligands for specified time intervals at 37°. Pharmacological inhibitors typically were added during the 10 min preincubation interval, and agonists plus the specified inhibitors were present during the 3 min challenge interval.

3. Measurement of Prostaglandin E2. Following indicated treatment protocols, aliquots of culture supernatant (1 ml) were collected and rapidly frozen in liquid nitrogen. Samples were stored at –80° until processing. Aliquots of culture supernatant were analyzed by competitive binding radioimmunoassay as specified by the manufacturer (Sigma Chemical Co.), using an antibody with equivalent reactivity toward prostaglandins E2 and E1. For quantitation, a standard curve was prepared with each assay using fixed concentrations of [$^3$H]prostaglandin E2, and increasing concentrations of authentic competing prostaglandin E2.

4. Measurement of IL-6. Production of the cytokine, IL-6, was also measured in aliquots of supernatant culture media which had been stored frozen at –80° C. IL-6 was measured by sandwich ELISA with alkaline phosphatase detection as described by the manufacturer (Pharmingen) and quantitated using standard curves prepared with the respective pure recombinant human cytokines. Experimental determinations were performed on duplicate cultures.

Study 2

Assays for [$^3$H]thymidine Incorporation and MTT

Synoviocyte cell lines were routinely evaluated for competence to proliferate in response to IL-1, measured as incorporation of [$^3$H]thymidine (Kimball & Fisher, 1988). In this preparation, maximally effective concentrations of IL-1 stimulate [$^3$H]thymidine incorporation by 10–20 fold compared to quiescent cultures maintained in 2% serum (data not shown).

1. Data analysis. Immunoassays were routinely performed in duplicate aliquots from each culture. Experimental determinations were performed on duplicate or triplicate cultures. Each experiment was repeated in at least two cell lines. Nonlinear regression curve fitting and statistical analyses were performed using Graph-PAD Prism software (San Diego, Calif.).

2. Materials. Cell culture: Cell culture media were obtained from Sigma or Gibco/BRL. Fetal bovine serum was from Atlanta Biologicals Inc. (Norcross, Ga.). Drugs: Recombinant human interleukin-1 was obtained from Genzyme (Cambridge, Mass.). Ketoprofen was provided by Omeros Medical Systems, Inc. (Seattle, Wash.). Amitriptyline, forskolin, 5-hydroxytryptamine, isoproterenol, Bradykinin, histamine, and prostaglandin E2 were from Sigma. Radiochemicals: [$^3$H]Prostaglandin E2, was obtained from American Radiolabeled Chemicals, Inc. (St. Louis, Mo.). All other reagents were obtained in the highest purity available from standard commercial suppliers.

Figure 7:
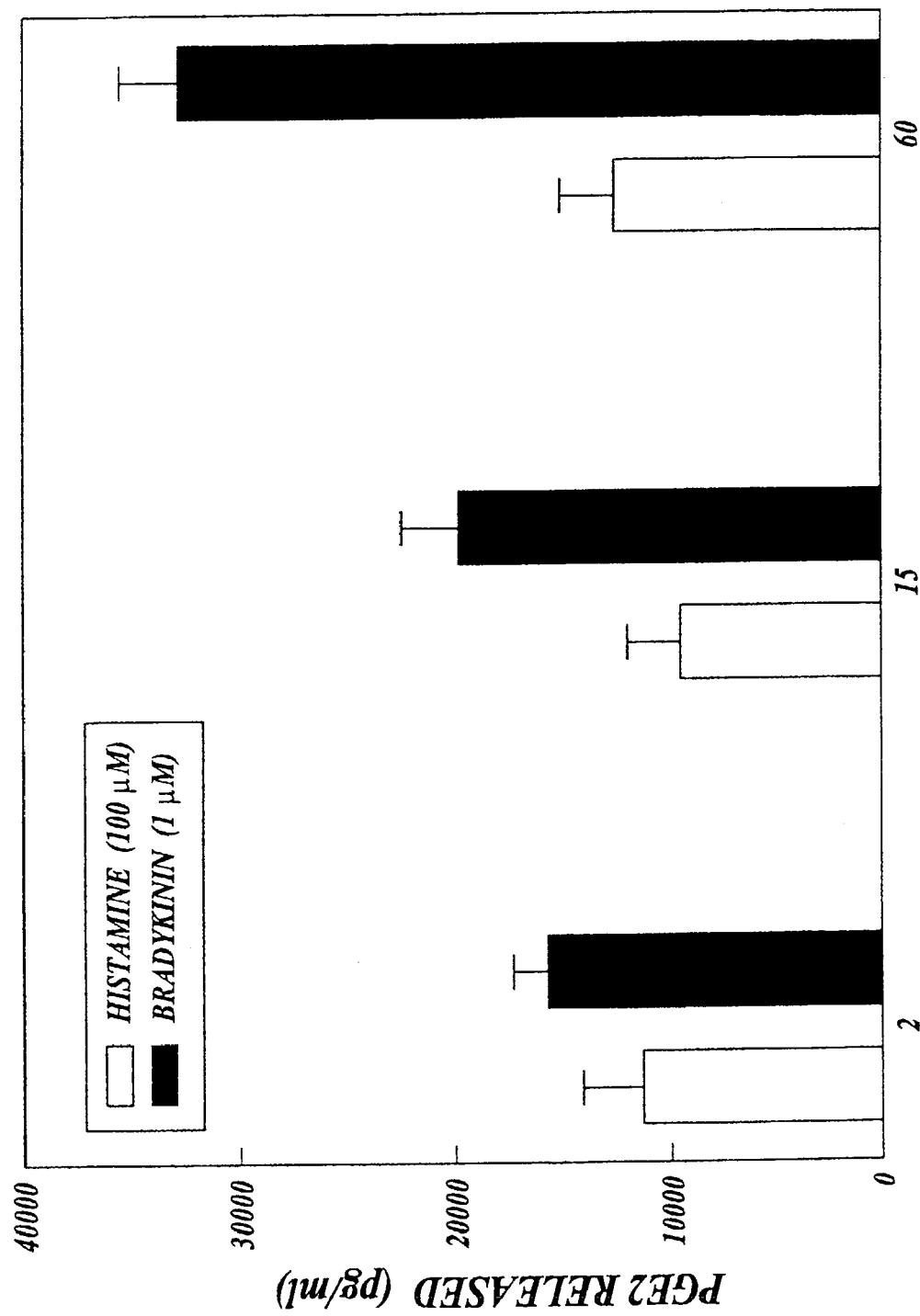
FIG. 7 is a graphical representation of the production of prostaglandin E2 in synovial cultures by G-protein regulatory agonists following overnight priming with interleukin-1 (IL-1, 10 U/ml). The cultures were stimulated for the indicated times with histamine (100 µM, open bars), or bradykinin (1 µM, closed bars), and the prostaglandin E2 released to the culture supernatant was determined as described in Study 1 herein below. The values shown are the mean±the standard deviation from a representative experiment, and are corrected for basal prostaglandin E2 production by unstimulated cultures.

The effect of GPCR agonists, histamine and bradykinin, on PGE2 production in human synovial cells was measured with and without prior stimulation to IL-1 to assess the functional interactions between agonists mediating a common pharmacological effect through these different classes of receptors. Overnight exposure of cultured human synovial fibroblasts to IL-1 (10 U/ml) results in a delayed (4 hrs) and sustained large enhancement of PGE2 production, which can be measured by radioimmunoassay as increased PGE2 in the culture supernatant. The progressive increase in PGE2 production during prolonged IL-1 treatment (16–24 hr) has been shown to arise from the coordinated upregulated expression of cPLA2 and the COX-2 (Crofford, 1984, Hulkower et al., 1984). Cultures that have been primed by overnight exposure to IL-1 respond to subsequent challenges with maximally effective concentrations of histamine (100 μM) or bradykinin (1 μM) with additional rapid (minutes) and robust production of PGE2. Representative data for the time course of PGE2 production in response to histamine or bradykinin stimulation are shown in FIG. 7. Under these conditions, histamine elicits a 5–10 fold increase in PGE2 production compared to IL-1 primed cells receiving no GPCR agonist addition. Bradykinin elicits a 10–15 fold increase. The absolute quantity of PGE2 produced during the brief 2 min agonist challenge approaches or exceed quantities that are cumulatively produced during the entire 18 hr IL-1 priming interval. This is remarkable insofar as FIG. 7 shows that the vast majority of the histamine-elicited burst in PGE2 production occurs within the initial 2 min period since minimal additional accumulation is observed over the subsequent 60 min period. The bradykinin-stimulated PGE2 response continues to increase (2-fold) over the same time period. In the absence of IL-1 priming, naive synoviocytes show no detectable PGE2 production in response to stimulation with either GPCR agonist alone. Under conditions of IL-1 priming, histamine and bradykinin both synergistically potentiated PGE2 release.

Using cultured synovial fibroblasts from osteoarthritis patients, we found time-dependent synergistic interactions between the pro-inflammatory cytokine, IL-1, and physiologically relevant G-protein coupled receptors on PGE2 production, and evaluated the actions of target therapeutic agents. GPCR agonists acting through endogenous synoviocyte receptors that are coupled to increases in intracellular calcium, inositol phosphates and PKC signaling pathways rapidly and dramatically amplify PGE2 production in cells previously primed by IL-1. COX inhibitors effectively attenuated both the agonist-elicited rapid burst and the long-term accumulation of PGE2. Thus, different GPCR and IL-1 pathways for intracellular signal transduction synergistically interact to bring about either rapid or slower, long-term regulation of PGE2 responses.

The synergism between IL-1 and calcium-regulatory GPCRs in synoviocytes that produce the rapid PGE2 burst may in part be explained by the rapid augmentation of arachidonic acid release, a measure of cPLA2 activation in many cell types. In addition to inducing COX-2 expression, IL-1 increases expression of cPLA2 (Hulkower et al., 1994). These two proteins act together to provide free arachidonic acid substrate for COX-2. The upregulation of the key eicosonoid metabolizing enzymes induced by IL-1, combined with the ability of the GPCR ligands to activate arachidonate release, would therefore be predicted to increase overall substrate flux through prostanoid synthesis. cPLA2 is the only known PLA2 that exhibits functional properties indicative of receptor regulation and is likely to be involved in eicosonoid production and intracellular signaling. Since cPLA2 is activated by increasing calcium concentrations for full activity and bradykinin B2 and histamine H1 receptor activation is coupled to mobilization of intracellular calcium, this is likely the predominant factor regulating the rapid agonist-stimulated burst in PGE2 production. Finally, the very rapid and transient increase in cytoplasmic calcium triggered by B2 or H1 receptor activation is similar to the kinetics known for cPLA2 activation, arachidonic acid release, and the observed PGE2 burst.

Study 3

Inhibition of PGE2 Burst Formation by Cyclooxygenase Inhibitors

Figure 8:
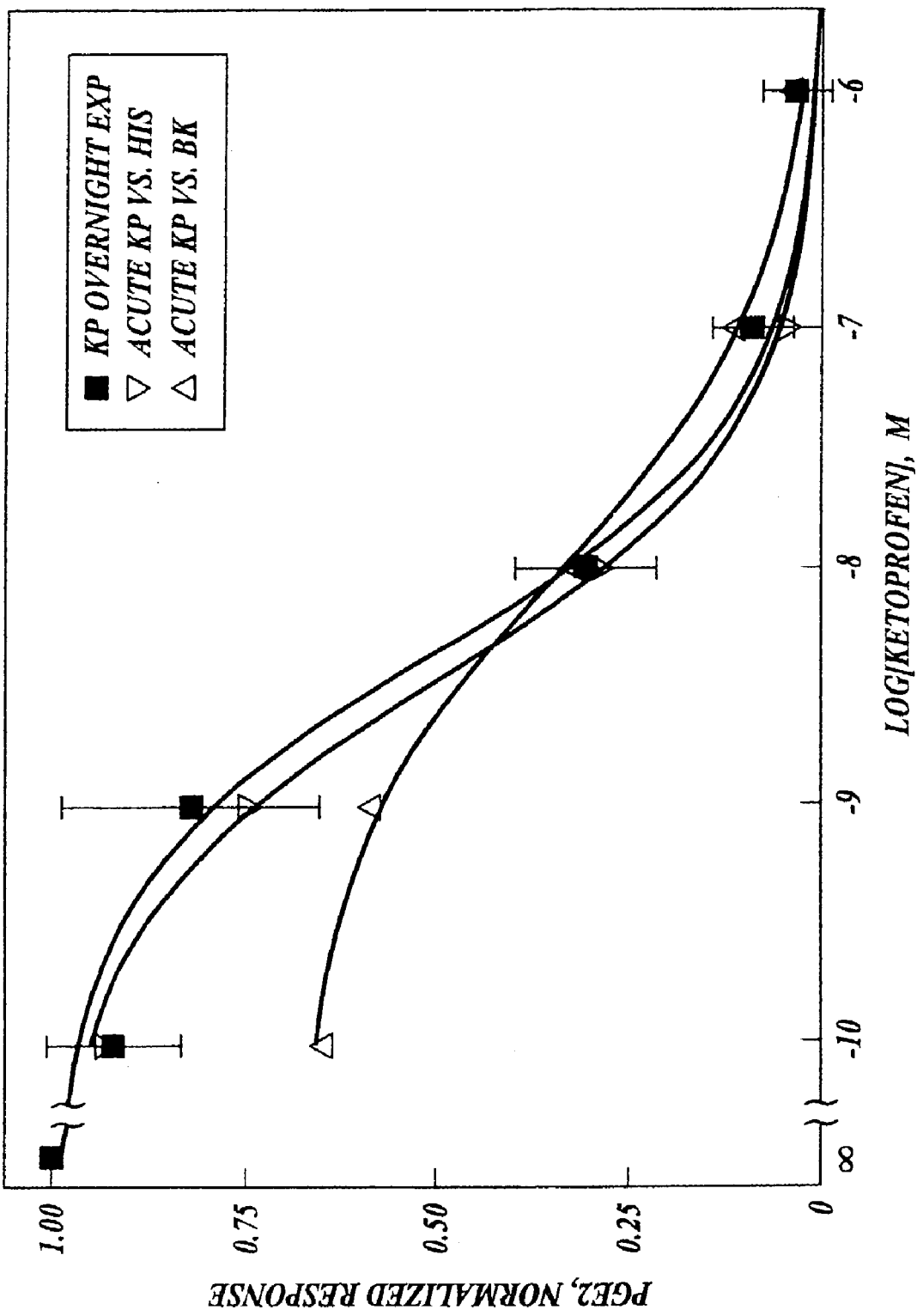
FIG. 8 is a graphical representation of the inhibition of prostaglandin E2 production in synovial cultures by ketoprofen. The cultures were primed overnight with IL-1 (10 U/ml) in the presence (shown as "■") or absence (shown as "Δ" or "∇") of the indicated concentrations of ketoprofen. After one day, prostaglandin E2 was measured in the supernatants of cultures treated overnight with ketoprofen, and the remaining cultures were washed, incubated for 10 minutes with the indicated concentrations of ketoprofen, and then prostaglandin E2 production was measured in response to a subsequent 3 minute challenge with histamine (100 µM, ∇) or bradykinin (1 µM, Δ) in the continuing presence of the indicated amounts of ketoprofen. The data shown are normalized to the maximum response obtained for each agonist, respectively, and represent the mean±the standard deviation from three experiments performed on different cell lines.

The actions of ketoprofen, a cyclooxygenase inhibitor, to attenuate PGE2 formation were determined by co-incubation with IL-1 during prolonged exposure (16 hr); and by brief pre-incubation prior to a subsequent GPCR agonist challenge interval, as shown in FIG. 8. Addition of specified concentrations of ketoprofen during overnight priming with IL-1 abolishes PGE2 formation, with $IC_{50}$ 4.5±0.8 nM determined by nonlinear regression analysis (mean±SEM, n=4 synoviocyte cell lines). Similar determinations (data not shown) were performed with the cyclooxygenase inhibitors etodolac ($IC_{50}$=15.2±4.6 nM, n=4), ketorolac (2.2±0.4 nM, n=4), and indomethacin (3.2±1.5 nM, n=2).

FIG. 8 also shows the ketoprofen concentration-dependent inhibition of the agonist-elicited PGE2 burst in response to a challenge by 100 µM histamine ($IC_{50}$=3.4±0.2 nM, n=3) or 1 µM bradykinin ($IC_{50}$=9.5±2.0 nM, n=3) in synoviocytes primed overnight with IL-1 (10 U/ml). These values are comparable to those observed for ketoprofen inhibition during overnight IL-1 induction of PGE2. This result demonstrates that the onset of inhibition by the COX inhibitor occurs within the 10 min pretreatment interval prior to GPCR agonist addition, consistent with a direct, reversible inhibition of the COX activity and not due a mechanism linked to changes in the expression levels of the prostanoid regulatory enzymes. This immediate inhibitory effect also provides a basis for the immediate effectiveness of this drug when delivered locally to the intra-articular in an irrigation solution during arthroscopic surgery.

Study 4

Induction of IL-6 Production by IL-1 and GPCR Agonists and Inhibition by Ketoprofen The kinetics of induction of interleukin-6 in response to stimulation with IL-1 are described. Synoviocyte cultures were exposed to the indicated treatments with IL-1 plus either histamine to activate signaling through inositol trisphosphate (InsP3)/protein kinase C pathway or isproterenol to activate increases in intracellular cAMP. Production of $PGE_2$, IL-6, and IL-8 were measured in the culture supernatants following 1, 2, 4, 6, and 24 hr treatments. In this experiment, each treatment interval was performed in a separate culture. In the above treatment regime, production of IL-6 was robustly increased by IL-1 following 24-hr exposure, but no IL-6 was detected within the initial 6 hr interval. IL-6 production in response to IL-1 was not augmented further by addition of histamine, and histamine alone failed to stimulate IL-6 production. IL-1 also produced a significant elevation of IL-8 (2000 pg/ml), which was first measurable at 6 hr of treatment. IL-8 production was sustained and greatly increased at 24-hr exposure to IL-1.

The effect of ketoprofen on the induction of cytokine production by IL-1 and GPCR agonists was examined. The protocol also tested the effects of IL-1 concentration dependence on the IL-6 steady state induction. Synoviocyte cultures were exposed to indicated concentrations of IL-1 and GPCR agonists. Culture supernatants were collected and replaced with fresh media aliquots containing the same agonist additions at 8-hr intervals. $PGE_2$, IL-6, and IL-8 in the supernatants were assayed as described.

Figure 9:
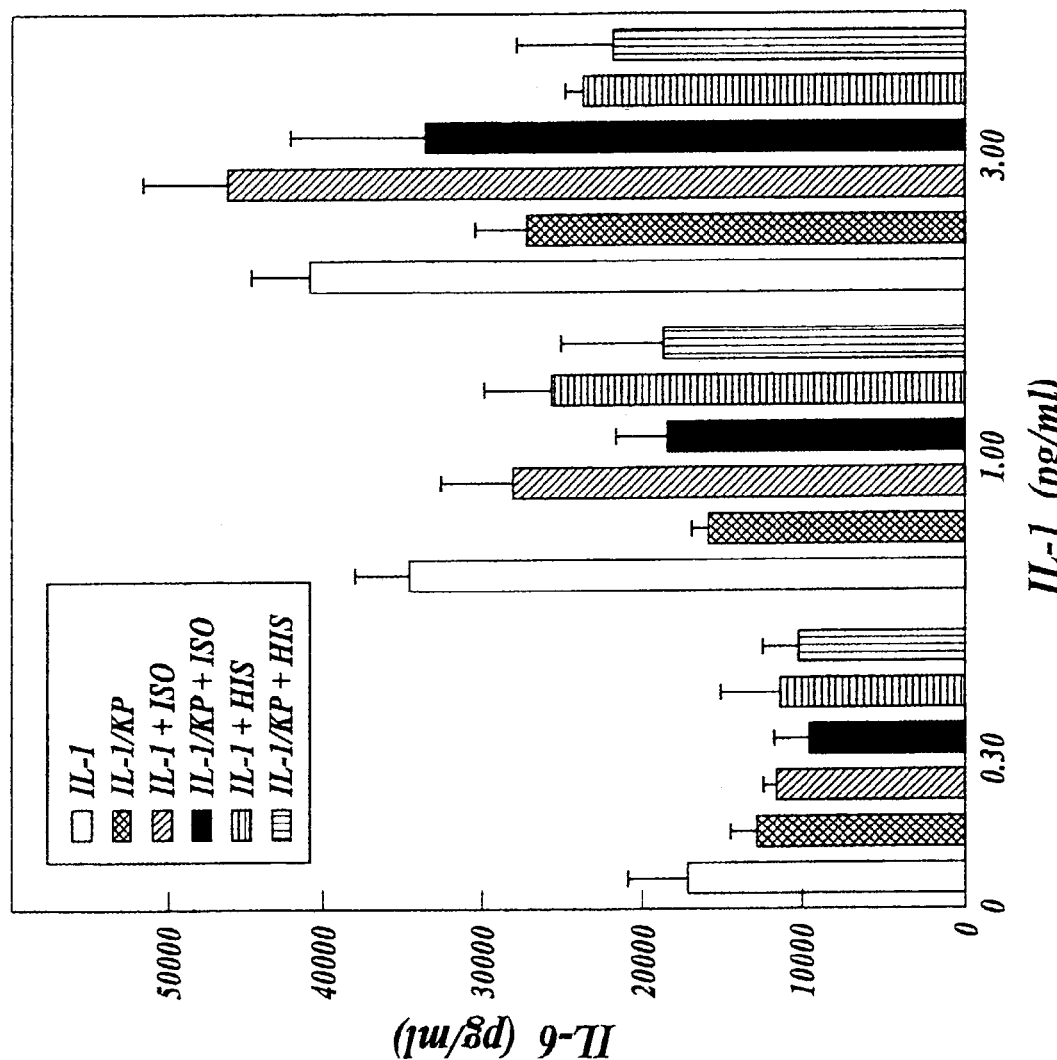
FIG. 9 is a graphical representation of the effect of ketoprofen on IL-6 production by synovial cultures at 16 hours in the presence of the indicated concentrations of IL-1 plus the added G-protein coupled receptor ligands. Cultures were incubated for 16 hours with IL-1 at the indicated concentration (0.3, 1.0 and 3.0 pg/ml) in the absence and presence of 0.75 µM ketoprofen in experimental growth medium with one of the following additional receptor ligands: 1) isoproterenol (ISO) at 1.0 µM to activate the camp pathway, or 2) histamine (HIS) at 100 µM to activate the IP3/calcium pathway. Culture supernatants were collected and replaced with fresh media aliquots containing the same agonist additions at 8 hour intervals. Following treatment, the supernatant medium corresponding to the treatment interval from 8 to 16 hours was collected and analyzed for IL-6.

Data for IL-6 production are shown in FIG. 9, which shows IL-6 production at 16 hr (corresponding to treatment interval from 8–16 hr) in the presence of indicated concentrations of IL-1 plus added ligand. Addition of histamine or isoproterenol does not enhance IL-6 production compared to IL-1 alone. At 1.0 pg/ml IL-1, ketoprofen causes a partial ($\leq 50\%$) inhibition of IL-1-elicited IL-6 production. Furthermore, ketoprofen inhibited IL-6 production in the histamine or isoproterenol/IL-1 co-stimulated samples.

The synoviocyte cell culture model system was used to characterize the synergistic interactions between IL-1 and non-cytokine inflammatory mediators that are important in modulating the destruction of joint tissue, including damage that occurs as a consequence of tissue injury during arthroscopic surgery. The results can be summarized as follows: (1) IL-1 induces large increases in $PGE_2$, IL-6, and IL-8 in cultured synoviocytes, whereas quiescent cultures do not produce detectable quantities of these mediators, (2) the induction of $PGE_2$ occurs most rapidly and results in release of $PGE_2$ to the culture supernatant at 4 hr, followed by IL-8 at 6 hr, and IL-6 at longer intervals, and (3) all three mediators remain elevated in the culture supernatant following 24 hr IL-1 exposure.

In contrast to their actions on $PGE_2$ production, the GPCR agonists do not enhance IL-1 induction of IL-6 or IL-8 and also do not increase IL-6 and IL-8 release following priming with IL-1. IL-1 induction of IL-6 and IL-8 appears to be reinforced by the concomitant induction of $PGE_2$ since ketoprofen reduces the production of these cytokines in response to IL-1. This result indicates that ketoprofen could provide a therapeutic chondroprotective effect when delivered to the joint during surgical procedures.

Taken together, these results demonstrate interactions between specific G-coupled receptor signaling pathways and the activation of synoviocytes by pro-inflammatory stimulation with IL-1. A similar mechanism is expected to be operative in chondrocytes. These interactions provide a means of integrating and modulating pro-inflammatory responses of synoviocytes and chondrocytes depending on inputs from other autocoid or neurotransmitter receptor systems within the joint. These findings underscore the rationale and potential clinical benefit of therapeutic interventions which target inhibition of G-protein coupled receptors that mediate signaling through calcium mobilization, phosphoinositide hydrolysis and PKC activation and are coupled to increases in production of $PGE_2$ in arthroscopic surgery. These receptors on synoviocytes and chondrocytes include histamine $H_1$, bradykinin, Substance P, 5HT2, and the purinergic P2Y receptors.

While the preferred embodiment of the invention has been illustrated and described, it will be appreciated that various changes to the disclosed solutions and methods can be made therein without departing from the spirit and scope of the invention. For example, alternate chondroprotective agents, antibodies and delivery vehicles may be discovered that may augment or replace the disclosed agents, targeting antibodies and delivery vehicles in accordance with the disclosure contained herein. It is therefore intended that the scope of letters patent granted hereon be limited only by the definitions of the appended claims.

The embodiments of the invention in which an exclusive property or privilege is claimed are defined as follows:

1. A targeted drug delivery system for the protection of cartilage, comprising a plurality of chondroprotective agents, wherein at least one of the chondroprotective agents is contained within a delivery vehicle, the delivery vehicle being coupled to an antibody or antibody fragment that is specific to an antigenic determinant localized within the joint, the plurality of chondroprotective agents comprising at least one anabolic chondroprotective agent and at least one inhibitor of cartilage catabolism, each being included in therapeutically effective amounts such that the plurality of chondroprotective agents both inhibit cartilage catabolism and promote cartilage anabolism.

2. The targeted drug delivery system of claim 1, wherein the targeted antigenic determinant is on or within articular cartilage.

3. The targeted drug delivery system of claim 2, wherein the targeted antigenic determinant is on Type II collagen of articular cartilage.

4. The targeted drug delivery system of claim 1, wherein the targeted antigenic determinant is on a cartilage collagen or a cartilage proteoglycan.

5. The targeted drug delivery system of claim 1, wherein the targeted antigenic determinant is found on or within a cell, molecule or structure selected from the group consisting of collagens; proteoglycans; cartilage oligomeric matrix protein, glycoprotein-39; proteoglycan chondroitin-sulfate and glycosaminoglycans; macrophage synoviocytes and fibroblast synoviocytes; and chondrocytes.

6. The targeted drug delivery system of claim 1, wherein the targeted antigenic determinant is on or within the synovium.

7. The targeted drug delivery system of claim 1, wherein the targeted antigenic determinant is an epitope or neoepitope associated with the degeneration of articular cartilage.

8. The targeted drug delivery system of claim 7, wherein the targeted epitopes or neoepitopes are immunolocalized in a superficial layer of articular cartilage in a patient diagnosed with osteoarthritis, rheumatoid arthritis, or other degenerative joint disease.

9. The targeted drug delivery system of claim 7, wherein the targeted antigenic determinant is a neoepitope on Type II collagen or Type II collagen fragments of articular cartilage.

10. The targeted drug delivery system of claim 9, wherein the targeted neoepitope is immunolocalized at a cleavage site generated by the individual or combined action of enzymes selected from the group consisting of matrix metalloproteinase (MMP)-1, MMP-3, MMP-8 and MMP-13.

11. The targeted drug delivery system of claim 7, wherein the targeted epitope or neoepitope is on aggrecan, biglycan, or decorin of articular cartilage.

12. The targeted drug delivery system of claim 7, wherein the targeted epitope or neoepitope is on aggrecan or aggrecan fragments of articular cartilage.

13. The targeted drug delivery system of claim 12, wherein the targeted neoepitope is immunolocalized at a cleavage site generated by the action of an enzyme that belongs to a group consisting of the A Disintegrin And Metalloproteinase with Thrombospondin motifs' (AD-AMTS) family and/or the MMP family.

14. The targeted drug delivery system of claim 13, wherein the targeted neoepitope is immunolocalized at a cleavage site generated by the individual or combined action of ADAMTS-4 and/or ADAMTS-5/11 enzymes.

15. The targeted drug delivery system of claim 1, wherein the targeting antibody or antibody fragment is a humanized, chimeric, or human monoclonal antibody.

16. The targeted drug delivery system of claim 1, wherein the anabolic chondroprotective agent is contained within the targeted delivery vehicle.

17. The targeted drug delivery system of claim 1, wherein the anabolic chondroprotective agent is selected from the group consisting of interleukin (IL) agonists that promote cartilage anabolism, members of the transforming growth factor-n superfamily that promote cartilage anabolism, insulin-like growth factors that promote cartilage anabolism and fibroblast growth factors that promote cartilage anabolism.

18. The targeted drug delivery system of claim 1, wherein the anabolic chondroprotective agent is selected from the group consisting of IL-4, IL-10, IL-13, TGFβ1, TGFβ2, TGFβ3, BMP-2, BMP-4, BMP-6, BMP-7, IGF-1, bFGF and fragments, deletions, additions, amino acid substitutes, mutations and modifications that retain the biological characteristics of the naturally occurring agents.

19. The targeted drug delivery system of claim 1, wherein the anabolic chondroprotective agent is selected from the group consisting of: members of the transforming growth factor-βsuperfamily that promote cartilage anabolism; insulin-like growth factors that promote cartilage anabolism; and fibroblast growth factors that promote cartilage anabolism.

20. The targeted drug delivery system of claim 1, wherein the inhibitor of cartilage catabolism is contained within the targeted delivery vehicle.

21. The targeted drug delivery system of claim 1, wherein the inhibitor of cartilage catabolism is selected from the group consisting of IL-1 receptor antagonists that inhibit cartilage catabolism, TNF-α receptor antagonists that inhibit cartilage catabolism, cyclooxygenase-2 specific inhibitors that inhibit cartilage catabolism, MAP kinase inhibitors that inhibit cartilage catabolism, nitric oxide synthase inhibitors that inhibit cartilage catabolism, and nuclear factor kappa B inhibitors that inhibit cartilage catabolism.

22. The targeted drug delivery system of claim 1, wherein the inhibitor of cartilage catabolism is selected from the group consisting of: inhibitors of matrix metalloproteinases that inhibit cartilage catabolism; cell adhesion molecules that inhibit cartilage catabolism; intracellular signaling inhibitors that inhibit cartilage catabolism; and inhibitors of SH2 domains that inhibit cartilage catabolism.

23. The targeted delivery system of claim 1, wherein the inhibitor of cartilage catabolism comprises an agent selected from an IL-1 receptor antagonist that inhibits cartilage catabolism and a TNF-α receptor antagonist that inhibits cartilage catabolism.

24. The targeted delivery system of claim 1, wherein the anabolic chondroprotective agent and the inhibitor of cartilage catabolism each comprise a protein.

25. The targeted drug delivery system of claim 1, wherein the anabolic chondroprotective agent and the inhibitor of cartilage catabolism are both contained within the targeted delivery vehicle.

26. The targeted drug delivery system of claim 1, comprising a plurality of targeted delivery vehicles, wherein the anabolic chondroprotective agent and the inhibitor of cartilage catabolism are separately contained within a first and a second of the plurality of targeted delivery vehicles, respectively.

27. The targeted drug delivery system of claim 26, wherein the first and second targeted delivery vehicles are selected to result in temporally distinct release kinetics for the contained anabolic chondroprotective agent and the contained inhibitor of cartilage catabolism.

28. The targeted delivery system of claim 1, wherein the targeted delivery vehicle comprises targeted immunoparticles.

29. The targeted delivery system of claim 28, wherein the targeted immunoparticles comprise nanoparticles.

30. The targeted delivery system of claim 29, wherein the nanoparticles have a diameter ranging from 5 nanometers to 750 nanometers.

31. The targeted delivery system of claim 29, wherein the nanoparticles have a diameter ranging from 10 to 500 nanometers.

32. The targeted delivery system of claim 29, wherein the nanoparticles have a diameter ranging from 20 to 200 nanometers.

33. The targeted delivery system of claim 29, wherein the nanoparticles are formed from a polymer selected from the group consisting of hyaluronan, chitosan, collagen, gelatin, alginate, polylactic acid (PLLA), polyglycolic acid (PGA) and PLGA.

34. The targeted delivery system of claim 29, wherein the nanoparticles provide sustained release of the chondroprotective agents over a period of from 1 day to 4 weeks.

35. The targeted delivery system of claim 1, further comprising a carrier suitable for intravenous, intramuscular, subcutaneous or inhalation administration.

36. The targeted delivery system of claim 1, further comprising one or more additional therapeutic agents.

37. The targeted delivery system of claim 1, further comprising one or more pain or inflammation inhibitory agents.

38. The targeted delivery system of claim 37, wherein the pain or inflammation inhibitory agents are selected from the group consisting of serotonin receptor antagonists, serotonin receptor agonists, histamine receptor antagonists, bradykinin receptor antagonists, kallikrein inhibitors, tachykinin receptor antagonists, calcitonin gene-related peptide (CGRP) receptor antagonists, interleukin receptor antagonists, inhibitors of enzymes active in the synthetic pathway for arachidonic acid metabolites, prostanoid receptor antagonists, leukotriene receptor antagonists, opioid receptor agonists, purinoceptor agonists and antagonists, adenosine triphosphate (ATP)-sensitive potassium channel openers, and calcium channel antagonists.

39. A method of protecting cartilage in a patient, comprising:
delivering to the patient in need thereof a targeted drug delivery system comprising a plurality of chondroprotective agents contained within a delivery vehicle, the delivery vehicle being coupled to an antibody or antibody fragment that is specific to an antigenic determinant localized within the joint, the plurality of chondroprotective agents comprising at least one anabolic chondroprotective agent and at least one inhibitor of cartilage catabolism, each being included in therapeutically effective amounts such that the plurality of chondroprotective agents both inhibit cartilage catabolism and promote cartilage anabolism.

40. A method of protecting cartilage in a patient, comprising:
concurrently administrating to the patient in need thereof a plurality of chondroprotective agents, wherein at least one of the chondroprotective agents is contained within a delivery vehicle, the delivery vehicle being coupled to an antibody or antibody fragment that is specific to an antigenic determinant localized within the joint, the plurality of chondroprotective agents comprising at least one anabolic chondroprotective agent and at least one inhibitor of cartilage catabolism, the plurality of chondroprotective agents each being included in therapeutically effective amounts such that the plurality of chondroprotective agents both inhibit cartilage catabolism and promote cartilage anabolism.

41. A method of protecting cartilage in a patient, comprising:
administering to the patient in need thereof a plurality of chondroprotective agents, wherein at least one of the chondroprotective agents is contained within a delivery vehicle and the chondroprotective agents are administered so as to result in the coincident presence of the chondroprotective agents within the joint, the delivery vehicle being coupled to an antibody or antibody fragment that is specific to an antigenic determinant localized within the joint, the plurality of chondroprotective agents comprising at least one anabolic chondroprotective agent and at least one inhibitor of cartilage catabolism, each being included in therapeutically effective amounts such that the plurality of chondroprotective agents both inhibit cartilage catabolism and promote cartilage anabolism.

* * * * *

UNITED STATES PATENT AND TRADEMARK OFFICE
CERTIFICATE OF CORRECTION

PATENT NO. : 7,067,144 B2  
APPLICATION NO. : 10/356649  
DATED : June 27, 2006  
INVENTOR(S) : Gregory A. Demopulos et al.

It is certified that error appears in the above-identified patent and that said Letters Patent is hereby corrected as shown below:

| COLUMN | LINE | |
|---|---|---|
| Column 37 | 47 | "IL-10" should read --IL-1β-- |
| Column 38 | 17 | "proteoglyean" should read --proteoglycan-- |
| Column 43 | 67 | "IL-10" should read --IL-1β-- |
| Column 44 | 13 | "IL-11" should read --IL-1β-- |
| Column 44 | 62 | "rhL" should read --rhIL-- |
| Column 44 | 63 | "1-10" should read --IL-10-- |
| Column 47 | 11 | "LA5" should read --L45-- |
| Column 56 | 22 | "IL-β3" should read --IL-1β-- |
| Column 71 | 13 | "neurokintin$_2$" should read --neurokinin$_2$-- |

Signed and Sealed this

Twenty-eighth Day of November, 2006

JON W. DUDAS  
*Director of the United States Patent and Trademark Office*